United States Patent
Hayashi et al.

(10) Patent No.: US 6,642,228 B1
(45) Date of Patent: Nov. 4, 2003

(54) α1B-ADRENERGIC RECEPTOR ANTAGONISTS

(75) Inventors: Ryoji Hayashi, Kanagawa (JP); Eiji Ohmori, Shiga (JP); Masafumi Isogaya, Kanagawa (JP); Mitsuhiro Moriwaki, Kanagawa (JP); Hiroki Kumagai, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/763,684
(22) PCT Filed: Jun. 22, 2000
(86) PCT No.: PCT/JP00/04068
§ 371 (c)(1), (2), (4) Date: Apr. 13, 2001
(87) PCT Pub. No.: WO00/78716
PCT Pub. Date: Dec. 28, 2000

(30) Foreign Application Priority Data

Jun. 24, 1999 (JP) .............................. 11/178170

(51) Int. Cl.$^7$ ................... C07D 401/04; C07D 403/04; A61K 31/4427; A61K 31/496
(52) U.S. Cl. ................ 514/230.5; 514/235.5; 514/253.01; 514/249; 514/307; 514/314; 514/319; 514/320; 514/321; 514/322; 514/323; 514/324; 514/326; 514/331; 514/316; 544/129; 544/130; 544/124; 544/360; 544/353; 544/364; 544/90; 546/144; 546/146; 546/148; 546/150; 546/165; 546/175; 546/167; 546/173; 546/176; 546/200; 546/187; 546/189; 546/191; 546/196; 546/201; 546/202; 546/198; 546/199
(58) Field of Search ................ 544/129, 130, 544/124, 360, 353, 364, 90; 546/146, 144, 148, 150, 165, 175, 167, 173, 176, 200, 187, 189, 191, 196, 201, 202, 198, 199; 514/235.5, 253.01, 249, 230.5, 314, 307, 319, 320, 321, 322, 323, 324, 326, 331, 316

(56) References Cited

U.S. PATENT DOCUMENTS

| 3,331,843 A | 7/1967 | Tomcufcik et al. ......... 260/268 |
| 5,017,703 A | * 5/1991 | Matsuo et al. ............... 546/201 |
| 5,296,497 A | * 3/1994 | Hartog et al. ................ 514/357 |
| 5,472,966 A | * 12/1995 | Sloan et al. ................. 514/255 |
| 6,066,637 A | 5/2000 | Kelly et al. .................. 514/253 |

FOREIGN PATENT DOCUMENTS

| EP | 398413 | 11/1990 |
| EP | 434561 | 6/1991 |
| EP | 732332 | 9/1996 |
| EP | 735024 | 10/1996 |
| GB | 1047935 | 11/1966 |
| JP | 50-108264 | 8/1975 |
| JP | 56-53654 | 5/1981 |
| WO | WO 92/15301 | 9/1992 |
| WO | WO 95/17182 | 6/1995 |
| WO | WO 98/38189 | 9/1998 |
| WO | WO 99/20621 | 4/1999 |
| WO | WO 99/55695 | 11/1999 |

OTHER PUBLICATIONS

Chemical Abstracts, vol. 63, col. 13290, Par. H to col. 13291, Par. g.
Chemical Abstracts, vol. 62, col. 12339, Par. b–c.
Srivastava Sandhya, et al., "Synthesis of 7–chloro–4–substituted aminoquinolines and their in vitro ability to produce methemoglobin in canine hemolyzate", Bioorg.Med.Chem.Lett., (1997), 7(21), pp. 2741–2746.

* cited by examiner

Primary Examiner—Mukund J. Shah
Assistant Examiner—Kahsay Habte
(74) Attorney, Agent, or Firm—Piper Rudnick LLP

(57) ABSTRACT

There are provided compounds represented by the general formula (I):

formula (I):

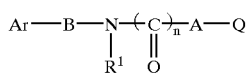

[wherein Ar is indole etc., $R^1$ is hydrogen etc., B is bond, or B—N—$R^1$ forms a ring structure and is piperidine etc., n is 0, 1, etc., A is trimethylene, butylene, etc., Q is piperidine, isoindoline, etc.], or pharmacologically acceptable acid addition salts thereof, and α1B adrenoceptor antagonists composed of these substances. The invented compounds are antagonists having high affinity for α1B adrenoceptor and are useful as pharmaceutical agents for use in prophylaxis/therapy of diseases (e.g., hypertension) in which α1B adrenoceptor is involved or as pharmacological tools for elucidation of physiological activities mediated by α1B adrenoceptor.

13 Claims, No Drawings

α1B-ADRENERGIC RECEPTOR ANTAGONISTS

TECHNICAL FIELD

The present invention relates to antagonists having affinity for α1B adrenoceptor.

BACKGROUND ART

Noradrenaline and adrenaline play important roles as neurotransmitters of the sympathetic nerve system or as vasoactive hormones in the regulation of physiological functions.

These noradrenaline and adrenaline transmit information into the cell by binding with receptors on a cell menbrane. The receptors were initially classified as a receptors and β receptors by Ahlquist (Am. J. Physiol., 153, 586(1948)), and thereafter, the α receptors were classified as α1 receptors and α2 receptors, and the β receptors were classified as β1 receptor and β2 receptor.

Of these adrenoceptors, it has been cleared that α1 receptors are important receptors which are associated with a variety of physiological activities such as vascular smooth muscle contraction, pupil dilator muscle contraction, cardiac muscle contraction, urethral smooth muscle contraction, renin secretion in the kidney, glycogenolysis in the liver, and lipolysis in fat cells.

The α1 receptors have further been classified as three subtypes, α1a, α1b, and α1d, by means of molecular biological techniques advanced in recent years (Pharmacol. Rev., 47, 267(1995)). Initially, there was some confusion between the molecular-biological classification using clones and the pharmacological classification, but the classification is now unified such that α1a, α1b, and α1d receptors, which are classified based on clone receptors, respectively correspond to α1A, α1B, and α1D receptors, which are pharmacologically classified.

Each of the α1 receptor subtypes is considered to exhibit pharmacological and tissue specificities, and it is very important to provide compounds having selectivity for each of the α1 receptor subtypes in order to elucidate physiological activities mediated by individual receptor subtypes and to remedy diseases in which they are involved.

Prazosin is widely used as a therapeutic agent for hypertension at present and has been already known to have no selectivity for the α1 receptor subtypes. Then, a multiplicity of compounds have been synthetically obtained, and 5-methylurapidil and KMD-3213, for example, have been developed as compounds having high selectivity for α1A receptor (Exp. Opin. Invest. Drugs, 6, 367(1997); Mol. Pharmacol., 48, 250(1995)). Experiments using these compounds having high selectivity for the α1A receptor suggested that the α1A receptor is deeply concerned in urethral smooth muscle contraction, and it is now under study to apply α1A receptor antagonists as therapeutic agents for dysuria due to prostatic hypertrophy (New Current, 7, 14(1996)).

In contrast, there are very few reports on compounds e - having selectivity for the α1B receptor, and spiperone and AH 1110A presently reported are not sufficient in their selectivity and affinity (Trend. Pharmacol. Sci., 15, 167 (1994); Soc. Neurosci. Abstr., 20, 526(1994); J. Computer-Aided Mol. Design, 10, 545(1996)). Therefore, physiological activities mediated by the α1B receptor have not yet been completely elucidated. However, recent experiments using α1B transgenic mice have suggested that the α1B receptor is involved in vascular muscle contraction, hypercardia, and tumorigenesis (Proc. Natl. Acad. Sci. USA, 87, 2896(1990); Proc. Natl. Acad. Sci. USA, 91, 10109 (1994)). Additionally, experiments using α1B receptor knock out mice have suggested that the α1B receptor is involved in vasopressor responses (Proc. Natl. Acad. Sci. USA 94, 11589(1997)). Furthermore, a variety of experiments have reported that a stimulus to the α1B receptor enhances the growth of vascular smooth muscle cells (J. Biol. Chem., 270, 30980(1995), and that there is a high possibility that the α1B receptor is involved in contraction in human coronary artery and human cerebral artery induced by a stimulus to the α1 receptors ("Kekkan to Naihi" (Blood Vessel and Endothelium), 6, 431(1996)), for example. Such α1B receptor antagonists are expected as therapeutic agents for, for example, hypertension, high ocular tension, congestive heart failure, and arrhythmia (WO97/11698) . Consequently, demands are made to create compounds having affinity for the α1B receptor and have high selectivity for the receptor, in order to create novel pharmaceutical agents.

The present invention therefore relates to α1 adrenoceptor antagonists, and it is an object of the invention to provide antagonists which are selective for the α1 receptor subtypes, and more specifically, to provide antagonists which have selectivity for the α1B adrenoceptor.

DISCLOSURE OF INVENTION

The present invention relates to an α1B adrenoceptor antagonist which includes a compound represented by the general formula (I) or a pharmacologically acceptable acid addition salt thereof:

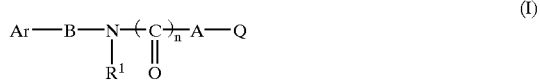

(I)

[wherein Ar is indole, naphthalene, quinoline, benzimidazole, benzofuran, benzothiophene, benzisoxazole, or 2-ketobenzimidazoline, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 1 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$R^1$ is hydrogen, alkyl having 1 to 6 carbon atoms, aryl having 6 to 12 carbon atoms, alkenyl having 2 to 9 carbon atoms, or cycloalkyl having 3 to 8 carbon atoms;

B is a bond, or alkylene group having 1 to 3 carbon atoms which is unsubstituted or substituted with the groups selected from the group consisting of alkyl group having 1 to 8 carbon atoms, halogen, and hydroxy;

or B—N—$R^1$ forms a ring structure and is piperidine, piperazine, or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

n denotes an integer of 0 or 1;

A is alkylene having 2 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:

1) —NR$^2$R$^3$, wherein each of R$^2$ and R$^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR$^2$R$^3$ together forms piperidine, pyrrolidine, 1,3,4-trihydroisoquinoline, isoindoline, piperazine, morpholine, 2-piperidone, 2-pyrrolidone, indoline, 2,3,4-trihydroquinoline, 2,3,4-trihydroquinoxaline, dihydrobenzoxazine, benzothiane, phthalimide, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

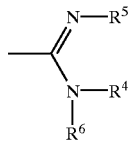

(II)

(wherein each of R$^4$, R$^5$, R$^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthip group having 1 to 8 carbon atoms, and arylthio group having 6 to 15 carbon atoms), or R$^4$ and R$^5$ together form an imidazoline ring)].

In another. aspect, the present invention relates to a compound represented by the general formula (III) or a pharmacologically acceptable acid addition salt thereof:

Ar$^2$—D—A—Q$^2$ (III)

[wherein D represents one of the following formulae 1) to 5), each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

1) 

2) 

3) 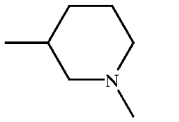

4) 

5) 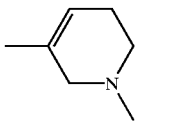

Ar² is indole, naphthalene, quinoline, benzimidazole, benzofuran, or benzothiophene, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is alkylene having 3 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:
1) $-NR^2R^3$,
wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkbxycarbonyl group having 2 to 9 carbon atoms, aminocarbonyl group having 1 to 15 carbon atoms, alkylthio group having 1 to 8 carbon atoms, and arylthio group having 6 to 15 carbon atoms, where $R^2=R^3=H$ and $R^2=R^3=ethyl$ are excluded), or $-NR^2R^3$ together forms piperidine, pyrrolidine, 1,3,4-trihydroisoquinoline, isoindoline, piperazine, morpholine, 2-piperidone, 2-pyrrolidone, indoline, 2,3,4-trihydroquinoline, 2,3,4-trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 oto 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arytthio group having 6 to 15 carbon atoms; or 2) the formula (II):

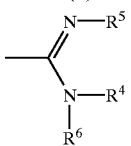

(II)

(wherein each of $R^4$, $R^5$, $R^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or $R^4$ and $R^5$ together form an imidazoline ring)].

BEST MODE FOR CARRYING OUT THE INVENTION

Of α1B adrenoceptor antagonists according to the present invention including a compound represented by the general formula (I) or a pharmaceutically acceptable acid addition salt thereof, preferred compounds are compounds in which n is 0;

Ar is indole, naphthalene, quinoline, benzimidazole, benzofuran, or benzothiophene, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B is alkylene having 2 or 3 carbon atoms, which is unsubstituted or substituted with the groups selected from the group consisting of alkyl group having 1 to 8 carbon atoms, halogen, and hydroxy, or B—N—$R^1$ forms a ring structure and is piperidine, piperazine, or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

Q is:
1) —$NR^2R^3$ (wherein each of $R^2$ and $R^3$ is independently hydrogen, alkylhaving 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —$NR^2R^3$ together forms piperidine, pyrrolidine, 1,3,4-trihydroisoquinoline, isoindoline, piperazine, morpholine, indoline, 2,3,4-trihydroquinoline, 2,3,4-trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and aryl thio group having 6 to 15 carbon atoms; or 2) the formula (II):

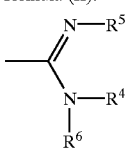

(II)

(wherein $R^4$, $R^5$, and $R^6$ have the same meanings as defined above).

Among them, more preferred compounds are compounds in which n is 0;

Ar is indole, naphthalene, quinoline, or benzimidazole, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B—N—$R^1$ forms a ring structure and is piperidine or piperazine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

A is alkylene having 2 to 8 carbon atoms or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —$NR^2R^3$ (wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —$NR^2R^3$ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

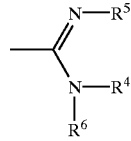

(II)

(wherein $R^4$, $R^5$, and $R^6$ have the same meanings as defined above)

Of these compounds, especially preferred compounds are compounds in which n is 0;

Ar is indole or naphthalene, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B—N—$R^1$ forms a ring structure and is represented by the following formula 1) or 2), each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

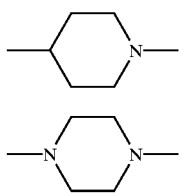

1)

2)

A is alkylene having 3 to 8 carbon atoms, which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —$NR^2R^3$ (wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —$NR^2R^3$ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arlthio group having 6 to 15 carbon atoms; or 2) the formula (II):

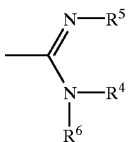

(II)

(wherein $R^4$, $R^5$, and $R^6$ have the same meanings as defined above).

As examples of substituents on Ar in the compounds represented by the general formula (I), halogen includes fluoro, chloro, bromo, and iodo; acylamino group having 1 to 9 carbon atoms includes —$NHCOCH_3$ and —NHCOPh; alkylamino group having 1 to 8 carbon atoms includes methylamino, ethylamino, n-propylamino, isopropylamino, and cyclohexylamino; arylamino group having 6 to 15 carbon atoms includes phenylamino; dialkylamino group having 2 to 16 carbon atoms includes dimethylamino, diethylamino, di(n-propyl)amino, diisopropylamino, and di(cyclohexyl)amino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —$SO_2NH_2$, —$SO_2NHMe$, —$SO_2NMe_2$, —$SO_2NHPh$, and —$SO_2NPh_2$; alkoxycarbonyl group having 1 to 9 carbon atoms includes —COOMe, and —COOEt; aminocarbonyl group having 1 to 15 carbon atoms includes —$CONH_2$, —CONHMe, —$CONMe_2$, —$CONH^tBu$, —CONHPh, and —$CONPh_2$; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Of these substituents, preferred are identical or different one or two fluoro, chloro, bromo, nitro, —$NHCOCH_3$, —NHCOPh, amino, methylamino, ethylamino, n-propylamino, isopropylamino, phenylamino, dimethylamino, diethylamino, di(n-propyl)amino, diisopropylamino, hydroxy, methoxy, ethoxy, n-propoxy, isopropoxy, phenoxy, trifluoromethyl, trifluoromethoxy, 2,2,2-trifluoroethoxy, cyano, —$SO_2NH_2$, —$SO_2NHMe$, —$SO_2NMe_2$, —$SO_2NHPh$, —$CONH_2$, —CONHMe, —$CONMe_2$, —$CONH^tBu$, methylthio, ethylthio, and phenylthio. Among them, more preferred are identical or different one or two fluoro, chloro, bromo, nitro, —$NHCOCH_3$, amino, methylamino, isopropylamino, phenylamino, dimethylamino, diisopropylamino, hydroxy, methoxy, ethoxy, isopropoxy, trifluoromethyl, trifluoromethoxy, cyano, —SO$_2$NH$_2$, —SO$_2$NHMe, —SO$_2$NMe$_2$, —SO$_2$NHPh, —CONH$_2$, —CONMe$_2$, methylthio, and phenylthio, of which identical or different one or two fluoro, chloro, bromo, nitro, amino, methylamino, methoxy, ethoxy, trifluoromethyl, trifluoromethoxy, —SO$_2$NH$_2$, and —CONH$_2$ are especially preferred.

In B, preferred alkylene having 1 to 3 carbon atoms, which may be substituted with alkyl group having 1 to 8 carbon atoms, halogen, or hydroxyl group, are ethylene, 1-methylethylene, 2-methylethylene, 1-chloroethylene, 1-fluoroethylene, 2-chloroethylene, 2-fluoroethylene, 1-hydroxyethylene, 1,3-trimethylene, 1,3-(2-methyl) trimethylene, 1,3-(3-methyl)trimethylene, 1,3-(2-chloro) trimethylene, 1,3-(2-fluoro)trimethylene, 1,3-(2,2-difluoro) trimethylene, 1,3-(2-hydroxy)trimethylene, and 1,3-(1-hydroxy)trimethylene. Among them, ethylene, 2-methylethylene, 2-fluoroethylene, 1-hydroxyethylene, 1,3-trimethylene, 1,3-(2-methyl)trimethylene, 1,3-(3-methyl)trimethylene, and 1,3-(1-hydroxy)trimethylene are more preferred, of which ethylene, 1-hydroxyethylene, and 2-methylethylene are especially preferred.

When B—N—R$^1$ is piperidine, piperazine, or 2,3,6-trihydropyridine, Ar is preferably substituted at the 3- or 4-position, and is typically preferably substituted at the 4-position.

As examples of substituents on piperidine, piperazine, or 2,3,6-trihydropyridine in the above case, halogen includes fluoro, chloro, and bromo; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; haloalkyl group having 1 to 8 carbon atoms includes trifluoromethyl and 2,2,2-trifluoroethyl; aminosulfonyl group having 0 to 15 carbon atoms includes —SO$_2$NH$_2$, —SO$_2$NHMe, —SO$_2$NMe$_2$, —SO$_2$NHPh, and —SO$_2$NPh$_2$; alkoxycarbonyl group having 2 to 9 carbon atoms includes —COOMe, and —COOEt; aminocarbonyl group having 1 to 15 carbon atoms includes —CONH$_2$, —CONHMe, —CONMe$_2$, —CONH$^t$Bu, —CONHPh, and —CONPh$_2$; hydroxyalkyl group having 1 to 8 carbon atoms includes hydroxymethyl, 1-hydroxyethyl, 2-hydroxyethyl, and 3-hydroxypropyl; alkylcarbonyl group having 2 to 9 carbon atoms includes —COMe, and —COEt; arylcarbonyl having 7 to 16 carbon atoms includes —COPh, naphthylcarbonyl, and 2-furanylcarbonyl; aralkyl having 7 to 15 carbon atoms includes benzyl, 2-phenylethyl, and 3-phenylpropyl; and other substituents include hydroxy and —COOH. Among these substituents, preferred are identical or different one or two fluoro, —NHCOCH$_3$, —NHCOPh, hydroxy, methyl, isopropyl, t-butyl, phenyl, trifluoromethyl, trifluoromethoxy, —SO$_2$NH$_2$, —SO$_2$NHMe, —SO$_2$NMe$_2$, —SO$_2$NHPh, —SO$_2$NPh$_2$, —COOH, —COOMe, —CONH$_2$, —CONHMe, —CONMe$_2$, —CONH$^t$Bu, —CONHPh, and —CONPh$_2$. Among them, identical or different one or two fluoro, hydroxy, methyl, isopropyl, phenyl, trifluoromethyl, trifluoromethoxy, —SO$_2$NH$_2$, —SO$_2$NHMe, —SO$_2$NHPh, —COOH, —COOMe, —CONH$_2$, —CONHMe, —CONH$^t$Bu, and —CONMe$_2$ are more preferred, of which one fluoro, hydroxy, methyl, phenyl, trifluoromethyl, —SO$_2$NH$_2$, —CONH$_2$, and —CONH$^t$Bu are especially preferred.

In R$^1$, alkyl having 1 to 6 carbon atoms includes methyl, ethyl, n-propyl, isopropyl, n-butyl, isobutyl, sec-butyl, t-butyl, n-pentyl, isopentyl, neopentyl, and n-hexyl; aryl having 6 to 12 carbon atoms includes phenyl, naphthyl, and biphenyl; alkenyl having 2 to 9 carbon atoms includes ethenyl, 2-propenyl, 2-pentenyl, 2-octenyl, 3-butenyl, 3-hexenyl, 4-pentenyl, 4-octenyl, 1,3-butadienyl, 1,3-pentadienyl, 2,4-pentadienyl, 1,3,5-hexatrienyl, 1,3,5-heptatrienyl, 2,4,6-heptatrienyl (these also include isomers (E form and Z form) with respect to double bond); cycloalkyl having 3 to 8 carbon atoms includes cyclopropyl, cyclobutyl, cyclohexyl, and cycloheptyl; aralkyl having 7 to 15 carbon atoms includes benzyl, 2-phenylethyl, 3-phenylpropyl, 2-phenylpropyl, and 4-phenylbutyl. Of these groups, methyl, ethyl, n-propyl, isopropyl, phenyl, 2-propenyl, cyclopropyl, cyclohexyl, benzyl, and 2-phenylethyl are preferred. Among them, methyl, phenyl, 2-propenyl, benzyl, and 2-phenylethyl are more preferred, of which methyl, phenyl, and 2-phenylethyl are especially preferred.

In A, alkylene having 2 to 8 carbon atoms includes ethylene, 1,3-trimethylene, 1,4-butylene, 1,5-pentamethylene, 1,6-hexamethylene, and 1,7-heptamethylene; phenylene includes 1,4-phenylene, and 1,3-phenylene; cycloalkylene having 3 to 8 carbon atoms includes 1,2-cyclopentylene, 1,3-cyclopentylene, 1,2-cyclohexylene, 1,3-cyclohexylene, 1,4-cyclohexylene, and 1,5-cyclooctylene. Among these groups, 1,3-trimethylene, 1,4-butylene, 1,5-pentamethylene, 1,6-hexamethylene, 1,4-phenylene, 1,2-cyclohexylene, 1,3-cyclohexylene, 1,4-cyclohexylene, and 1,5-cyclooctylene are preferred, of which 1,3-trimethylene, 1,4-butylene, 1,5-pentamethylene, and 1,4-cyclohexylene are especially preferred.

As examples of substituents on the alkylene having 2 to 8 carbon atoms, phenylene, or cycloalkylene having 3 to 8 carbon atoms in A, halogen includes fluoro, chloro, bromo, and iodo; acylamino group having 1 to 9 carbon atoms includes —NHCOCH$_3$ and —NHCOPh; alkylamino group having 1 to 8 carbon atoms includes methylamino, ethylamino, n-propylamino, isopropylamino, and cyclohexylamino; arylamino group having 6 to 15 carbon atoms includes phenylamino; dialkylamino group having 2 to 16 carbon atoms includes dimethylamino, diethylamino, di(n-propyl)amino, diisopropylamino, di(cyclohexyl)amino, piperidino, and pyrrolidino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —SO$_2$NH$_2$, —SO$_2$NHMe, —SO$_2$NMe$_2$, —SO$_2$NHPh, and —SO$_2$NPh$_2$; alkoxycarbonyl group having 2 to 9 carbon atoms includes —COOMe, and —COOEt; aminocarbonyl group having 1 to 15 carbon atoms includes —CONH$_2$, —CONHMe, —CONMe$_2$, —CONH$^t$Bu, —CONHPh, and —CONPh$_2$; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Among these substituents, identical or different one or more fluoro, chloro, amino, methylamino, isopropylamino, phenylamino, dimethylamino, 1-piperidino, 1-pyrrolidino, hydroxy, methyl, isopropyl, phenyl, methoxy, isopropoxy, phenoxy, trifluoromethyl, trifluoromethoxy, cyano, —SO$_2$NH$_2$, —SO$_2$NHMe, —SO$_2$NMe$_2$, —SO$_2$NHPh, —SO$_2$NPh$_2$, —COOH, —COOMe, —CONH$_2$, —CONHMe, —CONMe$_2$, —CONH$^t$Bu, —CONHPh, and —CONPh$_2$ are preferred, of which identical or different one or more fluoro, amino, methylamino, 1-piperidino, hydroxy, methyl, isopropyl, methoxy, and trifluoromethyl are especially preferred.

Of $R^2$, $R^3$, $R^4$, $R^5$, and $R^6$ in Q, alkyl having 1 to 6 carbon atoms includes methyl, ethyl, n-propyl, isopropyl, n-butyl, isobutyl, sec-butyl, t-butyl, n-pentyl, isopentyl, neopentyl, and n-hexyl; cycloalkyl having 3 to 8 carbon atoms includes cyclopropyl, cyclobutyl, cyclohexyl, and cycloheptyl; aryl having 6 to 15 carbon atoms includes phenyl, naphthyl, and biphenyl; aralkyl having 7 to 15 carbon atoms includes benzyl, 2-phenylethyl, 3-phenylpropyl, 2-phenylpropyl, and 4-phenylbutyl; alkenyl having 2 to 9 carbon atoms includes ethenyl, 2-propenyl, 2-pentenyl, 2-octenyl, 3-butenyl, 3-hexenyl, 4-pentenyl, 4-octenyl, 1,3-butadienyl, 1,3-pentadienyl, 2,4-pentadienyl, 1,3,5-hexatrienyl, 1,3,5-heptatrienyl, and 2,4,6-heptatrienyl (these also include isomers (E form and Z form) with respect to double bond). Of these groups, methyl, n-propyl, cyclopropyl, benzyl, 2-phenylethyl, 3-phenylpropyl, 2-phenylpropyl, 4-phenylbutyl, and 2-propenyl are preferred. Among them, methyl, cyclopropyl, benzyl, 2-phenylethyl, 3-phenylpropyl, 2-phenylpropyl, 4-phenylbutyl, and 2-propenyl are more preferred, of which methyl, benzyl, 2-phenylethyl, 3-phenylpropyl, and 2-propenyl are especially preferred.

When $R^2$, $R^3$, $R^4$, $R^5$, and $R^6$ are aryl having 6 to 15 carbon atoms or aralkyl having 7 to 15 carbon atoms, as examples of substituents on the aryl, halogen includes fluoro, chloro, and bromo; acylamino group having 1 to 9 carbon atoms includes —NHCOCH$_3$ and —NHCOPh; alkylamino group having 1 to 8 carbon atoms includes methylamino, ethylamino, n-propylamino, isopropylamino, and cyclohexylamino; arylamino group having 6 to 15 carbon atoms includes phenylamino; dialkylamino group having 2 to 16 carbon atoms includes dimethylamino, diethylamino, di(n-propyl)amino, diisopropylamino, di(cyclohexyl)amino, piperidino, and pyrrolidino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —SO$_2$NH$_2$, —SO$_2$NHMe, —SO$_2$NMe$_2$, —SO$_2$NHPh, and —SO$_2$NPh$_2$; alkoxycarbonyl group having 2 to 9 carbon atoms includes —COOMe, and —COOEt; aminocarbonyl group having 1 to 15 carbon atoms includes —CONH$_2$, —CONHMe, —CONMe$_2$, —CONH$^t$Bu, —CONHPh, and —CONPh$_2$; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Among these substituents, identical or different one or more fluoro, chloro, amino, methylamino, isopropylamino, phenylamino, dimethylamino, 1-piperidino, 1-pyrrolidino, hydroxy, methyl, isopropyl, phenyl, methoxy, isopropoxy, phenoxy, trifluoromethyl, trifluoromethoxy, cyano, —SO$_2$NH$_2$, —SO$_2$NHMe, —SO$_2$NMe$_2$, —SO$_2$NHPh, —SO$_2$NPh$_2$, —COOH, —COOMe, —CONH$_2$, —CONHMe, —CONMe$_2$, —CONH$^t$Bu, —CONHPh, and —CONPh$_2$ are preferred, of which identical or different one or more fluoro, amino, methylamino, 1-piperidino, hydroxy, methyl, phenyl, isopropyl, methoxy, trifluoromethyl, —SO$_2$NH$_2$, and —CONH$_2$ are especially preferred.

As Q, preferred are methylamine, 2-phenylethylamine, piperidine, pyrrolidine, 1,3,4-trihydroisoquinoline, dimethylamine, di(2-phenylethyl)amine, isoindoline, piperazine, morpholine, 2-piperidone, 1-guanidine, and 2-imidazoline. Among them, 2-phenylethylamine, piperidine, 1,3,4-trihydroisoquinoline, dimethylamine, di(2-phenylethyl)amine, isoindoline, and 2-imidazoline are more preferred, of which 2-phenylethylamine, piperidine, 1,3,4-trihydroisoquinoline, isoindoline, and 2-imidazoline are especially preferred.

Of compounds represented by the general formula (III) or pharmacologically acceptable acid addition salts thereof according to the present invention, preferred compounds are compounds in which D represents one of the following formulae 1) to 3), each of which is unsubstituted or substituted with the groups selected from the group consisting of halogen, hydroxy, alkyl group having 1 to 8 carbon atoms, aryl group having 6 to 15 carbon atoms, haloalkyl group, having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

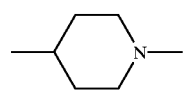

1)

2)

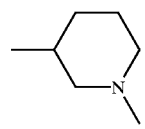

3)

$Ar^2$ is indole, naphthalene, quinoline, or benzimidazole, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is an alkylene having 3 to 8 carbon atoms or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:

1) $-NR^2R^3$, wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms, where $R^2=R^3=H$ and $R^2=R^3=$ethyl are excluded), or $-NR^2R^3$ together forms piperidine, pyrrolidine, 1,3,4-trihydroisoquinoline, isoindoline, piperazine, morpholine, indoline, 2,3,4-trihydroquinoline, 2,3,4-trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms and arylthio group having 6 to 15 carbon atoms; or 2) the formula (II):

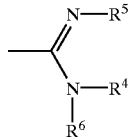

(II)

(wherein each of $R^4$, $R^5$, $R^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or $R^4$ and $R^5$ together form an imidazoline ring).

In more preferred compounds, D represents one of the following formulae 1) and 2), each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

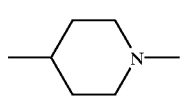

1)

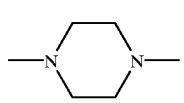

2)

$Ar^2$ is indole or naphthalene, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is alkylene having 3 to 8 carbon atoms, which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:

1) —$NR^2R^3$, wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms, where $R^2$=$R^3$=H and $R^2$=$R^3$=ethyl are excluded), or —$NR^2R^3$ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

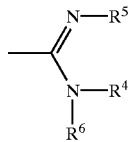

(II)

(wherein $R^4$, $R^5$, and $R^6$ have the same meanings as defined above).

As examples of substituents on $Ar^2$ in the compounds (III), halogen includes fluoro, chloro, bromo, and iodo; acylamino group having 1 to 9 carbon atoms includes —$NHCOCH_3$ and —NHCOPh; alkylamino group having 1 to 8 carbon atoms includes methylamino, ethylamino, n-propylamino, isopropylamino, and cyclohexylamino; arylamino group having 6 to 15 carbon atoms includes phenylamino; dialkylamino group having 2 to 16 carbon atoms includes dimethylamino, diethylamino, di(n-propyl)amino, diisopropylamino, and di(cyclohexyl)amino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —$SO_2NH_2$, —$SO_2NHMe$, —$SO_2NMe_2$, —$SO_2NHPh$, and —$SO_2NPh_2$; alkoxycarbonyl group having 1 to 9 carbon atoms includes —COOMe, and —COOEt; aminocarbonyl group having 1 to 15 carbon atoms includes —$CONH_2$, —CONHMe, —$CONMe_2$, —CONH$^t$Bu, —CONHPh, and —$CONPh_2$; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Of these substituents, identical or different one or two fluoro, chloro, bromo, nitro, —$NHCOCH_3$, —NHCOPh, amino, methylamino, ethylamino, n-propylamino, isopropylamino, phenylamino, dimethylamino, diethylamino, di(n-propyl)amino, diisopropylamino, hydroxy, methoxy, ethoxy, n-propoxy, isopropoxy, phenoxy, trifluoromethyl, trifluoromethoxy, 2,2,2-trifluoroethoxy, cyano, —$SO_2NH_2$, —$SO_2NHMe$, —SO$_2$NMe$_2$, —SO$_2$NHPh, —CONH$_2$, —CONHMe, —CONMe$_2$, —CONH$^t$Bu, methylthio, ethylthio, and phenylthio are preferred. Among them, identical or different one or two fluoro, chloro, bromo, nitro, —NHCOCH$_3$, amino, methylamino, isopropylamino, phenylamino, dimethylamino, diisopropylamino, hydroxy, methoxy, ethoxy, isopropoxy, trifluoromethyl, trifluoromethoxy, cyano, —SO$_2$NH$_2$, —SO$_2$NHMe, —SO$_2$NMe$_2$, —SO$_2$NHPh, —CONH$_2$, —CONMe$_2$, methylthio, and phenylthio are more preferred, of which identical or different one or two fluoro, chloro, bromo, nitro, amino, methylamino, 2-phenylethylamino, methoxy, ethoxy, trifluoromethyl, trifluoromethoxy, —SO$_2$NH$_2$, and —CONH$_2$ are especially preferred.

As examples of substituents on D, halogen includes fluoro, chloro, and bromo; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; haloalkyl group having 1 to 8 carbon atoms includes trifluoromethyl and 2,2,2-trifluoroethyl; aminosulfonyl group having 0 to 15 carbon atoms includes —SO$_2$NH$_2$, —SO$_2$NHMe, —SO$_2$NMe$_2$, —SO$_2$NHPh, and —SO$_2$NPh$_2$; alkoxycarbonyl group having 2 to 9 carbon atoms includes —COOMe and —COOEt; aminocarbonyl group having 1 to 15 carbon atoms. includes —CONH$_2$, —CONHMe, —CONMe$_2$, —CONH$^t$Bu, —CONHPh, and —CONPh$_2$; hydroxyalkyl group having 1 to 8 carbon atoms includes hydroxymethyl, 1-hydroxyethyl, 2-hydroxyethyl, and 3-hydroxypropyl; alkylcarbonyl group having 2 to 9 carbon atoms includes —COMe, and —COEt; arylcarbonyl having 7 to 16 carbon atoms includes —COPh, naphthylcarbonyl, and 2-furanylcarbonyl; aralkyl having 7 to 15 carbon atoms includes benzyl, 2-phenylethyl, and 3-phenylpropyl; and other substituents include hydroxy and —COOH. Among these substituents, identical or different one or two fluoro, —NHCOCH$_3$, —NHCOPh, hydroxy, methyl, isopropyl, t-butyl, phenyl, trifluoromethyl, trifluoromethoxy, —SO$_2$NH$_2$, —SO$_2$NHMe, —SO$_2$NMe$_2$, —SO$_2$NHPh, —SO$_2$NPh$_2$, —COOH, —COOMe, —CONH$_2$, —CONHMe, —CONMe$_2$, —CONH$^t$Bu, —CONHPh, and —CONPh$_2$ are preferred. Among them, identical or different one or two fluoro, hydroxy, methyl, isopropyl, phenyl, trifluoromethyl, —SO$_2$NH$_2$, —SO$_2$NHMe, —SO$_2$NHPh, —COOH, —COOMe, —CONH$_2$, —CONHMe, —CONH$^t$Bu, and —CONMe$_2$ are more preferred, of which one fluoro, hydroxy, methyl, phenyl, trifluoromethyl, —SO$_2$NH$_2$, —CONH$_2$, and —CONH$^t$Bu are especially preferred.

In A, alkylene having 3 to 8 carbon atoms includes 1,3-trimethylene, 1,4-butylene, 1,5-pentamethylene, 1,6-hexamethylene, and 1,7-heptamethylene; phenylene includes 1,4-phenylene and 1,3-phenylene; cycloalkylene having 3 to 8 carbon atoms includes 1,2-cyclopentylene, 1,3-cyclopentylene, 1,2-cyclohexylene, 1,3-cyclohexylene, 1,4-cyclohexylene, and 1,5-cyclooctylene. Among these groups, 1,3-trimethylene, 1,4-butylene, 1,5-pentamethylene, 1,6-hexamethylene, 1,4-phenylene, 1,2-cyclohexylene, 1,3-cyclohexylene, 1,4-cyclohexylene, and 1,5-cyclooctylene are preferred, of which 1,3-trimethylene, 1,4-butylene, 1,5-pentamethylene, and 1,4-cyclohexylene are especially preferred.

As examples of substituents on the alkylene having 3 to 8 carbon atoms, phenylene, or cycloalkylene having 3 to 8 carbon atoms in A, halogen includes fluoro, chloro, bromo, and iodo; acylamino group having 1 to 9 carbon atoms includes —NHCOCH$_3$ and —NHCOPh; alkylamino group having 1 to 8 carbon atoms includes methylamino, ethylamino, n-propylamino, isopropylamino, and cyclohexylamino; arylamino group having 6 to 15 carbon atoms includes phenylamino; dialkylamino group having 2 to 16 carbon atoms includes dimethylamino, diethylamino, di(n-propyl)amino, diisopropylamino, di(cyclohexyl)amino, piperidino, and pyrrolidino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —SO$_2$NH$_2$, —SO$_2$NHMe, —SO$_2$NMe$_2$, —SO$_2$NHPh, and —SO$_2$NPh$_2$; alkoxycarbonyl group having 2 to 9 carbon atoms includes —COOMe and —COOEt; aminocarbonyl group having 1 to 15 carbon atoms includes —CONH$_2$, —CONHMe, —CONMe$_2$, —CONH$^t$Bu, —CONHPh, and —CONPh$_2$; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Among these substituents, identical or different one or more fluoro, chloro, amino, methylamino, is6propylamino, phenylamino, dimethylamino, 1-piperidino, 1-pyrrolidino, hydroxy, methyl, isopropyl, phenyl, methoxy, isopropoxy, phenoxy, trifluoromethyl, trifluoromethoxy, cyano, —SO$_2$NH$_2$, —SO$_2$NHMe, —SO$_2$NMe$_2$, —SO$_2$NHPh, —SO$_2$NPh$_2$, —COOH, —COOMe, —CONH$_2$, —CONHMe, —CONMe$_2$, —CONH$^t$Bu, —CONHPh, and —CONPh$_2$ are preferred, of which identical or different one or more fluoro, amino, methylamino, 1-piperidino, hydroxy, methyl, isopropyl, methoxy, and trifluoromethyl are especially preferred.

Of $R^2$, $R^3$, $R^4$, $R^5$, and $R^6$ in $Q^2$, alkyl having 1 to 6 carbon atoms includes methyl, n-propyl, isopropyl, n-butyl, isobutyl, sec-butyl, t-butyl, n-pentyl, isopentyl, neopentyl, and n-hexyl; cycloalkyl having 3 to 8 carbon atoms includes cyclopropyl, cyclobutyl, cyclohexyl, and cycloheptyl; aryl having 6 to 15 carbon atoms includes phenyl, naphthyl, and biphenyl; aralkyl having 7 to 15 carbon atoms includes benzyl, 2-phenylethyl, 3-phenylpropyl, 2-phenylpropyl, and 4-phenylbutyl; alkenyl having 2 to 9 carbon atoms includes ethenyl, 2-propenyl, 2-pentenyl, 2-octenyl, 3-butenyl, 3-hexenyl, 4-pentenyl, 4-octenyl, 1, 3-butadienyl, 1,3-pentadienyl, 2,4-pentadienyl, 1,3,5-hexatrienyl, 1,3,5-heptatrienyl, and 2,4,6-heptatrienyl (these also include isomers (E form and Z form) with respect to double bond). Of these groups, methyl, n-propyl, cyclopropyl, benzyl, 2-phenylethyl, 3-phenylpropyl, 2-phenylpropyl, 4-phenylbutyl, and 2-propenyl are preferred. Among them, methyl, cyclopropyl, benzyl, 2-phenylethyl, 3-phenylpropyl, 2-phenylpropyl, 4phenylbutyl, and 2-propenyl are more preferred, of which methyl, benzyl, 2-phenylethyl, 3-phenylpropyl, and 2-propenyl are especially preferred.

When $R^2$, $R^3$, $R^4$, $R^5$, and $R^6$ are aryl having 6 to 15 carbon atoms or,aralkyl having 7 to 15 carbon atoms, as examples of substituents on the aryl, halogen includes, fluoro, chloro, and bromo; acylamino group having 1 to 9 carbon atoms includes —NHCOCH₃ and —NHCOPh; alkylamino group having 1 to 8 carbon atoms includes methylamino, ethylamino, n-propylamino, isopropylamino, and cyclohexylamino; arylamino grouphaving 6 to 15 carbon atoms includes phenylamino; dialkylamino group having 2 to 16 carbon atoms includes dimethylamino, diethylamino, di(n-propyl)amino, diisopropylamino, di(cyclohexyl)amino, piperidino, and pyrrolidino; diarylamino group having 12 to 20 carbon atoms includes diphenylamino; alkyl group having 1 to 8 carbon atoms includes methyl, ethyl, n-propyl, isopropyl, n-butyl, isobutyl, sec-butyl, t-butyl, n-pentyl, isopentyl, neopentyl, n-hexyl, and cyclohexyl; aryl group having 6 to 15 carbon atoms includes phenyl, naphthyl, and biphenyl; alkoxy group having 1 to 8 carbon atoms includes methoxy, ethoxy, n-propoxy, isopropoxy, and cyclohexyloxy; aryloxy group having 6 to 15 carbon atoms includes phenoxy; haloalkyl group having 1 to 8 carbon atoms includes trifluoromethyl and 2,2,2-trifluoroethyl; haloalkoxy group having 1 to 8 carbon atoms includes trifluoromethoxy and 2,2,2-trifluoroethoxy; aminosulfonyl group having 0 to 15 carbon atoms includes —SO₂NH₂, —SO₂NHMe, —SO₂NMe₂, —SO₂NHPh, and —SO₂NPh₂; alkoxycarbonyl group having 2 to 9 carbon atoms includes —COOMe and —COOEt; aminocarbonyl group having 1 to 15 carbon atoms includes —CONH₂, —CONHMe, —CONMe₂, —CONHʹBu, —CONHPh, and —CONPh₂; alkylthio group having 1 to 8 carbon atoms includes methylthio, ethylthio, n-propylthio, and isopropylthio; arylthio group having 6 to 15 carbon atoms includes phenylthio; and other substituents include nitro, amino, hydroxy, cyano, and —COOH. Among these substituents, identical or different one or more fluoro, chloro, amino, methylamino, isopropylamino, phenylamino, dimethylamino, 1-piperidino, 1-pyrrolidino, hydroxy, methyl, isopropyl, phenyl, methoxy, isopropoxy, phenoxy, trifluoromethyl, trifluoromethoxy, cyano, —SO₂NH₂, —SO₂NHMe, —SO₂NMe₂, —SO₂NHPh, —SO₂NPh₂, —COOH, —COOMe, —CONH₂, —CONHMe, —CONMe₂, —CONHʹBu, —CONHPh, and —CONPh₂ are preferred, of which identical or different one or more fluoro, amino, methylamino, 1-piperidino, hydroxy, methyl, phenyl, isopropyl, methoxy, trifluoromethyl, —SO₂NH₂, and —CONH₂ are especially preferred.

As Q², methylamine, 2-phenylethylamine, piperidine, pyrrolidine, 1,3,4-trihydroisoquinoline, dimethylamine, di(2-phenylethyl)amine, isoindoline, piperazine, morpholine, 2-piperidone, 1-guanidine, and 2-imidazoline are preferred. Among them, 2-phenylethylamine, piperidine, 1,3,4-trihydroisoquinoline, dimethylamine, di(2-phenylethyl)amine, isoindoline, and 2-imidazoline are more preferred, of which 2-phenylethylamine, piperidine, 1,3,4-trihydroisoquinoline, isoindoline, and 2-imidazoline are especially preferred.

Pharmacologically preferable acid addition salts include, but are not limited to, hydrochlorides, sulfates, nitrates, hydrobromides, hydroiodides, phosphates, and other inorganic acid salts; acetates, lactates, citrates, oxalates, glutarates, malates, tartrates, fumarates, mandelates, maleates, benzoates, phthalates, and other organic carboxylates; methanesulfonates, ethanesulfonates, benzenesulfonates, p-toluenesulfonates, camphorsulfonates, and other organic sulfonates. Among them, hydrochlorides, phosphates, tartrates, and methanesulfonates are especially preferred.

Specific examples of the compounds represented by the general formula (I) or general formula (III) according to the invention are shown in the following tables, which are not intended to limit the scope of the present invention.

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |

-continued

| | | | |
|---|---|---|---|
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

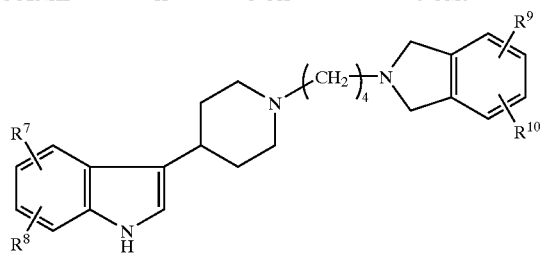

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |

-continued

| | | | |
|---|---|---|---|
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

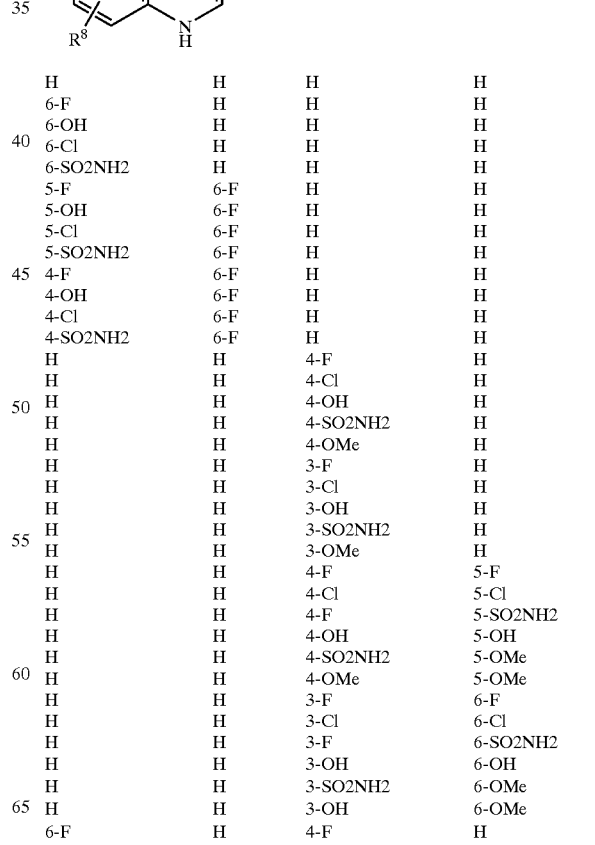

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |

| | | | |
|---|---|---|---|
| 6-F | H | 4-Cl | H |
| 6-F | H | 4-OH | H |
| 6-F | H | 4-SO2NH2 | H |
| 6-F | H | 4-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

Structure with R7, R8 on indole-piperidine and R9, R10 on tetrahydroisoquinoline, connected by -(CH2)3-.

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-Cl | 6-F |
| 6-F | H | 3-Cl | 6-F |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 3-F | 5-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-F | 6-F |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 3-F | 5-F |
| 6-SO2NH2 | H | 4-F | 6-F |
| 6-SO2NH2 | H | 3-Cl | 4-Cl |
| 6-SO2NH2 | H | 3-Cl | 5-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |

-continued

| | | | |
|---|---|---|---|
| 6-F | H | 5-SO2NH2 | H |
| 6-F | H | 5-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-F | 6-F |
| 6-F | H | 3-Cl | 6-Cl |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 3-F | 5-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-F | 6-F |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 4-F | 6-F |
| 6-SO2NH2 | H | 3-Cl | 4-Cl |
| 6-SO2NH2 | H | 3-Cl | 5-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |

-continued

| R7 | R8 | R9 | R10 |
|---|---|---|---|
| 6-F | H | 5-OMe | H |
| 6-F | H | 5-Cl | H |
| 6-F | H | 5-F | H |
| 6-F | H | 5-OH | H |
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-F | 6-F |
| 6-F | H | 3-Cl | 6-Cl |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-F | 6-F |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 3-F | 5-F |
| 6-SO2NH2 | H | 4-F | 6-F |
| 6-SO2NH2 | H | 3-Cl | 4-Cl |
| 6-SO2NH2 | H | 3-Cl | 5-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OMe | H |

-continued

| R7 | R8 | R9 | R10 |
|---|---|---|---|
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

[Structure: indole-R7/R8 connected via piperidine-(CH2)3-NH-CH2CH2-phenyl-R9/R10]

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |
| 6-F | H | 2-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-F | 6-F |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-Cl | 4-Cl |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |

-continued

[Structure: indole (R7, R8) - piperidine - (CH2)4 - NH - phenyl (R9, R10)]

| R8 | R7 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |
| 6-F | H | 2-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-Cl | 4-Cl |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |

[Structure: indole (R7, R8) - piperidine - (CH2)5 - NH - phenyl (R9, R10)]

| R8 | R7 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |
| 6-F | H | 2-OMe | H |
| 6-F | H | 3-F | H |

-continued

| | | | |
|---|---|---|---|
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-F | 6-F |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-Cl | 4-Cl |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |

-continued $$\text{R}^7\text{-indole-piperazine-}(CH_2)_3\text{-N-isoindoline-R}^9,\text{R}^{10}$$

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |

-continued

| | | | |
|---|---|---|---|
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

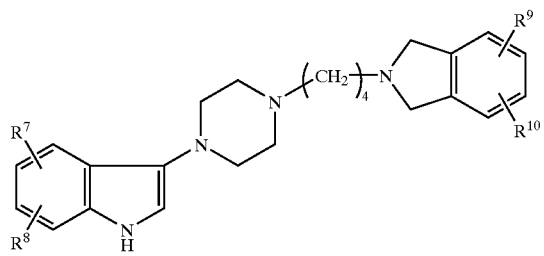

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

(second structure: piperazine-indole with -(CH2)5- linker to isoindoline)

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |

| | | | |
|---|---|---|---|
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | 5-F |
| 6-F | H | 4-Cl | 5-Cl |
| 6-F | H | 4-F | 5-SO2NH2 |
| 6-F | H | 4-OH | 5-OH |
| 6-F | H | 4-SO2NH2 | 5-OMe |
| 6-F | H | 4-OMe | 5-OMe |
| 6-F | H | 3-F | 6-F |
| 6-F | H | 3-Cl | 6-Cl |
| 6-F | H | 3-F | 6-SO2NH2 |
| 6-F | H | 3-OH | 6-OH |
| 6-F | H | 3-SO2NH2 | 6-OMe |
| 6-F | H | 3-OH | 6-OMe |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | 5-F |
| 6-SO2NH2 | H | 4-Cl | 5-Cl |
| 6-SO2NH2 | H | 4-F | 5-SO2NH2 |
| 6-SO2NH2 | H | 4-OH | 5-OH |
| 6-SO2NH2 | H | 4-SO2NH2 | 5-OMe |
| 6-SO2NH2 | H | 4-OMe | 5-OMe |
| 6-SO2NH2 | H | 3-F | 6-F |
| 6-SO2NH2 | H | 3-Cl | 6-Cl |
| 6-SO2NH2 | H | 3-F | 6-SO2NH2 |
| 6-SO2NH2 | H | 3-OH | 6-OH |
| 6-SO2NH2 | H | 3-SO2NH2 | 6-OMe |
| 6-SO2NH2 | H | 3-OH | 6-OMe |

[Structure: indole-piperazine-(CH2)3-tetrahydroisoquinoline with substituents R7, R8 on indole and R9, R10 on tetrahydroisoquinoline]

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-Cl | 6-F |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 3-F | 5-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 3-F | 5-F |
| 6-SO2NH2 | H | 4-F | 6-F |
| 6-SO2NH2 | H | 3-Cl | 4-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OMe | H |
| 6-F | H | 5-F | H |
| 6-F | H | 5-Cl | H |

-continued

| | | | |
|---|---|---|---|
| 6-F | H | 5-F | H |
| 6-F | H | 5-OH | H |
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-F | 6-F |
| 6-F | H | 3-Cl | 6-Cl |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 3-F | 5-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-F | 6-F |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 3-F | 5-F |
| 6-SO2NH2 | H | 4-F | 6-F |
| 6-SO2NH2 | H | 3-Cl | 4-Cl |
| 6-SO2NH2 | H | 3-Cl | 5-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OMe | H |
| 6-F | H | 5-F | H |
| 6-F | H | 5-Cl | H |
| 6-F | H | 5-F | H |

-continued

| R7 | R8 | R9 | R10 |
|---|---|---|---|
| 6-F | H | 5-OH | H |
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 6-F | H | 4-F | 5-F |
| 6-F | H | 4-Cl | 5-Cl |
| 6-F | H | 4-OH | 5-OH |
| 6-F | H | 4-OMe | 5-OMe |
| 6-F | H | 4-OMe | 5-SO2NH2 |
| 6-F | H | 4-SO2NH2 | 5-OMe |
| 6-F | H | 3-F | 6-F |
| 6-F | H | 3-Cl | 6-Cl |
| 6-F | H | 3-OH | 6-OH |
| 6-F | H | 3-OMe | 6-OMe |
| 6-F | H | 3-OMe | 6-SO2NH2 |
| 6-F | H | 3-SO2NH2 | 6-OMe |
| 6-F | H | 3-F | 4-F |
| 6-F | H | 4-F | 6-F |
| 6-F | H | 3-Cl | 4-Cl |
| 6-F | H | 3-Cl | 5-Cl |
| 6-F | H | 4-Cl | 6-Cl |
| 6-F | H | 3-OH | 4-OH |
| 6-F | H | 3-OH | 5-OH |
| 6-F | H | 4-OH | 6-OH |
| 6-F | H | 3-OMe | 4-OMe |
| 6-F | H | 3-OMe | 5-OMe |
| 6-F | H | 4-OMe | 6-OMe |
| 6-SO2NH2 | H | 4-F | 5-F |
| 6-SO2NH2 | H | 4-Cl | 5-Cl |
| 6-SO2NH2 | H | 4-OH | 5-OH |
| 6-SO2NH2 | H | 4-OMe | 5-OMe |
| 6-SO2NH2 | H | 4-OMe | 5-SO2NH2 |
| 6-SO2NH2 | H | 4-SO2NH2 | 5-OMe |
| 6-SO2NH2 | H | 3-F | 6-F |
| 6-SO2NH2 | H | 3-Cl | 6-Cl |
| 6-SO2NH2 | H | 3-OH | 6-OH |
| 6-SO2NH2 | H | 3-OMe | 6-OMe |
| 6-SO2NH2 | H | 3-OMe | 6-SO2NH2 |
| 6-SO2NH2 | H | 3-SO2NH2 | 6-OMe |
| 6-SO2NH2 | H | 3-F | 4-F |
| 6-SO2NH2 | H | 3-F | 5-F |
| 6-SO2NH2 | H | 4-F | 6-F |
| 6-SO2NH2 | H | 3-Cl | 4-Cl |
| 6-SO2NH2 | H | 3-Cl | 5-Cl |
| 6-SO2NH2 | H | 4-Cl | 6-Cl |
| 6-SO2NH2 | H | 3-OH | 4-OH |
| 6-SO2NH2 | H | 3-OH | 5-OH |
| 6-SO2NH2 | H | 4-OH | 6-OH |
| 6-SO2NH2 | H | 3-OMe | 4-OMe |
| 6-SO2NH2 | H | 3-OMe | 5-OMe |
| 6-SO2NH2 | H | 4-OMe | 6-OMe |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-F | H | 5-F | H |
| 6-F | H | 5-Cl | H |
| 6-F | H | 5-F | H |
| 6-F | H | 5-OH | H |
| 6-F | H | 5-SO2NH2 | H |
| 6-F | H | 5-OMe | H |
| 6-F | H | 5-F | H |
| 6-F | H | 5-Cl | H |
| 6-F | H | 5-F | H |
| 6-F | H | 5-OH | H |

-continued

| | | | |
|---|---|---|---|
| 6-F | H | 5-SO2NH2 | H |
| 6-F | H | 5-OH | H |
| 6-F | H | 6-F | H |
| 6-F | H | 6-Cl | H |
| 6-F | H | 6-F | H |
| 6-F | H | 6-OH | H |
| 6-F | H | 6-SO2NH2 | H |
| 6-F | H | 6-OH | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OMe | H |
| 6-SO2NH2 | H | 5-F | H |
| 6-SO2NH2 | H | 5-Cl | H |
| 6-SO2NH2 | H | 5-F | H |
| 6-SO2NH2 | H | 5-OH | H |
| 6-SO2NH2 | H | 5-SO2NH2 | H |
| 6-SO2NH2 | H | 5-OH | H |
| 6-SO2NH2 | H | 6-F | H |
| 6-SO2NH2 | H | 6-Cl | H |
| 6-SO2NH2 | H | 6-F | H |
| 6-SO2NH2 | H | 6-OH | H |
| 6-SO2NH2 | H | 6-SO2NH2 | H |
| 6-SO2NH2 | H | 6-OH | H |

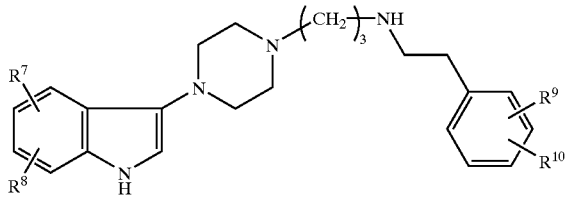

| | | | |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |

-continued

| | | | |
|---|---|---|---|
| 6-F | H | 2-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-F | 6-F |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |

-continued

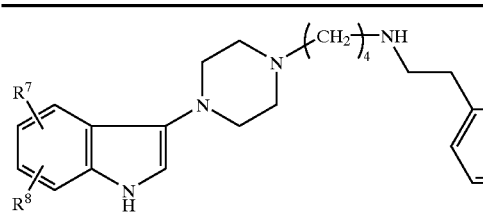

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |
| 6-F | H | 2-OMe | H |
| 6-F | H | 3-F | H |
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-F | 6-F |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-Cl | 4-Cl |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |

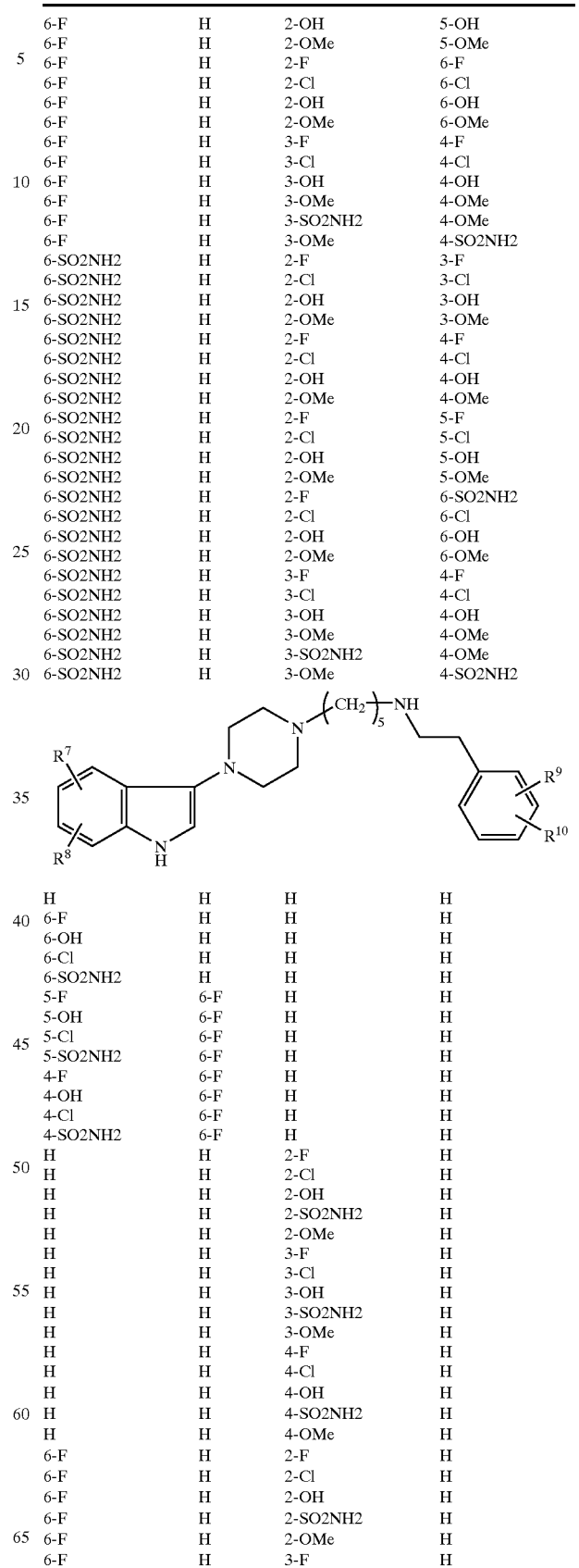

| R7 | R8 | R9 | R10 |
|---|---|---|---|
| H | H | H | H |
| 6-F | H | H | H |
| 6-OH | H | H | H |
| 6-Cl | H | H | H |
| 6-SO2NH2 | H | H | H |
| 5-F | 6-F | H | H |
| 5-OH | 6-F | H | H |
| 5-Cl | 6-F | H | H |
| 5-SO2NH2 | 6-F | H | H |
| 4-F | 6-F | H | H |
| 4-OH | 6-F | H | H |
| 4-Cl | 6-F | H | H |
| 4-SO2NH2 | 6-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 6-F | H | 2-F | H |
| 6-F | H | 2-Cl | H |
| 6-F | H | 2-OH | H |
| 6-F | H | 2-SO2NH2 | H |
| 6-F | H | 2-OMe | H |
| 6-F | H | 3-F | H |

-continued

| | | | |
|---|---|---|---|
| 6-F | H | 3-Cl | H |
| 6-F | H | 3-OH | H |
| 6-F | H | 3-SO2NH2 | H |
| 6-F | H | 3-OMe | H |
| 6-F | H | 4-F | H |
| 6-F | H | 4-Cl | H |
| 6-F | H | 4-OH | H |
| 6-F | H | 4-SO2NH2 | H |
| 6-F | H | 4-OMe | H |
| 6-SO2NH2 | H | 2-F | H |
| 6-SO2NH2 | H | 2-Cl | H |
| 6-SO2NH2 | H | 2-OH | H |
| 6-SO2NH2 | H | 2-SO2NH2 | H |
| 6-SO2NH2 | H | 2-OMe | H |
| 6-SO2NH2 | H | 3-F | H |
| 6-SO2NH2 | H | 3-Cl | H |
| 6-SO2NH2 | H | 3-OH | H |
| 6-SO2NH2 | H | 3-SO2NH2 | H |
| 6-SO2NH2 | H | 3-OMe | H |
| 6-SO2NH2 | H | 4-F | H |
| 6-SO2NH2 | H | 4-Cl | H |
| 6-SO2NH2 | H | 4-OH | H |
| 6-SO2NH2 | H | 4-SO2NH2 | H |
| 6-SO2NH2 | H | 4-OMe | H |
| 6-F | H | 2-F | 3-F |
| 6-F | H | 2-Cl | 3-Cl |
| 6-F | H | 2-OH | 3-OH |
| 6-F | H | 2-OMe | 3-OMe |
| 6-F | H | 2-F | 4-F |
| 6-F | H | 2-Cl | 4-Cl |
| 6-F | H | 2-OH | 4-OH |
| 6-F | H | 2-OMe | 4-OMe |
| 6-F | H | 2-F | 5-F |
| 6-F | H | 2-Cl | 5-Cl |
| 6-F | H | 2-OH | 5-OH |
| 6-F | H | 2-OMe | 5-OMe |
| 6-F | H | 2-F | 6-F |
| 6-F | H | 2-Cl | 6-Cl |
| 6-F | H | 2-OH | 6-OH |
| 6-F | H | 2-OMe | 6-OMe |
| 6-F | H | 3-F | 4-F |
| 6-F | H | 3-Cl | 4-Cl |
| 6-F | H | 3-OH | 4-OH |
| 6-F | H | 3-OMe | 4-OMe |
| 6-F | H | 3-SO2NH2 | 4-OMe |
| 6-F | H | 3-OMe | 4-SO2NH2 |
| 6-SO2NH2 | H | 2-F | 3-F |
| 6-SO2NH2 | H | 2-Cl | 3-Cl |
| 6-SO2NH2 | H | 2-OH | 3-OH |
| 6-SO2NH2 | H | 2-OMe | 3-OMe |
| 6-SO2NH2 | H | 2-F | 4-F |
| 6-SO2NH2 | H | 2-Cl | 4-Cl |
| 6-SO2NH2 | H | 2-OH | 4-OH |
| 6-SO2NH2 | H | 2-OMe | 4-OMe |
| 6-SO2NH2 | H | 2-F | 5-F |
| 6-SO2NH2 | H | 2-Cl | 5-Cl |
| 6-SO2NH2 | H | 2-OH | 5-OH |
| 6-SO2NH2 | H | 2-OMe | 5-OMe |
| 6-SO2NH2 | H | 2-F | 6-SO2NH2 |
| 6-SO2NH2 | H | 2-Cl | 6-Cl |
| 6-SO2NH2 | H | 2-OH | 6-OH |
| 6-SO2NH2 | H | 2-OMe | 6-OMe |
| 6-SO2NH2 | H | 3-F | 4-F |
| 6-SO2NH2 | H | 3-Cl | 4-Cl |
| 6-SO2NH2 | H | 3-OH | 4-OH |
| 6-SO2NH2 | H | 3-OMe | 4-OMe |
| 6-SO2NH2 | H | 3-SO2NH2 | 4-OMe |
| 6-SO2NH2 | H | 3-OMe | 4-SO2NH2 |
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | 5-F |
| 7-F | H | 4-Cl | 5-Cl |
| 7-F | H | 4-F | 5-SO2NH2 |
| 7-F | H | 4-OH | 5-OH |
| 7-F | H | 4-SO2NH2 | 5-OMe |
| 7-F | H | 4-OMe | 5-OMe |
| 7-F | H | 3-F | 6-F |
| 7-F | H | 3-Cl | 6-Cl |
| 7-F | H | 3-F | 6-SO2NH2 |
| 7-F | H | 3-OH | 6-OH |
| 7-F | H | 3-SO2NH2 | 6-OMe |
| 7-F | H | 3-OH | 6-OMe |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | 5-F |
| 7-SO2NH2 | H | 4-Cl | 5-Cl |
| 7-SO2NH2 | H | 4-F | 5-SO2NH2 |
| 7-SO2NH2 | H | 4-OH | 5-OH |
| 7-SO2NH2 | H | 4-SO2NH2 | 5-OMe |
| 7-SO2NH2 | H | 4-OMe | 5-OMe |
| 7-SO2NH2 | H | 3-F | 6-F |
| 7-SO2NH2 | H | 3-Cl | 6-Cl |
| 7-SO2NH2 | H | 3-F | 6-SO2NH2 |
| 7-SO2NH2 | H | 3-OH | 6-OH |
| 7-SO2NH2 | H | 3-SO2NH2 | 6-OMe |

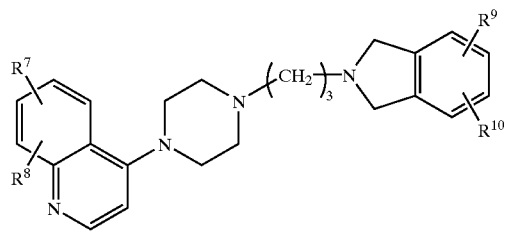

-continued

| | | | |
|---|---|---|---|
| 7-SO2NH2 | H | 3-OH | 6-OMe |

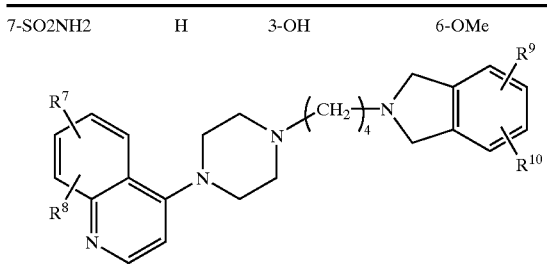

| R7 | R8 | R9 | R10 |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | 5-F |
| 7-F | H | 4-Cl | 5-Cl |
| 7-F | H | 4-F | 5-SO2NH2 |
| 7-F | H | 4-OH | 5-OH |
| 7-F | H | 4-SO2NH2 | 5-OMe |
| 7-F | H | 4-OMe | 5-OMe |
| 7-F | H | 3-F | 6-F |
| 7-F | H | 3-Cl | 6-Cl |
| 7-F | H | 3-F | 6-SO2NH2 |
| 7-F | H | 3-OH | 6-OH |
| 7-F | H | 3-SO2NH2 | 6-OMe |
| 7-F | H | 3-OH | 6-OMe |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |

-continued

| | | | |
|---|---|---|---|
| 7-SO2NH2 | H | 3-OMe | H |
| 7-SO2NH2 | H | 4-F | 5-F |
| 7-SO2NH2 | H | 4-Cl | 5-Cl |
| 7-SO2NH2 | H | 4-F | 5-SO2NH2 |
| 7-SO2NH2 | H | 4-OH | 5-OH |
| 7-SO2NH2 | H | 4-SO2NH2 | 5-OMe |
| 7-SO2NH2 | H | 4-OMe | 5-OMe |
| 7-SO2NH2 | H | 3-F | 6-F |
| 7-SO2NH2 | H | 3-Cl | 6-Cl |
| 7-SO2NH2 | H | 3-F | 6-SO2NH2 |
| 7-SO2NH2 | H | 3-OH | 6-OH |
| 7-SO2NH2 | H | 3-SO2NH2 | 6-OMe |
| 7-SO2NH2 | H | 3-OH | 6-OMe |

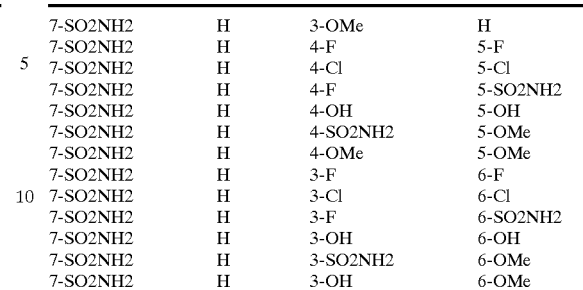

| R7 | R8 | R9 | R10 |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 4-F | H |
| H | H | 4-Cl | H |
| H | H | 4-OH | H |
| H | H | 4-SO2NH2 | H |
| H | H | 4-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | 5-F |
| H | H | 4-Cl | 5-Cl |
| H | H | 4-F | 5-SO2NH2 |
| H | H | 4-OH | 5-OH |
| H | H | 4-SO2NH2 | 5-OMe |
| H | H | 4-OMe | 5-OMe |
| H | H | 3-F | 6-F |
| H | H | 3-Cl | 6-Cl |
| H | H | 3-F | 6-SO2NH2 |
| H | H | 3-OH | 6-OH |
| H | H | 3-SO2NH2 | 6-OMe |
| H | H | 3-OH | 6-OMe |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | 5-F |
| 7-F | H | 4-Cl | 5-Cl |
| 7-F | H | 4-F | 5-SO2NH2 |
| 7-F | H | 4-OH | 5-OH |
| 7-F | H | 4-SO2NH2 | 5-OMe |
| 7-F | H | 4-OMe | 5-OMe |
| 7-F | H | 3-F | 6-F |
| 7-F | H | 3-Cl | 6-Cl |
| 7-F | H | 3-F | 6-SO2NH2 |

| | | | |
|---|---|---|---|
| 7-F | H | 3-OH | 6-OH |
| 7-F | H | 3-SO2NH2 | 6-OMe |
| 7-F | H | 3-OH | 6-OMe |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | 5-F |
| 7-SO2NH2 | H | 4-Cl | 5-Cl |
| 7-SO2NH2 | H | 4-F | 5-SO2NH2 |
| 7-SO2NH2 | H | 4-OH | 5-OH |
| 7-SO2NH2 | H | 4-SO2NH2 | 5-OMe |
| 7-SO2NH2 | H | 4-OMe | 5-OMe |
| 7-SO2NH2 | H | 3-F | 6-F |
| 7-SO2NH2 | H | 3-Cl | 6-Cl |
| 7-SO2NH2 | H | 3-F | 6-SO2NH2 |
| 7-SO2NH2 | H | 3-OH | 6-OH |
| 7-SO2NH2 | H | 3-SO2NH2 | 6-OMe |
| 7-SO2NH2 | H | 3-OH | 6-OMe |

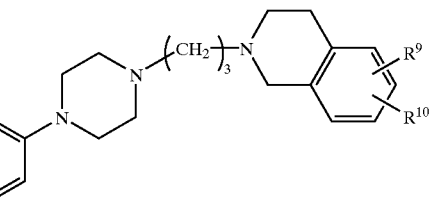

| | | | |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 7-F | H | 4-F | 5-F |
| 7-F | H | 4-Cl | 5-Cl |
| 7-F | H | 4-OH | 5-OH |
| 7-F | H | 4-OMe | 5-OMe |
| 7-F | H | 4-SO2NH2 | 5-OMe |
| 7-F | H | 3-F | 6-F |
| 7-F | H | 3-Cl | 6-Cl |
| 7-F | H | 3-OH | 6-OH |
| 7-F | H | 3-OMe | 6-OMe |
| 7-F | H | 3-OMe | 6-SO2NH2 |
| 7-F | H | 3-SO2NH2 | 6-OMe |
| 7-F | H | 3-F | 4-F |
| 7-F | H | 3-F | 5-F |
| 7-F | H | 4-F | 6-F |
| 7-F | H | 3-Cl | 4-Cl |
| 7-F | H | 3-Cl | 5-Cl |
| 7-F | H | 4-Cl | 6-Cl |
| 7-F | H | 3-OH | 4-OH |
| 7-F | H | 3-OH | 5-OH |
| 7-F | H | 4-OH | 6-OH |
| 7-F | H | 3-OMe | 4-OMe |
| 7-F | H | 3-OMe | 5-OMe |
| 7-F | H | 4-OMe | 6-OMe |
| 7-SO2NH2 | H | 4-F | 5-F |
| 7-SO2NH2 | H | 4-Cl | 5-Cl |
| 7-SO2NH2 | H | 4-OH | 5-OH |
| 7-SO2NH2 | H | 4-OMe | 5-OMe |
| 7-SO2NH2 | H | 4-SO2NH2 | 5-SO2NH2 |
| 7-SO2NH2 | H | 4-SO2NH2 | 5-OMe |
| 7-SO2NH2 | H | 3-F | 6-F |
| 7-SO2NH2 | H | 3-Cl | 6-Cl |
| 7-SO2NH2 | H | 3-OH | 6-OH |
| 7-SO2NH2 | H | 3-OMe | 6-OMe |
| 7-SO2NH2 | H | 3-OMe | 6-SO2NH2 |
| 7-SO2NH2 | H | 3-SO2NH2 | 6-OMe |
| 7-SO2NH2 | H | 3-F | 4-F |
| 7-SO2NH2 | H | 3-F | 5-F |
| 7-SO2NH2 | H | 4-F | 6-F |
| 7-SO2NH2 | H | 3-Cl | 4-Cl |
| 7-SO2NH2 | H | 3-Cl | 5-Cl |
| 7-SO2NH2 | H | 4-Cl | 6-Cl |
| 7-SO2NH2 | H | 3-OH | 4-OH |
| 7-SO2NH2 | H | 3-OH | 5-OH |
| 7-SO2NH2 | H | 4-OH | 6-OH |
| 7-SO2NH2 | H | 3-OMe | 4-OMe |
| 7-SO2NH2 | H | 3-OMe | 5-OMe |
| 7-SO2NH2 | H | 4-OMe | 6-OMe |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OH | H |
| 7-F | H | 6-F | H |
| 7-F | H | 6-Cl | H |
| 7-F | H | 6-F | H |
| 7-F | H | 6-OH | H |
| 7-F | H | 6-SO2NH2 | H |
| 7-F | H | 6-OH | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |

-continued

| | | | |
|---|---|---|---|
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OH | H |
| 7-SO2NH2 | H | 6-F | H |
| 7-SO2NH2 | H | 6-Cl | H |
| 7-SO2NH2 | H | 6-F | H |
| 7-SO2NH2 | H | 6-OH | H |
| 7-SO2NH2 | H | 6-SO2NH2 | H |
| 7-SO2NH2 | H | 6-OH | H |

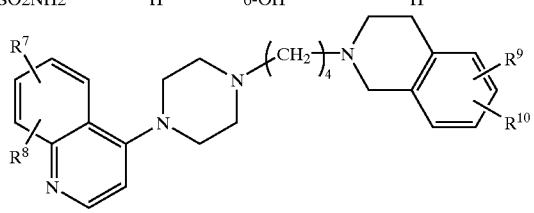

| | | | |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 7-F | H | 4-F | 5-F |
| 7-F | H | 4-Cl | 5-Cl |
| 7-F | H | 4-OH | 5-OH |
| 7-F | H | 4-OMe | 5-OMe |
| 7-F | H | 4-OMe | 5-SO2NH2 |
| 7-F | H | 4-SO2NH2 | 5-OMe |
| 7-F | H | 3-F | 6-F |
| 7-F | H | 3-Cl | 6-Cl |
| 7-F | H | 3-OH | 6-OH |
| 7-F | H | 3-OMe | 6-OMe |
| 7-F | H | 3-OMe | 6-SO2NH2 |
| 7-F | H | 3-SO2NH2 | 6-OMe |
| 7-F | H | 3-F | 4-F |
| 7-F | H | 3-F | 5-F |
| 7-F | H | 4-F | 6-F |
| 7-F | H | 3-Cl | 4-Cl |
| 7-F | H | 3-Cl | 5-Cl |
| 7-F | H | 4-Cl | 6-Cl |
| 7-F | H | 3-OH | 4-OH |
| 7-F | H | 3-OH | 5-OH |
| 7-F | H | 4-OH | 6-OH |
| 7-F | H | 3-OMe | 4-OMe |
| 7-F | H | 3-OMe | 5-OMe |
| 7-F | H | 4-OMe | 6-OMe |
| 7-SO2NH2 | H | 4-F | 5-F |
| 7-SO2NH2 | H | 4-Cl | 5-Cl |
| 7-SO2NH2 | H | 4-OH | 5-OH |
| 7-SO2NH2 | H | 4-OMe | 5-OMe |
| 7-SO2NH2 | H | 4-OMe | 5-SO2NH2 |
| 7-SO2NH2 | H | 4-SO2NH2 | 5-OMe |
| 7-SO2NH2 | H | 3-F | 6-F |
| 7-SO2NH2 | H | 3-Cl | 6-Cl |
| 7-SO2NH2 | H | 3-OH | 6-OH |
| 7-SO2NH2 | H | 3-OMe | 6-OMe |
| 7-SO2NH2 | H | 3-OMe | 6-SO2NH2 |
| 7-SO2NH2 | H | 3-SO2NH2 | 6-OMe |
| 7-SO2NH2 | H | 3-F | 4-F |
| 7-SO2NH2 | H | 3-F | 5-F |
| 7-SO2NH2 | H | 4-F | 6-F |
| 7-SO2NH2 | H | 3-Cl | 4-Cl |
| 7-SO2NH2 | H | 3-Cl | 5-Cl |
| 7-SO2NH2 | H | 4-Cl | 6-Cl |
| 7-SO2NH2 | H | 3-OH | 4-OH |
| 7-SO2NH2 | H | 3-OH | 5-OH |
| 7-SO2NH2 | H | 4-OH | 6-OH |
| 7-SO2NH2 | H | 3-OMe | 4-OMe |
| 7-SO2NH2 | H | 3-OMe | 5-OMe |
| 7-SO2NH2 | H | 4-OMe | 6-OMe |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OH | H |
| 7-F | H | 6-F | H |
| 7-F | H | 6-Cl | H |
| 7-F | H | 6-F | H |
| 7-F | H | 6-OH | H |
| 7-F | H | 6-SO2NH2 | H |
| 7-F | H | 6-OH | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | H |
| 7-SO2NH2 | H | 4-Cl | H |

-continued

| | | | |
|---|---|---|---|
| 7-SO2NH2 | H | 4-OH | H |
| 7-SO2NH2 | H | 4-SO2NH2 | H |
| 7-SO2NH2 | H | 4-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OH | H |
| 7-SO2NH2 | H | 6-F | H |
| 7-SO2NH2 | H | 6-Cl | H |
| 7-SO2NH2 | H | 6-F | H |
| 7-SO2NH2 | H | 6-OH | H |
| 7-SO2NH2 | H | 6-SO2NH2 | H |
| 7-SO2NH2 | H | 6-OH | H |

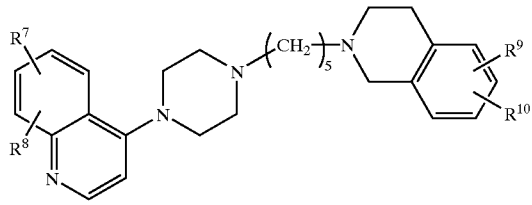

| | | | |
|---|---|---|---|
| H | H | H | H |
| 7-F | H | H | H |
| 7-OH | H | H | H |
| 7-Cl | H | H | H |
| 7-SO2NH2 | H | H | H |
| 7-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OMe | H |
| H | H | 5-F | H |
| H | H | 5-Cl | H |
| H | H | 5-F | H |
| H | H | 5-OH | H |
| H | H | 5-SO2NH2 | H |
| H | H | 5-OH | H |
| H | H | 6-F | H |
| H | H | 6-Cl | H |
| H | H | 6-F | H |
| H | H | 6-OH | H |
| H | H | 6-SO2NH2 | H |
| H | H | 6-OH | H |
| 7-F | H | 4-F | 5-F |
| 7-F | H | 4-Cl | 5-Cl |
| 7-F | H | 4-OH | 5-OH |
| 7-F | H | 4-OMe | 5-OMe |
| 7-F | H | 4-OMe | 5-SO2NH2 |
| 7-F | H | 4-SO2NH2 | 5-OMe |

-continued

| | | | |
|---|---|---|---|
| 7-F | H | 3-F | 6-F |
| 7-F | H | 3-Cl | 6-Cl |
| 7-F | H | 3-OH | 6-OH |
| 7-F | H | 3-OMe | 6-OMe |
| 7-F | H | 3-OMe | 6-SO2NH2 |
| 7-F | H | 3-SO2NH2 | 6-OMe |
| 7-F | H | 3-F | 4-F |
| 7-F | H | 3-F | 5-F |
| 7-F | H | 4-F | 6-F |
| 7-F | H | 3-Cl | 4-Cl |
| 7-F | H | 3-Cl | 5-Cl |
| 7-F | H | 4-Cl | 6-Cl |
| 7-F | H | 3-OH | 4-OH |
| 7-F | H | 3-OH | 5-OH |
| 7-F | H | 4-OH | 6-OH |
| 7-F | H | 3-OMe | 4-OMe |
| 7-F | H | 3-OMe | 5-OMe |
| 7-F | H | 4-OMe | 6-OMe |
| 7-SO2NH2 | H | 4-F | 5-F |
| 7-SO2NH2 | H | 4-Cl | 5-Cl |
| 7-SO2NH2 | H | 4-OH | 5-OH |
| 7-SO2NH2 | H | 4-OMe | 5-OMe |
| 7-SO2NH2 | H | 4-OMe | 5-SO2NH2 |
| 7-SO2NH2 | H | 4-SO2NH2 | 5-OMe |
| 7-SO2NH2 | H | 3-F | 6-F |
| 7-SO2NH2 | H | 3-Cl | 6-Cl |
| 7-SO2NH2 | H | 3-OH | 6-OH |
| 7-SO2NH2 | H | 3-OMe | 6-OMe |
| 7-SO2NH2 | H | 3-OMe | 6-SO2NH2 |
| 7-SO2NH2 | H | 3-SO2NH2 | 6-OMe |
| 7-SO2NH2 | H | 3-F | 4-F |
| 7-SO2NH2 | H | 3-F | 5-F |
| 7-SO2NH2 | H | 4-F | 6-F |
| 7-SO2NH2 | H | 3-Cl | 4-Cl |
| 7-SO2NH2 | H | 3-Cl | 5-Cl |
| 7-SO2NH2 | H | 4-Cl | 6-Cl |
| 7-SO2NH2 | H | 3-OH | 4-OH |
| 7-SO2NH2 | H | 3-OH | 5-OH |
| 7-SO2NH2 | H | 4-OH | 6-OH |
| 7-SO2NH2 | H | 3-OMe | 4-OMe |
| 7-SO2NH2 | H | 3-OMe | 5-OMe |
| 7-SO2NH2 | H | 4-OMe | 6-OMe |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OMe | H |
| 7-F | H | 5-F | H |
| 7-F | H | 5-Cl | H |
| 7-F | H | 5-F | H |
| 7-F | H | 5-OH | H |
| 7-F | H | 5-SO2NH2 | H |
| 7-F | H | 5-OH | H |
| 7-F | H | 6-F | H |
| 7-F | H | 6-Cl | H |
| 7-F | H | 6-F | H |
| 7-F | H | 6-OH | H |
| 7-F | H | 6-SO2NH2 | H |
| 7-F | H | 6-OH | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |

| R7 | R8 | R9 | R10 |
|---|---|---|---|
| 7-SO2NH2 | H | 4-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OMe | H |
| 7-SO2NH2 | H | 5-F | H |
| 7-SO2NH2 | H | 5-Cl | H |
| 7-SO2NH2 | H | 5-F | H |
| 7-SO2NH2 | H | 5-OH | H |
| 7-SO2NH2 | H | 5-SO2NH2 | H |
| 7-SO2NH2 | H | 5-OH | H |
| 7-SO2NH2 | H | 6-F | H |
| 7-SO2NH2 | H | 6-Cl | H |
| 7-SO2NH2 | H | 6-F | H |
| 7-SO2NH2 | H | 6-OH | H |
| 7-SO2NH2 | H | 6-SO2NH2 | H |
| 7-SO2NH2 | H | 6-OH | H |

Structure: Quinoline with R7, R8 substituents, connected via piperazine-(CH2)3-NH-CH2CH2-phenyl with R9, R10

| R7 | R8 | R9 | R10 |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 7-F | H | 2-F | H |
| 7-F | H | 2-Cl | H |
| 7-F | H | 2-OH | H |
| 7-F | H | 2-SO2NH2 | H |
| 7-F | H | 2-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-SO2NH2 | H | 2-F | H |
| 7-SO2NH2 | H | 2-Cl | H |
| 7-SO2NH2 | H | 2-OH | H |
| 7-SO2NH2 | H | 2-SO2NH2 | H |
| 7-SO2NH2 | H | 2-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-F | H | 2-F | 3-F |
| 7-F | H | 2-Cl | 3-Cl |
| 7-F | H | 2-OH | 3-OH |
| 7-F | H | 2-OMe | 3-OMe |
| 7-F | H | 2-F | 4-F |
| 7-F | H | 2-Cl | 4-Cl |
| 7-F | H | 2-OH | 4-OH |
| 7-F | H | 2-OMe | 4-OMe |
| 7-F | H | 2-F | 5-F |
| 7-F | H | 2-Cl | 5-Cl |
| 7-F | H | 2-OH | 5-OH |
| 7-F | H | 2-OMe | 5-OMe |
| 7-F | H | 2-F | 6-F |
| 7-F | H | 2-Cl | 6-Cl |
| 7-F | H | 2-OH | 6-OH |
| 7-F | H | 2-OMe | 6-OMe |
| 7-F | H | 3-F | 4-F |
| 7-F | H | 3-Cl | 4-Cl |
| 7-F | H | 3-OH | 4-OH |
| 7-F | H | 3-OMe | 4-OMe |
| 7-F | H | 3-SO2NH2 | 4-OMe |
| 7-F | H | 3-OMe | 4-SO2NH2 |
| 7-SO2NH2 | H | 2-F | 3-F |
| 7-SO2NH2 | H | 2-Cl | 3-Cl |
| 7-SO2NH2 | H | 2-OH | 3-OH |
| 7-SO2NH2 | H | 2-OMe | 3-OMe |
| 7-SO2NH2 | H | 2-F | 4-F |
| 7-SO2NH2 | H | 2-Cl | 4-Cl |
| 7-SO2NH2 | H | 2-OH | 4-OH |
| 7-SO2NH2 | H | 2-OMe | 4-OMe |
| 7-SO2NH2 | H | 2-F | 5-F |
| 7-SO2NH2 | H | 2-Cl | 5-Cl |
| 7-SO2NH2 | H | 2-OH | 5-OH |
| 7-SO2NH2 | H | 2-OMe | 5-OMe |
| 7-SO2NH2 | H | 2-F | 6-SO2NH2 |
| 7-SO2NH2 | H | 2-Cl | 6-Cl |
| 7-SO2NH2 | H | 2-OH | 6-OH |
| 7-SO2NH2 | H | 2-OMe | 6-OMe |
| 7-SO2NH2 | H | 3-F | 4-F |
| 7-SO2NH2 | H | 3-Cl | 4-Cl |
| 7-SO2NH2 | H | 3-OH | 4-OH |
| 7-SO2NH2 | H | 3-OMe | 4-OMe |
| 7-SO2NH2 | H | 3-SO2NH2 | 4-OMe |
| 7-SO2NH2 | H | 3-OMe | 4-SO2NH2 |

Structure: Quinoline with R7, R8 substituents, connected via piperazine-(CH2)4-NH-CH2CH2-phenyl with R9, R10

| R7 | R8 | R9 | R10 |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 2-F | H |
| H | H | 2-Cl | H |
| H | H | 2-OH | H |
| H | H | 2-SO2NH2 | H |

-continued

| | | | |
|---|---|---|---|
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 7-F | H | 2-F | H |
| 7-F | H | 2-Cl | H |
| 7-F | H | 2-OH | H |
| 7-F | H | 2-SO2NH2 | H |
| 7-F | H | 2-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-SO2NH2 | H | 2-F | H |
| 7-SO2NH2 | H | 2-Cl | H |
| 7-SO2NH2 | H | 2-OH | H |
| 7-SO2NH2 | H | 2-SO2NH2 | H |
| 7-SO2NH2 | H | 2-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-F | H | 2-F | 3-F |
| 7-F | H | 2-Cl | 3-Cl |
| 7-F | H | 2-OH | 3-OH |
| 7-F | H | 2-OMe | 3-OMe |
| 7-F | H | 2-F | 4-F |
| 7-F | H | 2-Cl | 4-Cl |
| 7-F | H | 2-OH | 4-OH |
| 7-F | H | 2-OMe | 4-OMe |
| 7-F | H | 2-F | 5-F |
| 7-F | H | 2-Cl | 5-Cl |
| 7-F | H | 2-OH | 5-OH |
| 7-F | H | 2-OMe | 5-OMe |
| 7-F | H | 2-F | 6-F |
| 7-F | H | 2-Cl | 6-Cl |
| 7-F | H | 2-OH | 6-OH |
| 7-F | H | 2-OMe | 6-OMe |
| 7-F | H | 3-F | 4-F |
| 7-F | H | 3-Cl | 4-Cl |
| 7-F | H | 3-OH | 4-OH |
| 7-F | H | 3-OMe | 4-OMe |
| 7-F | H | 3-SO2NH2 | 4-OMe |
| 7-F | H | 3-OMe | 4-SO2NH2 |
| 7-SO2NH2 | H | 2-F | 3-F |
| 7-SO2NH2 | H | 2-Cl | 3-Cl |
| 7-SO2NH2 | H | 2-OH | 3-OH |
| 7-SO2NH2 | H | 2-OMe | 3-OMe |
| 7-SO2NH2 | H | 2-F | 4-F |
| 7-SO2NH2 | H | 2-Cl | 4-Cl |
| 7-SO2NH2 | H | 2-OH | 4-OH |
| 7-SO2NH2 | H | 2-OMe | 4-OMe |
| 7-SO2NH2 | H | 2-F | 5-F |
| 7-SO2NH2 | H | 2-Cl | 5-Cl |
| 7-SO2NH2 | H | 2-OH | 5-OH |
| 7-SO2NH2 | H | 2-OMe | 5-OMe |
| 7-SO2NH2 | H | 2-F | 6-SO2NH2 |
| 7-SO2NH2 | H | 2-Cl | 6-Cl |
| 7-SO2NH2 | H | 2-OH | 6-OH |
| 7-SO2NH2 | H | 2-OMe | 6-OMe |
| 7-SO2NH2 | H | 3-F | 4-F |
| 7-SO2NH2 | H | 3-Cl | 4-Cl |
| 7-SO2NH2 | H | 3-OH | 4-OH |
| 7-SO2NH2 | H | 3-OMe | 4-OMe |
| 7-SO2NH2 | H | 3-SO2NH2 | 4-OMe |
| 7-SO2NH2 | H | 3-OMe | 4-SO2NH2 |

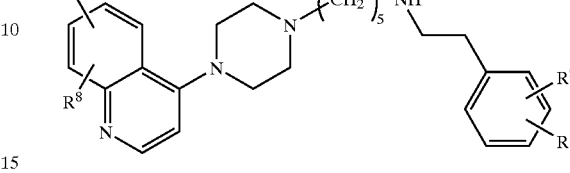

| | | | |
|---|---|---|---|
| H | H | H | H |
| 7-F | H | H | H |
| 7-OH | H | H | H |
| 7-Cl | H | H | H |
| 7-SO2NH2 | H | H | H |
| 6-F | 7-F | H | H |
| 6-OH | 7-F | H | H |
| 6-Cl | 7-F | H | H |
| 6-SO2NH2 | 7-F | H | H |
| 5-F | 7-F | H | H |
| 5-OH | 7-F | H | H |
| 5-Cl | 7-F | H | H |
| 5-SO2NH2 | 7-F | H | H |
| H | H | 2-F | H |
| H | H | 2-Cl | H |
| H | H | 2-OH | H |
| H | H | 2-SO2NH2 | H |
| H | H | 2-OMe | H |
| H | H | 3-F | H |
| H | H | 3-Cl | H |
| H | H | 3-OH | H |
| H | H | 3-SO2NH2 | H |
| H | H | 3-OMe | H |
| H | H | 4-F | H |
| H | H | 4-Cl | H |
| H | H | 4-OH | H |
| H | H | 4-SO2NH2 | H |
| H | H | 4-OMe | H |
| 7-F | H | 2-F | H |
| 7-F | H | 2-Cl | H |
| 7-F | H | 2-OH | H |
| 7-F | H | 2-SO2NH2 | H |
| 7-F | H | 2-OMe | H |
| 7-F | H | 3-F | H |
| 7-F | H | 3-Cl | H |
| 7-F | H | 3-OH | H |
| 7-F | H | 3-SO2NH2 | H |
| 7-F | H | 3-OMe | H |
| 7-F | H | 4-F | H |
| 7-F | H | 4-Cl | H |
| 7-F | H | 4-OH | H |
| 7-F | H | 4-SO2NH2 | H |
| 7-F | H | 4-OMe | H |
| 7-SO2NH2 | H | 2-F | H |
| 7-SO2NH2 | H | 2-Cl | H |
| 7-SO2NH2 | H | 2-OH | H |
| 7-SO2NH2 | H | 2-SO2NH2 | H |
| 7-SO2NH2 | H | 2-OMe | H |
| 7-SO2NH2 | H | 3-F | H |
| 7-SO2NH2 | H | 3-Cl | H |
| 7-SO2NH2 | H | 3-OH | H |
| 7-SO2NH2 | H | 3-SO2NH2 | H |
| 7-SO2NH2 | H | 3-OMe | H |
| 7-SO2NH2 | H | 4-F | H |
| 7-SO2NH2 | H | 4-Cl | H |
| 7-SO2NH2 | H | 4-OH | H |
| 7-SO2NH2 | H | 4-SO2NH2 | H |
| 7-SO2NH2 | H | 4-OMe | H |
| 7-F | H | 2-F | 3-F |
| 7-F | H | 2-Cl | 3-Cl |
| 7-F | H | 2-OH | 3-OH |
| 7-F | H | 2-OMe | 3-OMe |
| 7-F | H | 2-F | 4-F |

-continued

| | | | |
|---|---|---|---|
| 7-F | H | 2-Cl | 4-Cl |
| 7-F | H | 2-OH | 4-OH |
| 7-F | H | 2-OMe | 4-OMe |
| 7-F | H | 2-F | 5-F |
| 7-F | H | 2-Cl | 5-Cl |
| 7-F | H | 2-OH | 5-OH |
| 7-F | H | 2-OMe | 5-OMe |
| 7-F | H | 2-F | 6-F |
| 7-F | H | 2-Cl | 6-Cl |
| 7-F | H | 2-OH | 6-OH |
| 7-F | H | 2-OMe | 6-OMe |
| 7-F | H | 3-F | 4-F |
| 7-F | H | 3-Cl | 4-Cl |
| 7-F | H | 3-OH | 4-OH |
| 7-F | H | 3-OMe | 4-OMe |
| 7-F | H | 3-SO2NH2 | 4-OMe |
| 7-F | H | 3-OMe | 4-SO2NH2 |
| 7-SO2NH2 | H | 2-F | 3-F |
| 7-SO2NH2 | H | 2-Cl | 3-Cl |
| 7-SO2NH2 | H | 2-OH | 3-OH |
| 7-SO2NH2 | H | 2-OMe | 3-OMe |
| 7-SO2NH2 | H | 2-F | 4-F |
| 7-SO2NH2 | H | 2-Cl | 4-Cl |
| 7-SO2NH2 | H | 2-OH | 4-OH |
| 7-SO2NH2 | H | 2-OMe | 4-OMe |
| 7-SO2NH2 | H | 2-F | 5-F |
| 7-SO2NH2 | H | 2-Cl | 5-Cl |
| 7-SO2NH2 | H | 2-OH | 5-OH |
| 7-SO2NH2 | H | 2-OMe | 5-OMe |
| 7-SO2NH2 | H | 2-F | 6-SO2NH2 |
| 7-SO2NH2 | H | 2-Cl | 6-Cl |
| 7-SO2NH2 | H | 2-OH | 6-OH |
| 7-SO2NH2 | H | 2-OMe | 6-OMe |
| 7-SO2NH2 | H | 3-F | 4-F |
| 7-SO2NH2 | H | 3-Cl | 4-Cl |
| 7-SO2NH2 | H | 3-OH | 4-OH |
| 7-SO2NH2 | H | 3-OMe | 4-OMe |
| 7-SO2NH2 | H | 3-SO2NH2 | 4-OMe |
| 7-SO2NH2 | H | 3-OMe | 4-SO2NH2 |

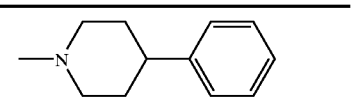

| R11 | R12 | n | m | R13 |
|---|---|---|---|---|
| H | H | 0 | 3 | 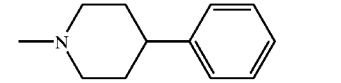 |
| H | Me | 0 | 3 | 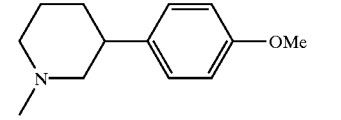 |
| H | H | 0 | 3 | 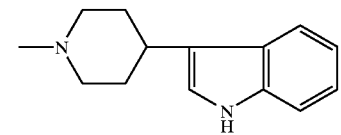 |
| H | H | 0 | 3 | 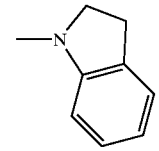 |
| H | H | 0 | 3 | 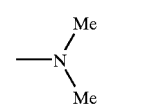 |
| H | H | 1 | 2 | 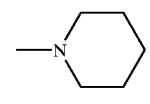 |
| H | H | 0 | 3 | 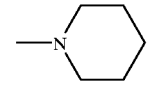 |
| 2-Me | H | 0 | 3 | 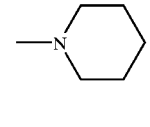 |
| H | H | 0 | 2 | 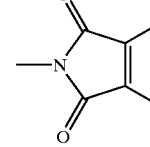 |
| H | H | 0 | 3 | 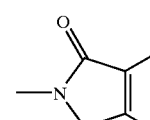 |
| H | H | 0 | 4 | 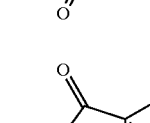 |
| 6-F | H | 0 | 4 | 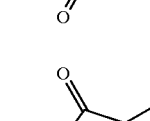 |
| H | H | 0 | 5 | 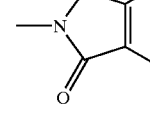 |

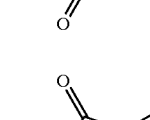

-continued
| | | | | |
|---|---|---|---|---|
| H | H | 0 | 6 | 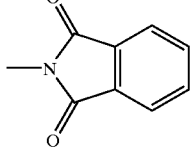 |
| H | H | 0 | 3 | 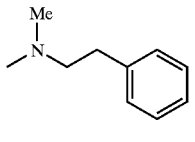 |
| 6-F | H | 0 | 3 | 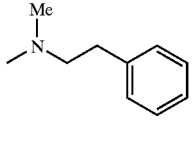 |
| 6-F | H | 0 | 4 | 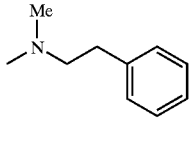 |
| 6-OMe | H | 0 | 3 | 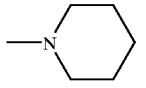 |
| 6-F | H | 0 | 3 | 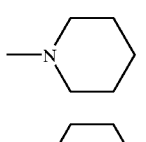 |
| 5-F | H | 0 | 3 | 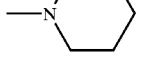 |
| H | H | 0 | 4 | 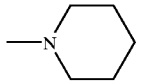 |
| H | H | 0 | 5 | 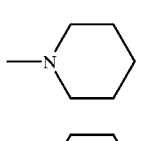 |
| H | H | 0 | 4 | 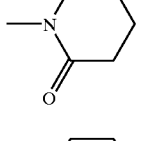 |
| H | H | 0 | 5 | 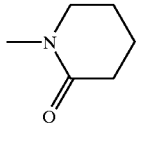 |
| 6-F | H | 0 | 4 |  |
| 6-F | H | 0 | 4 | 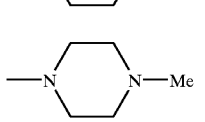 |
-continued
$$Ar^3 - D^2 - (CH_2)_I - R^{14}$$
| Ar3 | D2 | I | R14 |
|---|---|---|---|
| 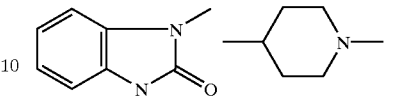 | 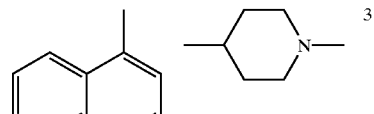 | 3 | 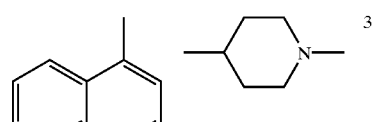 |
| 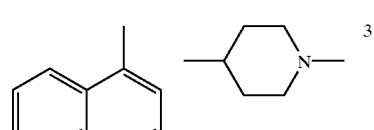 | 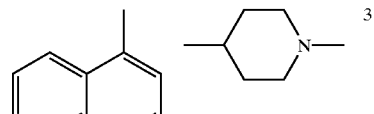 | 3 | 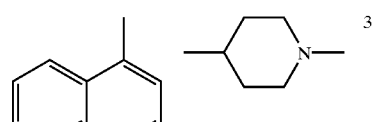 |
| 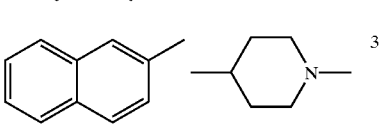 | 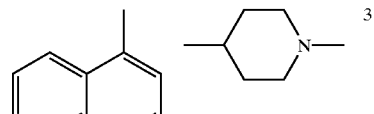 | 3 | 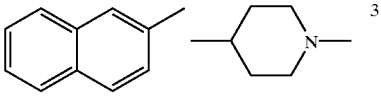 |
| 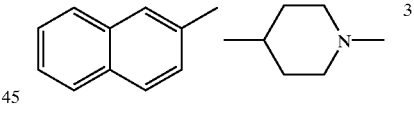 | 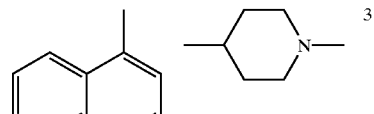 | 3 | 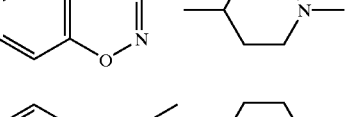 |
| 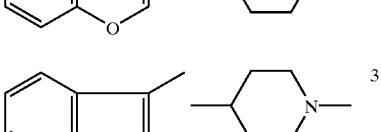 | 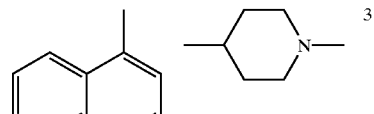 | 3 | 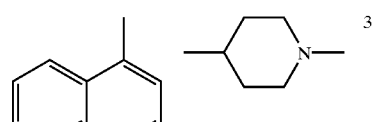 |
| 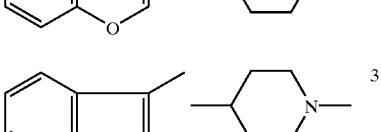 | 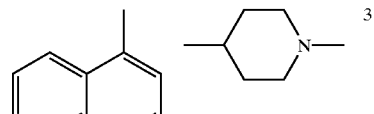 | 3 | 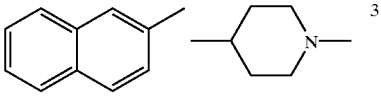 |
| 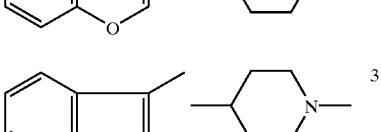 | 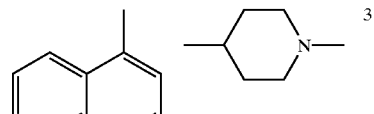 | 3 | 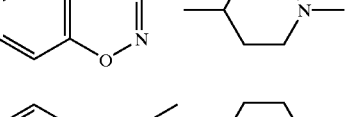 |
| 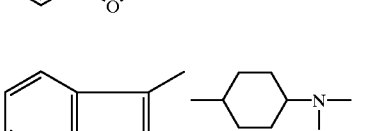 | 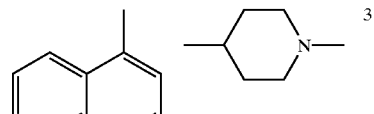 | 3 | 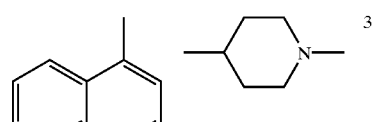 |
|  | 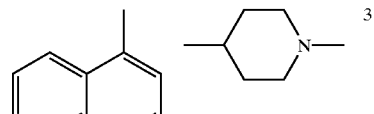 | 3 | 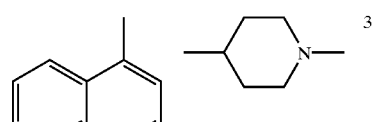 |
|  | 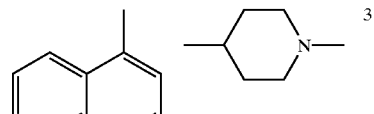 | 3 | 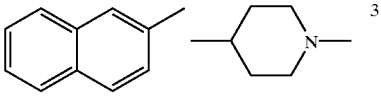 |
|  | | 3 | 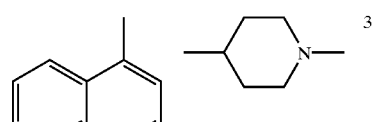 |

-continued

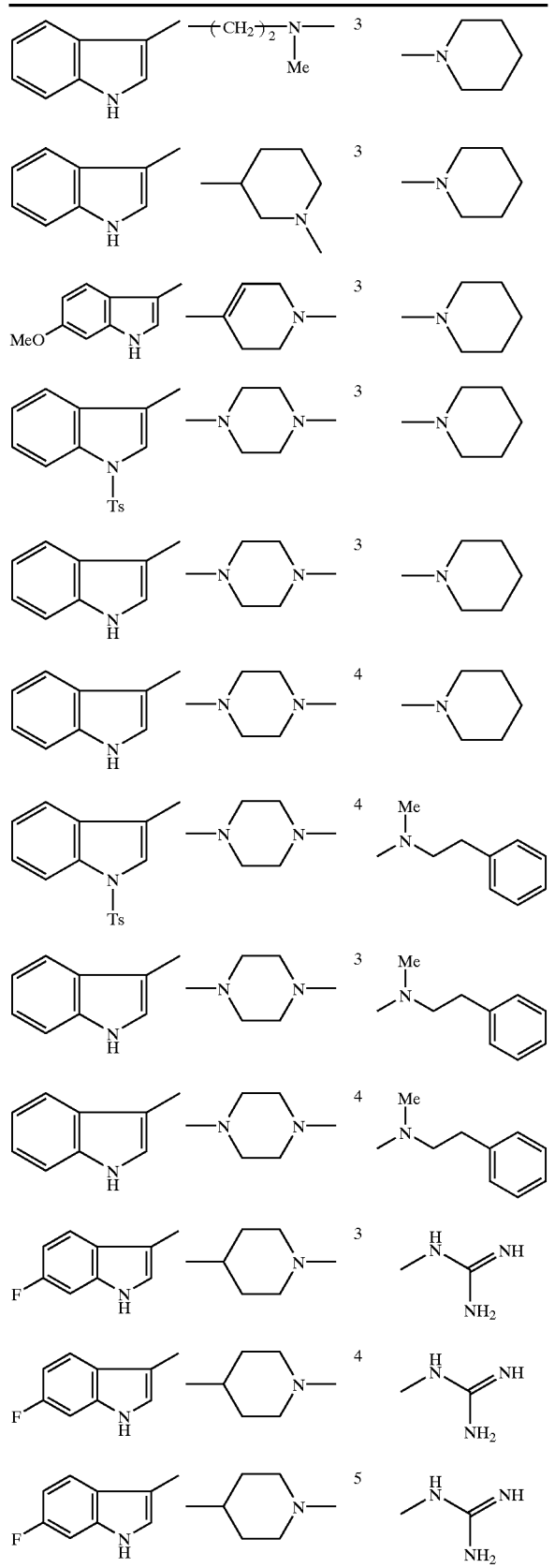

-continued

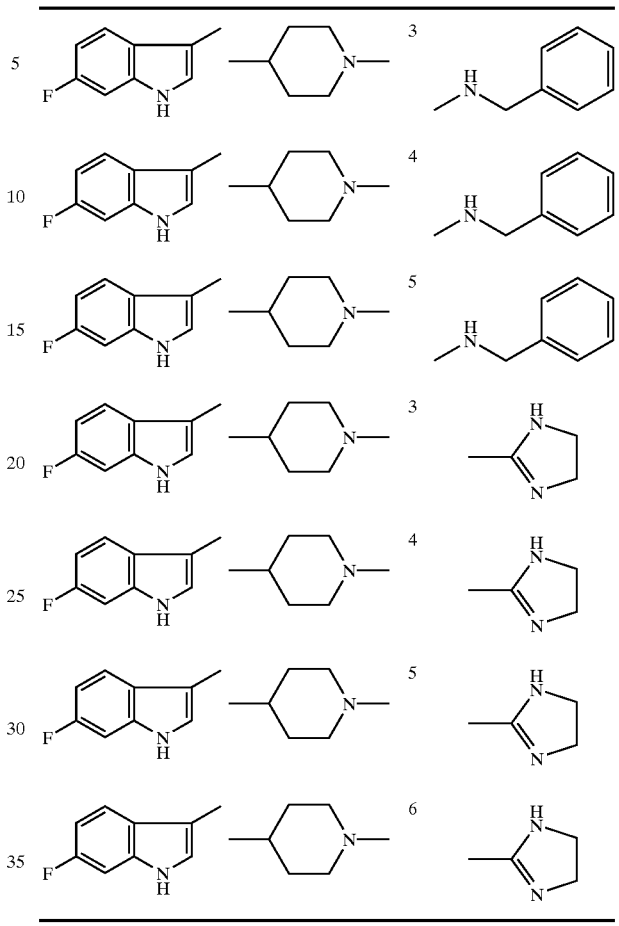

Of the invented compounds, there are a variety of optical isomers when the compound in question has an asymmetric carbon in the molecule, and there are a variety of diastereomers when the compound has at least two asymmetric carbons. The present invention also includes these optical isomers and individual isomers. Additionally, the present invention also includes stereoisomers.

Some compounds of the compounds of the general formula (I) according to the invention have already been disclosed in literature [Arch. Pharm. Pharm. Med. Chem., 329, 3(1996)] or PCT International Publication No. WO94/24127, and the production process described therein can be applied as intact.

Generally, the compounds are produced by, for example, (1) an N-alkylation using amine (IV) and alkyl halide (V) in the presence of an appropriate base (scheme 1-1), (2) an N-alkylation using haloalkylamide (VI) and amine (VII) in the presence of an appropriate base (scheme 1-2), or (3) a reductive amination using an appropriate aldehyde Ar—B'—CHO (wherein B' is bond, or alkylene having 1 to 3 carbon atoms, which is unsubstituted or substituted with alkyl group having 1 to 8 carbon atoms, halogen, or hydroxy), and a reducing agent such as sodium cyanoborohydride, sodium triacetoxyborohydride and the like or a hydrogenation (scheme 1-3), as shown in scheme 1:

Scheme 1

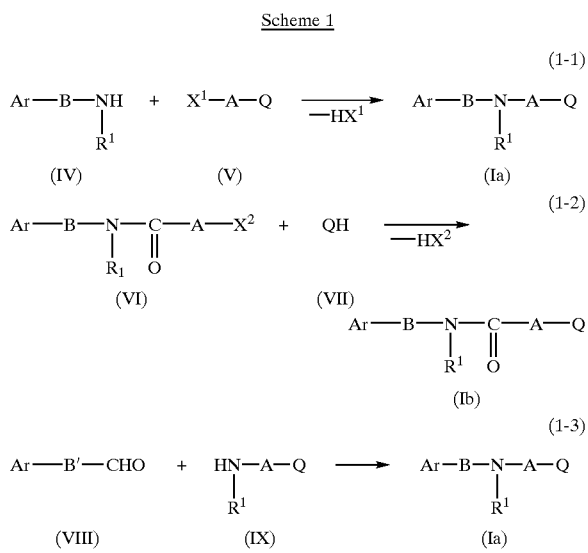

(wherein Ar, B, $R^1$, A, and Q have the same meanings as defined above; and each of $X^1$ and $x^2$ is chloro, bromo, iodo, methanesulfonyloxy, or p-toluenesulfonyloxy).

The N-alkylation performed in scheme 1-1 according to the present invention can be performed by conventionally known techniques. The solvents include an alcoholic solvent such as methanol, ethanol and the like; an etherial solvent such as dioxane, THF and the like; an aprotic solvent such as DMF, DMSO, acetonitrile and the like. Among them, acetonitrile and DMF are preferably employed, and the use of acetonitrile generally yields satisfactory results. The bases include a metal hydroxide such as assodium hydroxide, potassium hydroxide and the like; a metal alkoxide such as sodium alkoxides, potassium alkoxides andthe like; a metal hydride such as sodium hydride, potassium hydride and the like; an alkylmetal such as n-butyllithium, methyllithium and the like; a metal carbonate such as sodium hydrogencarbonate, potassium carbonate, sodium carbonate and the like; a tertiary amine such as trialkylamines, diisopropylethylamine and the like. Among them, sodium hydride, potassium carbonate, sodium carbonate, triethylamine, and diisopropylethylamine are preferably employed, and the use of potassium carbonate generally yields satisfactory results. The equivalent of the base used is not specifically limited, but the use of 1 to 50 equivalents, preferably 2 to 20 equivalents, and more preferably 2 to 10 equivalents relative to amine (IV) generally yields satisfactory results. The equivalent of alkyl halide or the like (V) used is not specifically limited, but the use of 0.5 to 10 equivalents, preferably 0.8 to 5 equivalents, and more preferably 1 to 3 equivalents relative to amine (IV) generally yields'satisfactory results. The reaction is generally performed at a reaction temperature in a range of 20° C. to 150° C., preferably in a range of 40° C. to 120° C., and more preferably in a range of 60° C. to 100° C. The reaction time generally falls in a range of 30 minutes to 150 hours, preferably in a range of 1 hour to 72 hours, and more preferably in a range of 2 hours to 24 hours.

The N-alkylation performed in scheme 1-2 according to the present invention can be carried out in the same manner as in scheme 1-1. The solvents include an alcoholic solvent such as methanol, ethanol and the like; an etherial solvent such as dioxane, THF and the like; an aprotic solvent such as DMF, DMSO, acetonitrile and the like. Among them, acetonitrile and DMF are preferably employed, and the use of acetonitrile generally yields satisfactory results. The bases include a metal hydroxide such as sodium hydroxide, potassium hydroxide and the like; a metal alkoxide such as sodium alkoxides, potassium alkoxides and the like; a metal hydride such as sodium hydride, potassium hydride and the like; an alkylmetal such as n-butyllithium, methyllithium and the like; a metal carbonate such as sodium hydrogencarbonate, potassium carbonate, sodium carbonate and the like; a tertialy amine such as trialkylamines and the like. Among them, sodium hydride, potassium carbonate, sodium carbonate, triethylamine, and diisopropylethylamine are preferably employed, and the use of potassium carbonate generally yieldssatisfactory results. The equivalent of the base used is not specifically limited, but the use of 1 to 50 equivalents, preferably 2 to 20 equivalents, and more preferably 2 to 10 equivalents relative to haloalkylamide (VI) generally yields satisfactory results. When 3 equivalents or more of amine (VII) is used, satisfactory results can be obtained without the addition of a base. The equivalent of amine (VII) used is not specifically limited, but the use of 1 to 50 equivalents, preferably 1 to 30 equivalents, and more preferably 2 to 5 equivalents relative to haloalkylamide (VI) generally yields satisfactory results. The reaction is generally performed at a reaction temperature in a range of 20° C. to 150° C., preferably in a range of 40° C. to 120° C., and more preferably in a range of 60° C. to 100° C. The reaction time generally falls in a range of 30 minutes to 150 hours, preferably in a range of 1 hour to 72 hours, and more preferably in a range of 2 hours to 24 hours.

The reductive amination performed in scheme 1-3 according to the invention can be performed by conventionally known techniques. The solvents include a halogen solvent such as 1,2-dichloroethane, dichloromethane and the like; an etherial solvent such as THF and the like; an alcoholic solvent such as methanol, ethanol and the like; and acetonitrile and the like. Among them, 1,2-dichloroethane and THF are preferably employed, and the use of 1,2-dichloroethane generally yields satisfactory results. The reducing agents include sodium cyanoborohydride, sodium triacetoxyborohydride, sodium borohydride, borane-pyridine complexes and the like. Among them, sodium cyanoborohydride and sodium triacetoxyborohydride are preferably employed, and the use of sodium triacetoxyborohydride generally yields satisfactory results. The equivalent of the reducing agent used is not specifically limited, but the use of 0.5 to 20 equivalents, preferably 1 to 10 equivalents, and more preferably 1.5 to 3 equivalents relative to aldehyde (VIII) generally yields satisfactory results. The equivalent of amine (IX) used is not specifically limited, but the use of 0.5 to 10 equivalents, preferably 0.8 to 5 equivalents, and more preferably 1 to 3 equivalents relative to aldehyde (VIII) generally yields satisfactory results. The reaction is generally performed at a reaction temperature in a range of −78° C. to 150° C., preferably in a range of −20° C. to 100° C., and more preferably in a range of 0° C. to 40° C. The reaction time generally falls in a range of 30 minutes to 150 hours, preferably in a range of 1 hour to 72 hours, and more preferably in a range of 2 hours to 24 hours.

Commercially available compounds as intact can be used as these compounds (IV) to (IX) for use in the reactions. Additionally, compounds which are not commercially available can be prepared by the application of techniques known to those skilled in the art and described in the following references and patents.

Amine derivative (IV) can be prepared by the application of techniques known to those skilled in the art and disclosed in J. Heterocycl. Chem., 19, 377(1982); WO 9218505;

Japanese Unexamined Patent Application Publication No. 1-207288; Angew. Chem. Int. Ed. Engl., 34, 1348(1995); J. Org. Chem., 62, 1268(1997); EP 714894 and the like.

Haloalkylamine derivative (V) can be prepared by the application of techniques known to those skilled in the art and disclosed in WO9218505; J. Chem. Soc., Chem. Commun., 960(1983); J. Am. Chem. Soc., 87, 67(1945); Acta. Chim. Hung., 128, 375(1991); Pharmazie, 21(1996) and the like.

Amide derivative (VI) can be prepared from amine derivative (IV) by the application of amidation disclosed in J. Med. Chem., 34, 593(1991); Farmaco. Ed. Sci., 45(933); and J. Heterocycl. Chem., 33, 427(1996).

Diamine derivative (IX) can be prepared by the application of techniques known to those skilled in the art and disclosed in. J. Med. Chem., 34, 942(1991); Czech. Chem. Commu., 56, 1725(1991); J. Org. Chem., 61, 3635(1996) and the like.

As shown in the following examples, the compounds represented by the general formula (I) or general formula (III) according to the present invention are antagonists having high affinity and selectivity for the α1B adrenoceptor, and can be used for therapy of diseases in which the α1B adrenoceptor is concerned, and are particularly useful as therapeutic agents for circulatory diseases.

The "therapeutic agents for circulatory diseases" used herein include inhibitory agents of vascular intimal thickening, therapeutic agents for ischemic diseases, therapeutic agents for cardiac diseases, and therapeutic agents for hypertension. The inhibitory agents of vascular intimal thickening are pharmaceutical agents for use in therapy or prophylaxis of angiostenosis due to hypertrophy of vascular smooth muscle cells, more specifically, of arteriosclerosis and restenosis after percutaneous transluminal coronary angioplasty (PTCA). The therapeutic agents for ischemic diseases are pharmaceutical agents for use in therapy or prophylaxis of cardiac or cerebral disorders caused by ischaemia due to, for example, hypervasoconstriction, specifically of angina pectoris, or cerebrovascular spasm after subarachnoid hemorrhage. The therapeutic agents for cardiac diseases are pharmaceutical agents for use in therapy or prophylaxis of, for example, arrhythmia, cardiac hypertrophy, and heart failure. The therapeutic agents for hypertension are pharmaceutical agents for use in therapy or prophylaxis of increased blood pressure due to increased resistance of peripheral vessels, specially of essential hypertension, renovascular hypertension, renal parenchymal hypertension, endocrine hypertension, vascular hypertension, hypertension in patients with dialysis and patients with renal transplantation, and hypertension due to pheochromocytoma. The compounds according to the present invention are especially useful as therapeutic agents for hypertension.

Additionally, the compounds according to the invention exhibit antagonism against the α1B receptor and can also be used as, for example, antineoplastic agents, ocular tension depressants, and therapeutic agents for prostatism. The antineoplastic agents as used herein mean pharmaceutical agents for use in therapy of carcinoma or sarcoma; the ocular tension depressants mean pharmaceutical agents for use in therapy or prophylaxis of various diseases in which the ocular tension increases, specifically of primary open angle glaucoma, primary angle-closure glaucoma, secondary glaucoma, congenital glaucoma, and ocular hypertension. The therapeutic agents for prostatism mean pharmaceutical agents for use in therapy or prophylaxis of tumescent prostate gland or irritation symptom or occlusion symptom due to such tumentia.

Additionally, the compounds according to the present invention are useful to clarify physiological activities mediated by the α1B adrenoceptor, and can be used as pharmacological tools to verify whether the α1B receptor is concerned in various diseases or not.

When the invented α1B adrenoceptor antagonist is clinically used as a pharmaceutical agent, the agent may be a free base or a salt thereof as intact or may further comprise appropriate additives. Such additives include excipients, stabilizers, preservatives, buffers, solubilizing agents, emulsifying agents, diluents, and isotonizing agents. As the form of administration, any of parenteral (non-oral) administration and oral administration yields sufficient. effects. Administration formulations include injections, tablets, liquids, capsules, granules, powders and the like, and these formulations can be produced by known formulation techniques. A dose can be appropriately selected depending on the symptom, age, weight of the patient and dosage method, and the amount of active ingredient per day per adult is 0.0001 mg to 10 g, and preferably 0.001 mg to 1 g. The agent can be administered once or in several installments per day.

EXAMPLES

The present invention will be further illustrated in the following reference examples and examples.

Reference Example 1

6-Fluoro-3-(4-Benzyl-2H,3H,5H-4-azinyl)indole

To a solution of 85% potassium hydroxide (6.3 g, 96 mmol) in methanol (50 mL) was added 6-fluoroindole (3.9 g, 29 mmol) and 1-benzyl-4-piperidone (6.0 g, 32 mmol), and the resulting mixture was refluxed for 20 hours. The reaction mixture was cooled to room temperature and the precipitated solid was filtered, was washed with methanol:water=2:1 (100 mL), and was dried at 50° C. for 10 hours to afford the title compound (8.2 g, yield: 93%) as white crystals.

Reference Example 2

4-(3-(6-Fluoro)indolyl)piperidine

To a solution of 6-fluoro-3-(4-benzyl-2H,3H,5H-4-azinyl)indole (3.0 g, 10 mmol) in methanol (190 mL) was added 2.9 M hydrochloric acid/methanol (5.0 mL) and 5% palladium/carbon (0.60 g), and the mixture was stirred under hydrogen atmosphere at room temperature overnight. After filtrating the reaction mixture through Celite, the filtrate was concentrated. An aqueous sodium hydroxide was then added to pH of 12, and the mixture was extracted with chloroform. After drying over anhydrous sodium sulfate, the chloroform layer was concentrated, and the resulting crude product was reprecipitated with methanol/ether to afford the title compound (2.2 g, yield: 99%) as a white crystalline powder.

Reference Example 3

4-Hydroxy-1-methyl-4-(1-Naphthyl)piperidine

To a solution of 1-bromonaphthalene (2.7 g, 13 mmol) in THF (40 mL) was added dropwise a 1.63 M solution of n-butyllithium (7.3 mL, 12 mmol) in hexane at −78° C. over 10 minutes. The reaction mixture was then stirred for 30 minutes and a solution of N-methylpiperidone (1.1 g, 10 mmol) in THF (2 mL) was added dropwise to the reaction mixture. After stirring the reaction mixture for 2 hours, a saturated aqueous ammonium chloride(10 mL) was added to the reaction mixture, and the mixture was extracted with chloroform. After drying over anhydrous sodium sulfate, the chloroform layer was concentrated, and the resulting crude crystals were recrystallized from chloroform/hexane to afford the title compound (1.5 g, yield: 63%) as white crystals.

Reference Example 4

1-Methyl-4-naphthyl-2H,3H,6H-azine

A solution of 4-hydroxy-1-methyl-4-(1-naphthyl) piperidine (1.1 g, 4.6 mmol) and p-toluenesulfonic acid monohydrate (2.1 g, 11 mmol) in toluene (50 mL) was subjected to azeotropic dehydration under reflux for 4 hours. The reaction solution was cooled to room temperature, and a saturated aqueous sodium hydrogencarbonate(10 mL) was added thereto, and the resulting mixture was extracted with ethyl acetate. After drying over anhydrous sodium sulfate, the ethyl acetate layer was concentrated to afford the title compound (1.0 g, yield: 97%) as white crystals.

Reference Example 5

1-Methyl-4-(1-Naphthyl)piperidine Hydrochloride

To a solution of 1-methyl-4-naphthyl-2H,3H,6H-azine (1.0 g, 4.5 mmol) in methanol (50 mL) was added a 2.9 M hydrochloric acid/methanol (1.9 mL) and 5% palladium/ carbon (0.30 g), and the resulting mixture was stirred under hydrogen atmosphere at room temperature overnight. After filtrating the reaction mixture through Celite, the filtrate was concentrated, and a saturated aqueous sodium hydrogencarbonate was then added to pH of 10, and the resulting mixture was extracted with chloroform. After drying over anhydrous sodium sulfate, the chloroform layer was concentrated, and the resulting crude product was purified by column chromatography on a silica gel (silica gel NH-DM 1020 produced by Fuji Silysia Chemical Ltd., eluent; hexane:ethyl acetate=2:1→ethyl acetate) to afford a free form of the title compound (1.0 g) as a pale yellow viscous oil. After adding hydrochloric acid/methanol, a solution of the free form (1.0 g) in methanol was concentrated, and was recrystallized from methanol/ether to afford the title compound (0.94 g, yield: 80%) as white crystals.

Reference Example 6

4-(1-Naphthyl)-1-(2,2,2-trichloroethoxycarbonyl) piperidine

To a solution of 1-methyl-4-(1-naphthyl)piperidine (0.5 g, 2.2 mmol) in 1,2-dichloroethane (30 mL) was added a proton sponge (2.1 g, 9.9 mmol) and trichloroethyl chloroformate (0.93 mL, 6.6 mmol), and the resulting mixture was stirred at 115° C. overnight. After cooling to room temperature, the reaction mixture was extracted with ethyl acetate, and the ethyl acetate layer was washed with 1 N hydrochloric acid and subsequently with a saturated aqueous sodium chloride. After drying over anhydrous sodium sulfate, the ethyl acetate layer was concentrated, and the resulting crude product was purified by column chromatography on a silica gel (eluent; hexane:ethyl acetate=6:1) to afford the title compound (0.85 g, yield: 100%) as a yellow oil.

Reference Example 7

4-(1-Naphthyl)piperidine Hydrochloride

A solution of 4-(1-naphthyl)-1-(2,2,2-trichloroethoxycarbonyl)piperidine (0.85 g, 2.2 mmol) and a powdered zinc (0.80 g, 1.2 mmol) in acetic acid (22 mL) was stirred at room temperature overnight. After filtrating the reaction mixture through Celite, the filtrate was concentrated, and a saturated aqueous sodium hydrogencarbonate was then added to pH of 10, and the resulting mixture was extracted with chloroform. After drying over anhydrous sodium sulfate, the chloroform layer was concentrated, and the resulting crude product was purified by column chromatography on a silica gel (silica gel NH-DM 1020 produced by Fuji Silysia Chemical Ltd., eluent; chloroform) to afford a free form of the title compound (0.4 g) as a pale yellow oil. After adding hydrochloric acid/methanol, a solution of the free form (0.4 g) in methanol was cooled to afford the title compound (0.36 g, yield: 66%) as white crystals.

Reference Example 8

3-Bromo-1-tosylindole

To a solution of 3-bromoindole (prepared according to the method described in Synthesis, 1096(1982)) (196 mg, 1.0 mmol) and tosyl chloride (286 mg, 1.5 mmol) in benzene (4.5 mL) was added tetra-n-butylammonium hydrogensulfate (34 mg, 0.1 mmol) and a 5.0% aqueous sodium hydroxide (1.0 mL), and the resulting mixture was refluxed for 1 hour. After the reaction solution was cooled to room temperature, water was added to the reaction solution, and the resulting mixture was extracted with chloroform. After drying over anhydrous sodium sulfate, the chloroform layer was concentrated, and the resulting crude product was purified by column chromatography on a silica gel (eluent; hexane:ethyl acetate=6:1) to afford the title compound (335 mg, yield: 96%) as white crystals.

Reference Example 9

3-(1-Piperazyl)-1-tosylindole

To a solution of 3-bromo-1-tosylindole (105 mg, 0.3 mmol) and anhydrous piperazine (258 mg, 3.0 mmol) in toluene (4.5 mL) was added palladium acetate (13.4 mg, 0.055 mmol), BINAP (40.3 mg, 0.065 mmol), and cesium carbonate (318 mmol, 0.9 mmol), and the resulting mixture was refluxed for 6 hours. The reaction solution was cooled to room temperature and the precipitated salt was separated by filtration, and the filtrate was concentrated to afford a crude product. The crude product was purified by column chromatography on a silica gel (eluent; ammonia-saturated chloroform) to afford the title compound (69 mg, yield: 65%) as a colorless viscous oil.

Reference Example 10

1-(3-Chloropropyl)piperidine Hydrochloride

To a solution of piperidine (0.45 g, 5.3 mmol) and 1-bromo-3-chloropropane (5.2 g, 33 mmol) in toluene (17.5 mL) was added tetra-n-butylammonium hydrogensulfate (0.51 g, 1.5 mmol) and a 25% aqueous sodium hydroxide (10 mL), and the resulting mixture was stirred at 40° C. for 3 hours. The reaction solution was cooled to room temperature, and the toluene layer was separated and was then washed with a saturated aqueous sodium chloride and was dried over anhydrous sodium sulfate. After sodium sulfate was filtered off, hydrochloric acid/methanol (2 mL) was added to the filtrate and themixture was concentrated. The resulting crude crystals were recrystallized from methanol/ether to afford the title compound (0.96 g, yield: 91%) as white crystals.

Reference Example 11

1-(3-Chloropropyl)-4-phenylpiperidine Hydrochloride

Using 4-phenylpiperidine hydrochloride (0.67 g, 3.4 mmol) as a material, the reaction and purification were carried out in the same procedure as Reference Example 1 to afford the title compound (0.83 g, yield: 88%) as white crystals.

Reference Example 12

1-(3-Chloropropyl)-3-(4-methoxyphenyl)piperidine Hydrochloride

Using 3-(4-methoxyphenyl)piperidine hydrochloride (120 mg, 0.53 mmol) as a material, the reaction and purification were carried out in the same procedure as Reference Example 1 to afford the title compound (130 mg, yield: 83%) as white crystals.

Reference Example 13

2-(3-Chloropropyl)-1,3,4-trihydroisoquinoline Hydrochloride

Using 1,2,3,4-tetrahydroisoquinoline (2.0 g, 15 mmol) as a material, the reaction and purification were carried out in the same procedure as Reference Example 1 to afford the title compound (2.9 g, yield: 79%) as white crystals.

Reference Example 14

1-(3-Chloropropyl)indoline Hydrochloride

Using indoline (1.8 g, 15 mmol) as a material, the reaction and purification were carried out in the same procedure as Reference Example 1 to afford the title compound (1.3 g, yield: 38%) as white crystals.

Reference Example 15

1- (4-Chlorobutyl)-δ-valerolactam

To a suspension of a powdered 85% potassium hydroxide (3.7 g, 56 mmol) in DMSO (15 mL) was added dropwise a solution of δ-valerolactam (1.4 g, 14 mmol) in DMSO (5 mL) at room temperature, and 1-bromo-4-chlorobutane (4.8 g, 28 mmol) was then added dropwise with water-cooling. After stirring at room temperature for 2 hours, the reaction mixture was poured into water (40 mL) and was then extracted with chloroform. After drying over anhydrous sodium sulfate, the chloroform layer was concentrated, and the resulting crude product was purified by column chromatography on a silica gel (eluent; ethyl acetate) to afford the title compound (2.1 g, yield: 79%) as a colorless oil.

Reference Example 16

1-(5-Chloropentyl)-δ-valerolactam 7

Using 1-bromo-5-chloropentane (5.2 g, 28 mmol) as a material, the reaction and purification were carried out in the same procedure as Reference Example 6 to afford the title compound (2.8 g, yield: 97%) as a colorless oil.

Reference Example 17

4-(3-Indolyl)-3-cyclohexen-1-one Ethylene Ketal

To a solution of 85% potassium hydroxide (1.9 g, 29 mmol) in methanol (14 mL) was added indole (1.2 g, 10 mmol) and 1,4-cyclohexahedione monoethylene ketal (1.7 g, 11 mmol), and the resulting mixture was refluxed for 12 hours. After cooling the reaction mixture to room temperature, the precipitated solid was filtrated, was washed with methanol:water=2:1 (100 mL), and was then dried at 50° C. for 10 hours to afford the title compound (2.4 g, yield: 92%) as white crystals.

Reference Example 18

4-(3-Indolyl)-1-cyclohexenone

To a solution of 4-(3-indolyl)-3-cyclohexen-1-one ethylene ketal (1.96 g, 7.7 mmol) in THF (50 mL) was added 5% palladium/carbon (0.39 g), and the mixture was stirred under hydrogen atmosphere at room temperature overnight. After filtrating the reaction mixture through Celite, the filtrate was concentrated to afford a crude product. THF (40 mL) and 1 N hydrochloric acid (25 mL) were added to the crude product and the resulting mixture was stirred at room temperature for 12 hours. Water (10 mL) was added to the reaction mixture and the mixture was extracted with chloroform. After drying over anhydrous sodium sulfate, the chloroform layer was concentrated, and the resulting crude crystals were recrystallized from chloroform/hexane to afford the title compound (1.4 g, yield: 83%) as white crystals.

Reference Example 19

1-(3-N-Benzyl-N-methylamino)propyl)piperidine Hydrochloride

To a suspended solution of benzylmethylamine (0.61 g, 5.0 mmol) and 1-(3-chloropropyl)piperidine hydrochloride (1.5 g, 7.5 mmol) in acetonitrile (50 mL) was added potassium carbonate (1.03 g, 7.5 mmol), and the resulting mixture was refluxed for 5 hours. After the precipitated salt was filtered off, the filtrate was concentrated, and methanol and subsequently hydrochloric acid/methanol were added to the resulting crude product. After concentrating the solution, the resulting crude crystal was recrystallized from methanol/ether to afford the title compound (0.82 g, yield: 51%) as white crystals.

Reference Example 20

1-(3-(N-Methylamino)propyl)piperidine Hydrochloride

To a solution of 1-(3-(N-benzyl-N-methylamino)propyl) piperidine hydrochloride (0.82 g, 2.6 mmol) in methanol (50 mL) was added 5% palladium/carbon (0.16 g), and the mixture was stirred under hydrogen atmosphere at room temperature overnight. After filtrating the reaction mixture through Celite, the filtrate was concentrated to afford the title compound (0.58 g, yield: 99%) as white crystals.

Reference Example 21

4-Phenyl-1-(3-(4-phenylpiperidyl)propyl)piperidine Hydrochloride

Using 4-phenylpiperidine hydrochloride (99 mg, 0.50 mmol) 'and 1-(3-chloropropyl)-4-phenylpiperidine 2 hydrochloride (110 mg, 0.40 mmol) instead of 4-(3-indolyl)piperidine and 1-(3-chloropropyl)-3-(4-methoxyphenyl)piperidine 3 hydrochloride, respectively, the reaction and purification were carried out in the same procedure as Example 2. The resulting crude product was purified by column chromatography on a silica gel (silica gel NH-DM 1020 produced by Fuji Silysia Chemical Ltd., eluent; hexane:ether=2:1) to afford a free form (106 mg) of the title compound as white crystals. After adding hydrochloric acid/methanol to a solution of the free form in methanol, the mixture was concentrated and was then recrystallized from methanol/ether to afford the title compound (113 mg, yield: 65%) as white crystals.

Example 1

3-(1-(3-(4-Phenylpiperidyl)propyl)-4-piperidyl)indole Hydrochloride

To a suspended solution of 4-(3-indolyl)piperidine (2.0 g, 10 mmol) and 1-(3-chloropropyl)-4-phenylpiperidine hydrochloride (3.1 g, 11.2 mmol) in DMF (60 mL) was added potassium carbonate (5.5 g, 40 mmol), and the mixture was stirred at 100° C. for 4 hours. After the precipitated salt was filtered off, the filtrate was concentrated, water (50 mL) was added to the filtrate, and the mixture was extracted with chloroform. After drying over anhydrous sodium sulfate, the chloroform layer was concentrated to afford a crude product. The crude product was purified by column chromatography on a silica gel (silica gel NH-DM 1020 produced by Fuji Silysia Chemical Ltd., eluent; chloroform) and was then recrystallized from ethyl acetate to afford a free form (1.6 g, yield: 40%) of the title compound as white crystals. After adding hydrochloric acid/methanol to a solution of the free form (1.6 g) in methanol, the mixture was concentrated and was then recrystallized from methanol/ether to afford the title compound (1.8 g) as white crystals.

Example 2

1-(1-(3-(4-Indol-3-ylpiperidyl)propyl)-3-piperidyl)-4-methoxybenzene Hydrochloride

To a suspended solution of 4-(3-indolyl)piperidine (48 mg, 0.24 mmol) and 1-(3-chloropropyl)-3-(4-methoxyphenyl)piperidine hydrochloride (61 mg, 0.2 mmol) in acetonitrile (13 mL) was added potassium carbonate (111 mg, 0.8 mmol), and the resulting mixture was refluxed for 12 hours. After the precipitated salt was filtered off, the filtrate was concentrated, and the resulting crude product was purified by column chromatography on a silica gel (eluent; chloroform:ammonia-saturated chloroform= 10:1→3:1→1:2) to afford a free form (92 mg) of the title compound as a colorless viscous oil. After adding hydrochloric acid/methanol to a solution of the free form in methanol, the mixture was concentrated and was then freeze-dried to afford the title compound (81 mg, yield: 80%) as a white amorphous solid.

Example 3

3-(1-(3-Piperidylpropyl)-4-piperidyl)indole Hydrochloride

Using 1-(3-chloropropyl)piperidine hydrochloride (2.0 g, 10 mmol) instead of 1-(3-chloropropyl)-4-phenylpiperidine hydrochloride, reaction, extraction and concentration were carried out in the same procedure as Example 1. The resulting crude product was purified by column chromatography on a silica gel (silica gel NH-DM 1020 produced by Fuji Silysia Chemical Ltd., eluent; ethyl acetate) and was then recrystallized from ethyl acetate to afford a free form (1.5 g, yield: 59%) of the title compound as white crystals. After adding hydrochloric acid/methanol to a solution of the free form (1.3 g) in methanol, the mixture was concentrated and was then recrystallized from methanol/ether to afford the title compound (1.3 g) as white crystals.

Example 4

(3-(4-Indol-3-ylpiperidyl)propyl)dimethylamine Hydrochloride

To a suspended solution of 4-(3-indolyl)piperidine (1.0 g, 5.0 mmol) and a 96% 3-dimethylaminopropyl chloride hydrochloride (0.91 g, 5.5 mmol) in acetonitrile (50 mL) was added potassium carbonate (2.07 g, 15 mmol) and sodium iodide (0.82 g, 5.5 mmol), and the resulting mixture was refluxed for 5 hours. After the precipitated salt was filtered off, the filtrate was concentrated, and water (40 mL) was added to the filtrate and the mixture was extracted with chloroform. After drying over anhydrous sodium sulfate, the chloroform layer was concentrated, and the resulting crude product was purified by column chromatography on a silica gel (silica gel NH-DM 1020 produced by Fuji Silysia Chemical Ltd., eluent; ethyl acetate) to afford a free form (1.2 g) of the title compound as pale red crystals. After adding hydrochloric acid/methanol to a solution of the free form in methanol, the mixture was concentrated and was then recrystallized from methanol/ether to afford the title compound (1.2 g, yield: 69%) as pale yellow crystals.

Example 5

2-(3-(4-Indol-3-ylpiperidyl)propyl)-1,3,4-trihydroisoquinoline Hydrochloride

Using 2-(3-chloropropyl)-1,2,3,4-tetrahydroisoquinoline hydrochloride (236 mg, 0.96 mmol) instead of 3-dimethylaminopropyl chloride hydrochloride, reaction, extraction and concentration were carried out in the same procedure as Example 4. The resulting crude product was purified by column chromatography on a silica gel (silica gel NH-DM 1020 produced by Fuji Silysia Chemical Ltd., eluent; chloroform) and was then recrystallized from ethyl acetate/hexane to afford a free form (200 mg, yield: 67%) of the title compound as white crystals. After adding hydrochloric acid/methanol to a solution of the free form (154 mg) in methanol, the mixture was concentrated and was then recrystallized from methanol to afford the title compound (84 mg) as pale yellow crystals.

Example 6

3-(1-(3-Indolinylpropyl)-4-piperidyl)indole Hydrochloride

Using 1-(3-chloropropyl)indoline hydrochloride (223 mg, 0.96 mmol) instead of 3-dimethylaminopropyl chloride hydrochloride, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform) to affod a free form (227 mg) of the title compound as a pale yellow viscous oil. After adding hydrochloric acid/methanol to a solution of the free form in methanol, the mixture was concentrated and was then recrystallized from methanol/ether to afford the title compound (186 mg, yield: 54%) as white crystals.

Example 7

2-(3-(4-Indol-3-ylpiperidyl)propyl)isoindoline-1,3-dione Hydrochloride

Using N-(3-bromopropyl)phthalimide (590 mg, 2.2 mmol) instead of 1-(3-chloropropyl)-3-(4-methoxyphenyl) piperidine hydrochloride, reaction and concentration were carried out in the same procedure as Example 2. The crude crystals obtained by concentration was recrystallized from methanol to afford a free form (490 mg, yield: 79%) of the title compound as white crystals. After adding hydrochloric acid/methanol to a solution of the free form (120 mg) in methanol, the mixture was concentrated and was then recrystallized from methanol/ether to afford the title compound (90 mg) as white crystals.

Example 8

2-(4-(4-Indol-3-ylpiperidyl)butyl)isoindoline-1,3-dione Hydrochloride

Using N-(4-bromobutyl)phthalimide (846 mg, 3.0 mmol) instead of 1-(3-chloropropyl)-3-(4-methoxyphenyl) piperidine hydrochloride, reaction and concentration were carried out in the same procedure as Example 2. The resulting crude product was purified by column chromatography on a silica gel (silica gel NH-DM 1020 produced by Fuji Silysia Chemical Ltd., eluent; chloroform) and was then recrystallized from ethyl acetate/hexane to afford a free form (709 mg, yield: 88%) of the title compound as pale yellow crystals. After adding hydrochloric acid/methanol to a solution of the free form (80 mg) in methanol, the mixture was concentrated and was then recrystallized from methanol/ether to afford the title compound (68 mg) as white crystals.

Example 9

2-(5-(4-Indol-3-ylpiperidyl)pentyl)isoindoline-1,3-dione Hydrochloride

Using N-(5-bromopentyl)phthalimide (887 mg, 3.0 mmol) instead of 1-(3-chloropropyl)-3-(4-methoxyphenyl) piperidine hydrochloride, reaction and concentration were carried out in the same procedure as Example 2. The resulting crude product was purified by column chromatography on a silica gel (silica gel NH-DM 1020 produced by Fuji Silysia Chemical Ltd., eluent; chloroform) to afford a free form (928 mg) of the title compound as a pale green viscous oil. After adding hydrochloric acid/methanol to a solution of the free form in methanol, the mixture was concentrated and was then recrystallized from methanol/ether to afford the title compound (791 mg, yield: 88%) as white crystals.

Example 10

1-(4-(4-Indol-3-ylpiperidyl)butyl)piperidin-2-one Hydrochloride

Using 1-(4-chlorobutyl)-δ-valerolactam (334 mg, 1.8 mmol) instead of 3-dimethylaminopropyl chloride hydrochloride, reaction, extraction, and concentration were carried out in the same procedure as Example 4. The resulting crude product was purified by column chromatography on a silica gel (silica gel NH-DM 1020 produced by Fuji Silysia Chemical Ltd., eluent; ethyl acetate) and was then recrystallized from ethyl acetate/hexane to afford a free form (293 mg, yield: 52%) of the title compound as white crystals. After adding hydrochloric acid/methanol to a solution of the free form (90 mg) in methanol, the mixture was concentrated and was then recrystallized from methanol/ether to afford the title compound (89 mg) as white crystals.

Example 11

1-(5-(4-Indol-3-ylpiperidyl)pentyl)piperidin-2-one

Using 1-(5-chloropentyl)-δ-valerolactam (387 mg, 1.9 mmol) instead of 3-dimethylaminopropyl chloride hydrochloride, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform) and was then recrystallized from ethyl acetate/hexane to afford the title compound (125 mg, yield: 21%) as white crystals.

Example 12

3-(1-(4-Piperidylbutyl)-4-piperidyl)indole Hydrochloride

To a suspended solution of lithium aluminium hydride (150 mg, 4.0 mmol) in THF (15 mL) was added dropwise a solution of 1-(4-(4-indol-3-ylpiperidyl)butyl)piperidin-2-one (290 mg, 0.82 mmol) in THF (10 mL) in an ice bath. After stirring at room temperature for 4 hours, a saturated aqueous sodium sulfate and subsequently anhydrous sodium sulfate were added to the reaction mixture, and the precipitated white. solid was separated by filtration. The filtrate was concentrated, and the resulting crude crystals were recrystallized from ethyl acetate to afford a free form (197 mg, yield: 71%) of the title compound as yellow crystals. After adding hydrochloric acid/methanol to a solution of the free form (187 mg) in methanol, the mixture was concentrated and was then recrystallized from methanol/ether to afford the title compound (193 mg) as pale yellow crystals.

Example 13

3-(1-(5-Piperidylpentyl)-4-piperidyl)indole

Using 1-(5-(4-indol-3-ylpiperidyl)pentyl)piperidin-2-one (340 mg, 0.93 mmol) instead of 1-(4-(4-indol-3-ylpiperidyl) butyl)piperidin-2-one, reaction, filtration, and concentration were carried out in the same procedure as Example 12. The resulting crude crystals were recrystallized from ethyl acetate to afford the title compound (273 mg, yield: 83%) as white crystals.

Example 14

3-(1-(3-Isoindolin-2-ylpropyl)-4-piperidyl)indole Hydrochloride

Using 2-(3-(4-indol-3-ylpiperidyl)propyl)isoindoline-1,3-dione (2.0 g, 5.2 mmol) instead of 1-(4-(4-indol-3-ylpiperidyl)butyl)piperidin-2-one, reaction, filtration, and concentration were carried out in the same procedure as Example 12. The resulting crude crystals were recrystallized from ethyl acetate to afford a free form (1.1 g) of the title compound as pale yellow crystals. After adding hydrochloric acid/methanol to a solution of the free form in methanol, the mixture was concentrated and was then recrystallized from methanol/ether to afford the title compound (0.84 g, yield: 38%) as pale green crystals.

Example 15

3-(1-(4-Isoindolin-2-ylbutyl)-4-piperidyl)indole Hydrochloride

Using 2-(4-(4-indol-3-ylpiperidyl)butyl)isoindoline-1,3-dione (362 mg, 0.90 mmol) instead of 1-(4-(4-indol-3-ylpiperidyl)butyl)piperidin-2-one, reaction, filtration, and concentration were carried out in the same procedure as Example 12. The resulting crude product was purified by column chromatography on a silica gel (silica gel NH-DM 1020 produced by Fuji Silysia Chemical Ltd., eluent; chloroform) and was then recrystallized from ethyl acetate to afford a free form (112 mg, yield: 33%) of the title compound as pale yellow crystals. After adding hydrochloric acid/methanol to a solution of the free form (106 mg) in methanol, the mixture was concentrated and was then freeze-dried to afford the title compound (80 mg) as a pale green amorphous solid.

Example 16

3-(1-(5-Isoindolin-2-ylpentyl)-4-piperidyl)indole

Using 2-(5-(4-indol-3-ylpiperidyl)pentyl)isoindoline-1,3-dione (258 mg, 0.62 mmol) instead of 1-(4-(4-indol-3-ylpiperidyl)butyl)piperidin-2-one, reaction, filtration, and concentration were carried out in the same procedure as Example 12. The resulting crude product was purified by column chromatography on a silica gel (silica gel NH-DM 1020 produced by Fuji Silysia Chemical Ltd., eluent; chloroform) and was then recrystallized from ethyl acetate to afford the title compound (103 mg, yield: 43%) as pale yellow crystals.

Example 17

3-(1-(3-(4-Indol-3-ylpiperidyl)propyl)-4-piperidyl)indole Hydrochloride

To a suspended solution of 4-(3-indolyl)piperidine (165 mg, 0.82 mmol) and 1,3-dibromopropane (76 mg, 0.37 mmol) in DMF (6 mL) was added potassium carbonate (216 mg, 1.6 mmol), and the resulting mixture was stirred at 80° C. for 4 hours. After the precipitated salt was filtered off, and the filtrate was then concentrated, water (20 mL) was added to the filtrate and the mixture was extracted with chloroform. After drying over anhydrous sodium sulfate, the chloroform layer was concentrated, and the resulting crude crystals were recrystallized from ethanol to afford a free form (107 mg, yield: 66%) of the title compound as pale yellow crystals. After adding hydrochloric acid/methanol to a solution of the free form (98 mg) in chloroform, the mixture was concentrated and was then recrystallized from methanol/ether to afford the title compound (103 mg) as pale red crystals.

Example 18

1-Methyl-3-(1-(3-(4-Phenylpiperidyl)propyl)-4-piperidyl)indole Hydrochloride

Using 4-(3-(1-methyl)indolyl)piperidine (64 mg, 0.30 mmol) and 1-(3-chloropropyl)-4-phenylpiperidine hydrochloride (99 mg, 0.36 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (eluent; chloroform:ammonia-saturated chloroform=3:1) to afford a free form (122 mg) of the title compound as a pale yellow viscous oil. After adding hydrochloric acid/methanol to a solution of the free form in methanol, the mixture was concentrated and was then reprecipitated with methanol/ether to afford the title compound (88 mg, yield: 60%) as a pale yellow amorphous solid.

Example 19

2-Methyl-3-(1-(3-Piperidylpropyl)-4-piperidyl)indole Hydrochloride

Using 4-(3-(2-methyl)indolyl)piperidine (171 mg, 0.80 mmol) and 1-(3-chloropropyl)piperidine hydrochloride (220 mg, 1.1 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate=1:1) to afford a free form (224 mg, yield: 82%) of the title compound as a pale yellow viscous oil. After adding hydrochloric acid/methanol to a solution of the free form (220 mg) in methanol, the mixture was concentrated and was then recrystallized from ethanol to afford the title compound (120 mg) as pale red crystals. Furthermore, the hydrochloride (49 mg) was freeze-dried to afford the title compound (43 mg) as a white amorphous solid.

Example 20

6-Methoxy-3-(1-(3-Piperidylpropyl)-4-piperidyl)indole Hydrochloride

Using 4-(3-(6-methoxy)indolyl)piperidine (138 mg, 0.60 mmol) and 1-(3-chloropropyl)piperidine hydrochloride (173 mg, 0.84 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate=1:1) and was then recrystallized from ethyl acetate/hexane to afford a free form (131 mg, yield: 61%) of the title compound as white crystals. After adding hydrochloric acid/methanol to a solution of the free form (128 mg) in methanol, the mixture was concentrated and was then recrystallized from ethanol/ether to afford the title compound (137 mg) as white crystals.

Example 21

6-Fluoro-3-(1¡-(3-Piperidylpropyl)-4-piperidyl)indole Hydrochloride

Using 4-(3-(6-fluoro)indolyl)piperidine (218 mg, 1.0 mmol) and 1-(3-chloropropyl)piperidine hydrochloride (277 mg, 1.4 mmol) instead of 4-(3-indolyl)piperidine and 3-dimethylaminopropyl chloride hydrochloride respectively, reaction, extraction, and concentration were carried out in the same procedure as Example 4. The resulting crude product was purified by preparative TLC (developing solvent; ammonia-saturated chloroform:methanol=10:1) and was then recrystallized from chloroform to afford a free form (67 mg, yield 20%) of the title compound as white crystals. After adding hydrochloric acid/methanol to a solution of the free form (50 mg) in methanol, the mixture was concentrated and was then recrystallized from methanol/ether to afford the title compound (37 mg) as white crystals.

Example 22

5-Fluoro-3-(1-(3-Piperidylpropyl)-4-piperidyl)indole Hydrochloride

Using 4-(3-(5-fluoro)indolyl)piperidine (175 mg, 0.80 mmol) and 1-(3-chloropropyl)piperidine hydrochloride (220 mg, 1.1 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; ethyl acetate) and was then recrystallized from ethyl acetate/hexane to afford a free form (212 mg, yield: 99%) of the title compound as white crystals. The free form (208 mg) was dissolved in methanol, and hydrochloric acid/methanol was added to the solution, and the resulting mixture was concentrated and was then recrystallized from methanol/ether to afford the title compound (227 mg) as white crystals.

Example 23

6-Fluoro-3-(1-(3-Isoindolin-2-ylpropyl)-4-piperidyl)indole Hydrochloride

Using 4-(3-(6-fluoro)indolyl)piperidine (109 mg, 0.5 mmol) and 2-(3-chloropropyl)isoindoline hydrochloride (139 mg, 0.6 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:methanol=20:1) and was then recrystallized from chloroform to afford a free form (107 mg, yield: 56%) of the title compound as white crystals. After adding hydrochloric acid/methanol to a solution of the free form (78 mg) in methanol, the mixture was concentrated and was then recrystallized from methanol/ether to afford the title compound (79 mg) as white crystals.

Example 24

2-(3-(4-(6-Fluoroindol-3-yl)piperidyl)propyl)-1,3,4-trihydroisoquinoline Hydrochloride Using 4-(3-(6-fluoro)indolyl)piperidine (175 mg, 0.8 mmol) and 2-(3-chloropropyl)-1,2,3,4-tetrahydroisoquinoline hydrochloride (236 mg, 0.96 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:methanol=20:1) and was then recrystallized from ethyl acetate to afford a free form (176 mg) of the title compound as white crystals. After adding hydrochloric acid/methanol to a solution of the free form in methanol, the mixture was concentrated and was then recrystallized from methanol/ether to afford the title compound (202 mg, yield: 54%) as white crystals.

Example 25

5-Methoxy-3-(4-(3-Piperidylpropyl)-2H,3H,5H-4-azinyl)indole Hydrochloride

Using 4-(3-(5-methoxy)indolyl)-1,2,3,6-tetrahydropyridine (115 mg, 0.50 mmol) and 1-(3-chloropropyl)piperidine hydrochloride (139 mg, 0.70 mmol) instead of 4-(3-indolyl)piperidine and 1-(3-chloropropyl)-3-(4-methoxyphenyl) piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate=1:1) and was then recrystallized from ethyl acetate to afford a free form (108 mg, yield: 61%) of the title compound as pale yellow crystals. After adding hydrochloric acid/methanol to a solution of the free form (80 mg) in methanol, the mixture was concentrated and was then recrystallized from methanol/ether to afford the title compound (40 mg) as white crystals.

Example 26

1-(4-Indol-3-ylpiperidyl)-3-piperidylpropan-1-one Hydrochloride

To a suspended solution of 4-(3-indolyl)piperidine (200 mg, 1.0 mmol) in dichloromethane (15 mL) was added pyridine (5 mL), and the resulting mixture was cooled to 0° C. Subsequently, 3-chloropropionyl chloride (0.25 mL, 2.6 mmol) was then added dropwise to the mixture, and the resulting mixture was stirred at 0° C. for 2 hours. After the reaction mixture was poured into hydrochloric acid and then extracted with ethyl acetate, the ethyl acetate layer was washed with 1 N hydrochloric acid and a saturated aqueous sodium chloride and was dried over anhydrous sodium sulfate. After sodium sulfate was filtered off, the filtrate was concentrated to afford a crude product (100 mg). After identifying the structure of the crude product by $^1$H NMR and IR, piperidine (350 mg, 4.0 mmol) was added to a solution of the crude product in acetonitrile (10 mL), and the mixture was stirred at 80° C. for 3 hours. After concentrating the reaction mixture, water (10 mL) was added thereto, and the resulting mixture was extracted with chloroform. After drying over anhydrous sodium sulfate, the chloroform layer was concentrated, and the resulting crude product was purified by column chromatography on a silica gel (silica gel NH-DM 1020 produced by Fuji Silysia Chemical Ltd., eluent; hexane:ethyl acetate=1:2) to afford a free form (97 mg, yield: 29%) of the title compound as a colorless amorphous solid. After adding hydrochloric acid/methanol to a solution of the free form (67 mg) in methanol, the mixture was concentrated and was then reprecipitated from ethanol/ether to afford the title compound (50 mg) as a pale yellow amorphous solid.

Example 27

(4-Indol-3-ylcyclohexyl)methyl(3-piperidylpropyl) amine Hydrochloride

To a solution of 4-(3-indolyl)cyclohexanone (248 mg, 1.2 mmol) and 1-(3-methylaminopropyl)piperidine (200 mg, 1.3 mmol) in 1,2-dichloroethane (10 mL) was added sodium triacetoxyborohydride (377 mg, 1.8 mmol) and acetic acid (70 mg, 1.2 mmol). After stirring at room temperature for 12 hours, the reaction mixture was diluted with ethyl acetate and was extracted with water. A saturated aqueous sodium hydrogencarbonate was added to the water layer to pH of 11, and the resulting mixture was extracted with chloroform. After drying over anhydrous sodium sulfate, the chloroform layer was concentrated, and the resulting crude product was purified by column chromatography on a silica gel (silica gel NH-DM 1020 produced by Fuji Silysia Chemical Ltd., eluent; ethyl acetate) to afford a free form (341 mg, yield: 80%) of the title compound as a pale red viscous oil. After adding hydrochloric acid/methanol to a solution of the free form (335 mg) in methanol, the mixture was concentrated and was then reprecipitated from methanol/ether to afford the title compound (219 mg) as a white crystalline powder.

Example 28

1(1-(3-Piperidylpropyl)-4-piperidyl)-3-azaindolin-2-one Hydrochloride

Using a 98% 4(1-(2-keto)benzimidazolinyl)piperidine (100 mg, 0.45 mmol) and 1-(3-chloropropyl)piperidine hydrochloride (120 mg, 0.60 mmol) instead of 4-(3-indolyl) piperidine and 1-(3-chloropropyl)-3-(4-methoxyphenyl) piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; ethyl acetate) to afford a free form (107 mg) of the title compound as a colorless amorphous solid. After adding hydrochloric acid/methanol to a solution of the free form in methanol, the mixture was concentrated and was then recrystallized from methanol/ether to afford the title compound (100 mg, yield: 53%) as white crystals.

Example 29

4-Naphthyl-1-(3-Piperidylpropyl)piperidine Hydrochloride

Using 4-(1-naphthyl)piperidine (149 mg, 0.60 mmol) and 1-(3-chloropropyl)piperidine hydrochloride (166 mg, 0.84 mmol) instead of 4-(3-indolyl)piperidine and 1-(3-chloropropyl)-3-(4-methoxyphenyl)piperidine hydrochloride respectively, reaction, extraction, and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate= 2:1) to afford a free form (202 mg) of the title compound as a yellow viscous oil. After adding hydrochloric acid/ methanol to a solution of the free form in methanol, the mixture was concentrated and was then recrystallized from methanol/ether to afford the title compound (85 mg, yield: 35%) as white crystals.

Example 30

2-(3-(4-Naphthylpiperidyl)propyl)isoindoline Hydrochloride

Using 4-(1-naphthyl)piperidine (124 mg, 0.50 mmol) and 2-(3-chloropropyl)isoindoline hydrochloride (139 mg, 0.72 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:methanol=20:1) to afford a free form (158 mg) of the title compound as a yellow viscous oil. After adding hydrochloric acid/methanol to a solution of the free form in methanol, the mixture was concentrated and was then recrystallized from methanol/ ether to afford the title compound (91 mg, yield: 44%) as white crystals.

Example 31

4-(2-Naphthyl)-1-(3-piperidylpropyl)piperidine Hydrochloride

Using 4-(2-naphthyl)piperidine (167 mg, 0.67 mmol) and 1-(3-chloropropyl)piperidine hydrochloride (198 mg, 1.0 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; hexane:chloroform=1:1) to afford a free form (187 mg) of the title compound as a yellow viscous oil. After adding hydrochloric acid/methanol to a solution of the free form in methanol, the mixture was concentrated and was then recrystallized from ethanol to afford the title compound (177 mg, yield: 64%) as white crystals.

Example 32

2-(3-(4-(2-Naphthyl)piperidyl)propyl)isoindoline Hydrochloride

Using 4-(2-naphthyl)piperidine (149 mg, 0.60 mmol) and 2-(3-chloropropyl)isoindoline hydrochloride (209 mg, 0.90 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform) to afford a free form (119 mg) of the title compound as a colorless viscous oil. After adding hydrochloric acid/methanol to a solution of the free form in methanol, the mixture was concentrated and was then recrystallized from ethanol/ethyl acetate to afford the title compound (110 mg, yield: 41%) as white crystals.

Example 33

3-(1-(3-Piperidylpropyl)-4-piperidyl)-2-aza-1-oxaindene Hydrochloride

Using 4-(3-benzisoxazolyl)piperidine (191 mg, 0.80 mmol) and 1-(3-chloropropyl)piperidine hydrochloride (222 mg, 1.1 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate=3:1) to afford a free form (236 mg) of the title compound as a pale yellow viscous oil. After adding hydrochloric acid/methanol to a solution of the free form in methanol, the mixture was concentrated and was then recrystallized from methanol/ether to afford the title compound (277 mg, yield: 86%) as white crystals.

Example 34

(2-Indol-3-ylethyl)methyl(3-piperidylpropyl)amine Hydrochloride

Using 3-(2-methylaminoethyl)indole (123 mg, 0.70 mmol) and 1-(3-chloropropyl)piperidine hydrochloride (198 mg, 1.0 mmol) instead of 4-(3-indolyl)piperidine and 1-(3-chloropropyl)-3-(4-methoxyphenyl)piperidine hydrochloride respectively, reaction and concentration were carried out in the same procedure as Example 2. The resulting crude product was purified by column chromatography on a silica gel (silica gel NH-DM 1020 produced by Fuji Silysia Chemical Ltd., eluent; hexane:ethyl acetate=1:1) to afford a free form (166 mg) of the title compound as a pale yellow viscous oil. After adding hydrochloric acid/methanol to a solution of the free form in methanol, the mixture was concentrated and was then reprecipitated with methanol/ether to afford the title compound (167 mg, yield: 64%) as a pale yellow crystalline powder.

Example 35

3-(1-(3-Piperidylpropyl)-3-piperidyl)indole Hydrochloride

Using 3-(3-indolyl)piperidine (104 mg, 0.44 mmol) and 1-(3-chloropropyl)piperidine hydrochloride (122 mg, 0.62 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform) to afford a free form (125 mg) of the title compound as a pale yellow viscous oil. After adding hydrochloric acid/methanol to a solution of the free form in methanol, the mixture was concentrated and was then freeze-dried to afford the title compound (129 mg, yield: 74%) as a white amorphous solid.

Example 36

3-(1-(3-Piperidylpropyl)-4-piperidyl)oxaindene Hydrochloride

Using 3-(3-benzofuranyl)piperidine (152 mg, 0.64 mmol) and 1-(3-chloropropyl)piperidine hydrochloride (178 mg, 0.90 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:methanol=20:1) to afford a free form (238 mg) of the title compound as a colorless viscous oil. After adding hydrochloric acid/methanol to a solution of the free form in methanol, the mixture was concentrated and was then recrystallized from methanol/ether to afford the title compound (235 mg, yield: 92%) as white crystals.

Example 37

2-(6-(4-Indol-3-ylpiperidyl)hexyl)isoindoline-1,3-dione Hydrochloride

Using N-(6-bromohexyl)phthalimide (682 mg, 2.2 mmol) instead of 1-(3-chloropropyl)-3-(4-methoxyphenyl)piperidine hydrochloride, reaction and concentration were carried out in the same procedure as Example 2. The resulting crude product was purified by column chromatography on a silica gel (silica gel NH-DM 2035 produced by Fuji Silysia Chemical Ltd., eluent; chloroform:hexane=1:1) and was then recrystallized from ethyl acetate/hexane to afford a free form (359 mg, yield: 42%) of the title compoundas pale yellow crystals. After adding hydrochloric acid/methanol to a solution of the free form (186 mg) in methanol, the mixture was concentrated and was then recrystallized from methanol/ether to'afford the title compound (174 mg) as pale orange crystals.

Example 38

2-(2-(4-Indol-3-ylpiperidyl)ethyl)isoindoline-1,3-dione Hydrochloride

Using N-(2-bromoethyl)phthalimide (559 mg, 2.2 mmol) instead of 1-(3-chloropropyl)-3-(4-methoxyphenyl)piperidine hydrochloride, reaction and concentration were carried out in the same procedure as Example 2. The resulting crude product was purified by column chromatography on a silica gel (silica gel NH-DM 1020 produced by Fuji Silysia Chemical Ltd., eluent; chloroform:hexane=1:4) and was then recrystallized from ethyl acetate/hexane to afford a free form (468 mg, yield: 63%) of the title compound as pale yellow crystals. After adding hydrochloric acid/methanol to a solution of the free form (172 mg) in methanol, the mixture was concentrated and was then recrystallized from methanol/ether to afford the title compound (152 mg) as colorless crystals.

Example 39

2-(4-(4-(6-Fluoroindol-3-yl)piperidyl)butyl)isoindoline-1,3-dione Hydrochloride

Using 4-(3-(6-fluoro)indolyl)piperidine (437 mg, 2.0 mmol) and N-(4-bromobutyl)phthalimide (677 mg, 2.4 mmol) instead of 4-(3-indolyl)piperidine and 3-dimethylaminopropyl chloride hydrochloride respectively, reaction, extraction, and concentrationwere carried out in the same procedure as Example 4. The resulting crude product was purified by column chromatography on a silica gel (silica gel NH-DM 1020 produced by Fuji Silysia Chemical Ltd., eluent; chloroform:methanol=20:1) to afford a free form (756 mg, yield: 90%) of the title compound as a yellow viscous oil. After adding hydrochloric acid/methanol to a solution of the free form (100 mg) in methanol, the mixture was concentrated and was then recrystallized from methanol/ether to afford the title compound (85 mg) as yellow crystals.

Example 40

6-Fluoro-3-(1-(4-Isoindolin-2-ylbutyl)-4-piperidyl)indole Hydrochloride

Using a free form of 2-(4-(4-(6-fluoroindol-3-yl)piperidyl)butyl)isoindoline-1,3-dione (135 mg, 0.32 mmol) instead of 1-(4-(4-indol-3-ylpiperidyl)butyl)piperidin-2-one, reaction, filtration, and concentration were carried out in the same procedure as Example 12. The resulting crude product was purified by column chromatography on a silica gel (silica gel NH-DM 1020 produced by Fuji Silysia Chemical Ltd., eluent; chloroform) to afford a free form (81 mg, yield: 65%) of the title compound as a white solid. After adding hydrochloric acid/methanol to a solution of the free form (50 mg) in methanol, the mixture was concentrated and was then freeze-dried to afford the title compound (54 mg) as a yellow amorphous solid.

Example 41

2-(4-(4-Indol-3-ylpiperidyl)butyl)-1,3,4-trihydroisoquinoline Hydrochloride

Using 1-(2-1,3,4-trihydroisoquinolyl)-4-chlorobutan-1-one (285 mg, 1.2 mmol) instead of 3-dimethylaminopropyl chloride hydrochloride, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:hexane=1:1). to afford an amide (95 mg, yield: 24%) as a colorless oil. After identifying the structure by $^1$H NMR and IR, the amide was subjected to reduction, filtration, and concentration in the same procedure as Example 12. The resulting crude product was purified by column chromatography on a silica gel (silica gel NH-DM 1020 produced by Fuji Silysia Chemical Ltd., eluent; chloroform) to afford a free form (63 mg) of the title compound as a colorless oil. After adding hydrochloric acid/methanol to a solution of the free form in methanol, the mixture was concentrated and was then freeze-dried to afford the title compound (63 mg, yield: 57%) as a yellow amorphous solid.

Reference Example 22

6-Fluoro-3-(1-(3-Cyanopropyl)-4-piperidyl)indole

Using 4-(3-(6-fluoro)indolyl)piperidine hydrochloride (1.02 g, 4.0 mmol) and 4-bromobutyronitrile (715 mg, 4.8 mmol) instead of 4-(3-indolyl)piperidine and 3-dimethylaminopropyl chloride hydrochloride respectively, reaction, extraction, and concentration were carried out in the same procedure as Example 4. The resulting crude product was purified by column chromatography on a silica gel (silica gel NH-DM 1020 produced by Fuji Silysia Chemical Ltd., eluent; chloroform:methanol=20:1) to afford the title compound (1;.18 g, yield: 83%) as yellow crystals. The crystals (1.08 g) were then recrystallized from hexane/ethyl acetate to afford, the title compound (370 mg) as yellow crystals.

Example 42

6-Fluoro-3-(1-(4-Guanidinobutyl)-4-piperidyl)indole Hydrochloride

To a solution of 6-fluoro-3-(1-(3-cyanopropyl)-4-piperidyl)indole (453 mg, 1.6 mmol) in ethanol (30 mL) was added platinum oxide (110 mg) and a concentrated hydrochloric acid (0.8 mL), and the resulting mixture was stirred under hydrogen atmosphere at room temperature overnight. After filtrating the reaction mixture through Celite, the filtrate was concentrated, and a saturated aqueous sodium hydrogencarbonate was added to pH of 10, and the resulting mixture was extracted with chloroform. After drying over anhydrous sodium sulfate, the chloroform layer was concentrated to afford 6-fluoro-3-(1-(4-aminobutyl)-4-piperidyl)indole (470 mg, yield: 100%) as a pale yellow solid. To a solution of this amine (68 mg, 0.23 mmol) in DMF (0.22 mL) was added lH-pyrazole-1-carboxamidine hydrochloride (35 mg, 0.23 mmol) and diisobutylethylamine (31 mg, 0.23 mmol), and the mixture was stirred at room temperature overnight. After washing with diethyl ether, the reaction mixture was purified by column chromatography on a silica gel (silica gel NH-DM 1020 produced by Fuji Silysia Chemical Ltd., eluent; chloroform:methanol=4:1) to afford a free form (61 mg, yield: 77%) of the title compound as a yellow viscous oil. After adding hydrochloric acid/methanol to a solution of the free form (61 mg) in methanol was concentrated and was then freeze-dried to afford the title compound (53 mg) as a white amorphous solid.

Example 43

6-Fluoro-3-(1-(4-Benzylaminobutyl)-4-piperidyl)indole Hydrochloride

In the same manner as in Example 42, 6-fluoro-3-(1-(4-aminobutyl)-4-piperidyl)indole (58 mg, 0.20 mmol) was prepared. Using this amine and benzaldehyde (21 mg, 0.20 mmol) instead of 1-(3-methylaminopropyl)piperidine and 4-(3-indolyl)cyclohexanone respectively, reaction, extraction, and concentration: were carried out in the same procedure as Example 27. The resulting crude product was purified by column chromatography on a silica gel (eluent; ammonia-saturated chloroform:methanol=30:1) to afford a free form (40 mg, yield: 52%) of the title compound as a yellow viscous oil. After adding hydrochloric acid/methanol to a solution of the free form (28 mg) in methanol, the mixture was concentrated and was then freeze-dried to afford the title compound (32 mg) as a pale brown amorphous substance.

Structural formulae and spectra data of the invented compounds listed in the above reference examples and examples are shown in the following tables.

| | | |
|---|---|---|
| REFERENCE EXAMPLE 1 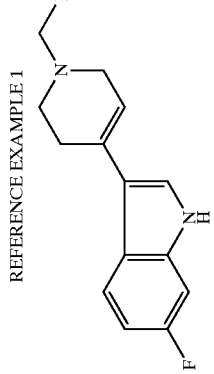 | H NMR(ppm)(300MHz, CDCl3) free form 2.54~2.62(2H, m), 2.74(2H, t, J=5.8Hz), 3.24(2H, dd, J=2.5, 5.8Hz), 3.66(2H, s), 6.14~6.19(1H, m), 6.90(1H, ddd, J=2.2, 8.8, 9.3Hz), 7.03(1H, dd, J=2.2, 9.3Hz), 7.13(1H, d, J=2.2Hz), 7.27~7.43(5H, m), 7.79(1H, dd, J=5.2, 8.8Hz), 8.00~ MS(EI) 306M+ | IR(cm−1)(KBr) free form 2818,1623, 1532, 1458, 1341, 1302, 1232, 1116, 955, 804, 700 m.p. free form 160° C. decomposition |
| REFERENCE EXAMPLE 2 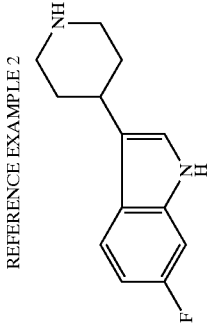 | H NMR(ppm)(300MHz, CD3OD) free form 1.85~2.04(2H, m), 2.20~2.30(2H, brd), 3.10~3.30(3H, m), 3.45~3.55(2H, brd), 6.80(1H, ddd, J=2.4, 8.8, 9.8Hz), 7.04(1H, dd, J=2.4, 9.8Hz), 7.08(1H, d, J=0.8Hz), 7.56(1H, dd, J=5.2, 8.8Hz) MS(EI) 218M+ | IR(cm−1)(KBr) free form 3291, 2826, 1625, 1548, 1461, 1341, 1271, 1156, 1105, 1011,951, 795 m.p. free form 214° C. |
| REFERENCE EXAMPLE 3 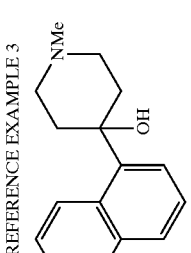 | H NMR(ppm)(300MHz, CDCl3) free form 1.97(1H, brs), 2.21~2.41(7H, m), 2.62(2H, dt, J=2.7, 11.5Hz), 2.77~2.81(2H, brd), 7.39~7.57(4H, m), 7.78(1H, d, J=8.2Hz), 7.85~7.88(1H, m), 8.88~8.92(1H, m) MS(EI) 241M+ | IR(cm−1)(KBr) free form 3045, 2967, 1619, 1507, 1468, 1278, 1156, 1132, 1060, 776 m.p. 181° C. |
| REFERENCE EXAMPLE 4 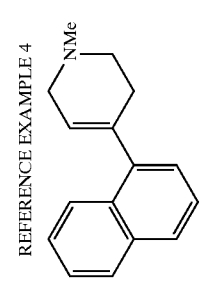 | H NMR(ppm)(300MHz, CDCl3) free form 2.48(3H, s), 2.57~2.61(2H, m), 2.74~2.77(2H, m), 3.19(2H, dd, J=3.3, 6.0Hz), 5.75(1H, dt, J=1.6, 3.3Hz), 7.28~7.31(1H, m), 7.40~7.49(3H, m), 7.75(1H, d, J=8.2Hz), 7.83~7.86(1H, m), 8.02~ 8.05(1H, m) MS(EI) 225M+ | IR(cm−1)(KBr) free form 3398, 3053, 2785, 1642, 1591, 1507, 1461,1396, 1377, 1265, 1075, 1017 m.p. ° C. |
| REFERENCE EXAMPLE 5 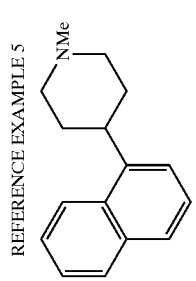 | H NMR(ppm)(300MHz, CDCl3) free form 1.88~2.02(4H, m), 2.22(2H, dt, J=3.6, 11.5Hz), 2.38(3H, s), 3.03~3.09(2H, brd), 3.28~3.33(1H, m), 7.41~7.54(4H, m), 7.72(1H, dd, J=7.4, 9.4Hz), 7.85~7.88(1H, m), 8.10(1H, d, J=8.0Hz) MS(EI) 225M+ | IR(cm−1)(KBr) free form 3347, 2951, 2672, 1631, 1510, 1454, 1401, 1258, 1159, 1051,968, 801 m.p. free form 245° C. |

-continued

| | | |
|---|---|---|
| REFERENCE EXAMPLE 6<br>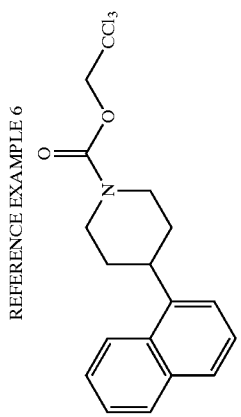 | H NMR(ppm)(300MHz, CDCl3) free form 1.84(2H, ddd, J=4.1, 12.3, 12.8Hz), 2.05~2.09(2H, brd), 3.09~3.17(1H, m), 3.51~3.56(1H, m), 4.43~4.47(2H, brd), 4.80(2H, d, J=4.7Hz), 7.34~7.57(4H, m), 7.75(1H, d, J=8.2Hz), 7.88(1H, d, J=8.2Hz), 8.09(1H, d, J=8.2Hz) MS(EI) 385M+ | IR(cm−1)(neat) free form 3414, 3049, 2947, 2858,1774, 1714, 1598, 1510, 1437, 1275, 1223, 1127, 1098, 1061, 993 m.p. ° C. |
| REFERENCE EXAMPLE 7<br>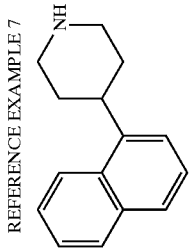 | H NMR(ppm)(300MHz, CDCl3) free form 1.81(2H, ddd, J=3.6, 11.7, 12.2Hz), 1.98~2.02(2H, brd), 2.92(2H, dt, J=2.5, 12.2Hz), 3.25~3.29(2H, m), 3.46(1H, tt, J=3.3, 11.7Hz), 7.40~7.55(4H, m), 7.72(1H, d, J=7.7Hz), 7.87(1H, d, J=7.4Hz), 8.12(1H, d, J=8.0Hz) MS(EI) 211M+ | IR(cm−1)(KBr) free form 2952, 2795, 2509, 1592, 1509,1450, 1396, 1075, 996, 955, 796, 773, 550 m.p. HCl salt 285° C. |
| REFERENCE EXAMPLE 8<br>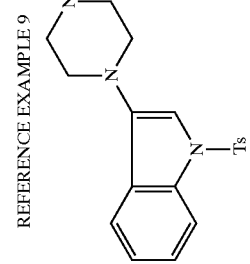 | H NMR(ppm)(300MHz, CDCl3) 2.35(3H, s), 7.23(1H, d, J=0.8Hz), 7.24~7.41(3H, m), 7.47~7.52(1H, m), 7.62(1H, s), 7.78(2H, d, J=8.5Hz), 7.99(1H, d, J=8.5Hz) MS(EI) 349+ | IR(cm−1)(KBr) free form 3130, 1594, 1441, 1376, 1265, 1174, 1126, 1088, 1029, 929, 755, 704, 658 m.p. 108~111° C. |
| REFERENCE EXAMPLE 9<br>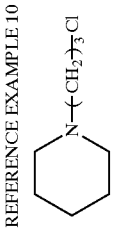 | H NMR(ppm)(300MHz, CDCl3) free form 2.32(3H, s), 3.00~3.10(8H, m), 6.96(1H, s), 7.14~7.34(4H, m), 7.50(1H, d, J=8.0Hz), 7.66~7.74(2H, m), 8.03(1H, d, J=8.0Hz) MS(EI) 355M+ | IR(cm−1)(neat) free form 2921, 2825, 1668, 1593, 1565, 1492, 1449, 1363, 1264, 1218, 1172, 1128, 1103 m.p. ° C. |
| REFERENCE EXAMPLE 10<br>N-(CH₂)₃-Cl (piperidine) | H NMR(ppm)(300MHz, CDCl3) HCl salt 1.34~1.52(1H, m), 1.81~1.99(3H, m), 2.22~2.41(2H, m), 2.43~2.54(2H, m), 2.59~2.74(2H, m), 3.06~3.16(2H, m), 3.50~3.61(2H, brd), 3.68(2H, t, J=5.8Hz) MS(FAB) 162(M+H)+ | IR(cm−1)(KBr) HCl salt 2950, 2699, 2643, 2544, 2526, 1457, 1389, 1312, 1288, 1225, 1156, 1079, 1013, 971, 955, 797,651, 585 m.p. HCl salt 218° C. |

| | -continued | |
|---|---|---|
| REFERENCE EXAMPLE 11 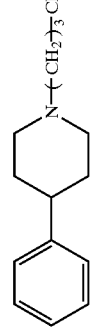 | H NMR(ppm)(300MHz, CDCl3) HCl salt 1.98~2.10(2H, brd), 2.48~2.90(7H, m), 3.12~3.23(2H, m), 3.70(2H, t, J=5.8Hz), 7.20~7.40(5H, m) MS(FAB) 238(M+H)+ | IR(cm−1)(KBr) HCl salt 2925, 2461, 1493, 1473, 1457, 1410, 1387, 1266, 1179, 1083, 1044, 972, 956, 781, 751, 733, 698 m.p. HCl salt 174–175° C. |
| REFERENCE EXAMPLE 12 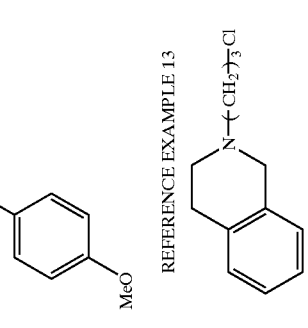 | H NMR(ppm)(300MHz, CD3OD) free form 1.54~1.72(1H, m), 1.94~2.24(3H, m), 2.76~2.96(2H, m), 3.12~3.26(1H, brt), 3.44~3.62(2H, m), 3.79(3H, s), 6.85(2H, dt, J=9.6, 2.7Hz), 7.12(2H, dt, J=9.6, 2.7Hz) MS(FAB) 192(M+H)+ | IR(cm−1)(KBr) HCl salt 2951, 2675, 2621, 2556, 2507, 1612, 1584, 1514, 1457, 1305, 1271, 1246, 1181, 1105,1030, 963, 831, 659, 542 m.p. HCl salt 144° C. |
| REFERENCE EXAMPLE 13 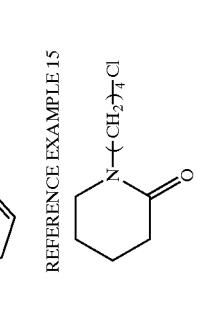 | H NMR(ppm)(300MHz, CDCl3) free form 2.06(2H, tt, J=6.6, 6.6Hz), 2.66(2H, t, J=6.6Hz), 2.74(2H, t, J=6.0Hz), 2.90(2H, t, J=6.0Hz), 3.64(2H, s), 3.65(2H, t, J=6.6Hz), 6.99~7.05(1H, m), 7.06~7.16(3H, m) MS(FAB) 210(M+H)+ | IR(cm−1)(KBr) HCl salt 2917, 2663, 2573, 2477, 2411, 1498, 1454, 1425, 1332, 1271, 1050, 916, 820,755, 657 m.p. HCl salt 188–189° C. |
| REFERENCE EXAMPLE 14 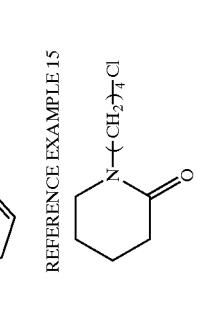 | H NMR(ppm)(300MHz, CDCl3) free form 2.07(2H, tt, J=6.6, 6.6Hz), 2.97(2H, t, J=8.2Hz), 3.24(2H, t, J=6.6Hz), 3.35(2H, t, J=8.2Hz), 3.68(2H, t, J=6.6Hz), 6.51(1H, d, J=7.4Hz), 6.66(1H, dt, J=0.8, 7.4Hz), 7.04~7.11(2H, m) MS(FAB) 196(M+H)+ | IR(cm−1)(KBr) HCl salt 2860, 2437, 2400, 2234, 1485, 1461, 1406, 1098, 754, 733,604, 542 m.p. HCl salt 152–154° C. |
| REFERENCE EXAMPLE 15 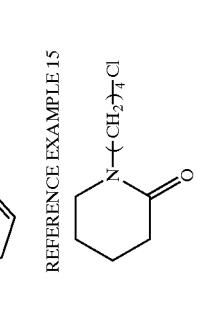 | H NMR(ppm)(300MHz, CDCl3) 1.64~1.86(8H, m), 2.34~2.42(2H, m), 3.24~3.31(2H, m), 3.40(2H, t, J=7.1Hz), 3.58(2H, t, J=6.3Hz) MS(EI) 189M+ | IR(cm−1)(neat) free form 2943, 2867, 1637, 1494, 1447, 1418, 1352, 1328, 1301, 1232, 1169, 1146 m.p.  ° C. |

-continued

| | | |
|---|---|---|
| REFERENCE EXAMPLE 16 | 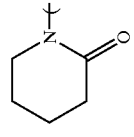 | H NMR(ppm)(300MHz, CDCl3) 1.38–1.64(4H, m), 1.72–1.87(6H, m), 2.32–2.42(2H, m), 3.23–3.31(2H, m), 3.36(2H, t, J=7.1Hz), 3.54(2H, t, J=6.6Hz) MS(EI) 203M+ | IR(cm−1)(neat) free form 2938, 2862, 1637, 1494, 1465, 1447, 1418, 1352, 1329, 1299, 1265, 1220, 1169 m.p. ° C. |
| REFERENCE EXAMPLE 17 | 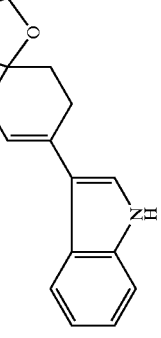 | H NMR(ppm)(300MHz, CDCl3) free form 1.96(2H, t, J=6.6Hz), 2.53(2H, t, J=1.9Hz), 2.68–2.75(2H, m), 4.05(4H, s), 6.14–6.17(1H, m), 7.11–7.22(2H, m), 7.34–7.37(1H, m), 7.89(1H, d, J=8.0Hz), 7.94–8.18(1H, brs) MS(EI) 255M+ | IR(cm−1)(KBr) free form 3293, 2884, 1437, 1349, 1237, 1124, 1059, 1017, 864,736 m.p. free form 183–186° C. |
| REFERENCE EXAMPLE 18 | 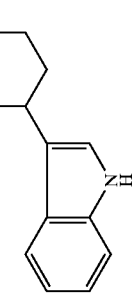 | H NMR(ppm)(300MHz, CDCl3) free form 1.92–2.06(2H, m), 2.40–2.65(6H, m), 3.35(1H, tt, J=3.6, 11.5Hz), 6.99(1H, d, J=2.2Hz), 7.11–7.25(2H, m), 7.37(1H, dd, J=0.8, 8.0Hz), 7.66(1H, ddd, J=0.8, 1.3, 8.0Hz), 7.97–8.20(1H, brs) MS(EI) 213M+ | IR(cm−1)(KBr) free form 3328, 2942, 1700, 1458, 1430, 1343, 1227, 1165, 1106, 1010, 944,828, 803, 751 m.p. free form 114–116° C. |
| REFERENCE EXAMPLE 19 | 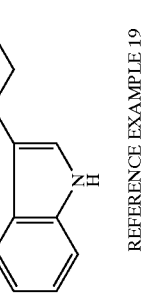 | H NMR(ppm)(300MHz, CDCl3) free form 1.43–1.47(2H, m), 1.56–1.61(4H, m), 1.69–1.81(2H, m), 2.19(3H, s), 2.31–2.43(8H, m), 3.48(2H, s), 7.22–7.32(5H, m) MS(EI) 246M+ | IR(cm−1)(KBr) HCl salt 3421, 2947, 2642, 2511, 1456, 1312, 1224, 1079, 1014, 970, 927, 751, 698 m.p. HCl salt 157–163° C. |
| REFERENCE EXAMPLE 20 | 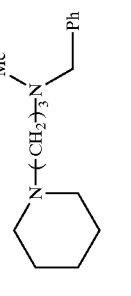 | H NMR(ppm)(300MHz, CDCl3) free form 1.41–1.46(2H, m), 1.54–1.62(4H, m), 1.64–1.74(2H, m), 1.91(1H, brs), 2.32–2.37(6H, m), 2.43(3H, s), 2.61(2H, t, J=6.9Hz) MS(EI) 156M+ | IR(cm−1)(KBr) HCl salt 3432, 2943, 2511, 1614, 1593, 1458, 1331, 1202, 1141, 1082, 1054, 1019, 967, 950 m.p. HCl salt 255° C. decomposition |

-continued

| | H NMR / MS | IR / Analysis |
|---|---|---|
| REFERENCE EXAMPLE 21 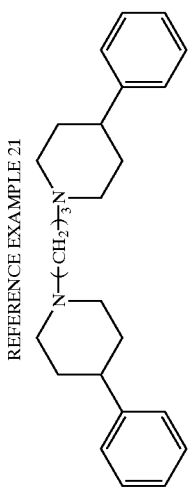 | H NMR(ppm)(300MHz, CDCl3) free form 1.72~1.90(10H, m), 2.05(4H, dt, J=11.0, 3.6Hz), 2.36~2.56(6H, m), 3.06(4H, d, J=11.5Hz), 7.20~7.35(10H, m) MS(EI) 362M+ | IR(cm−1)(KBr) HCl salt 3430, 2925, 2641, 2534, 2373, 1601, 1492, 1447, 1244, 1168, 1054, 950, 789, 757, 703 m.p. HCl salt 230° C. |
| REFERENCE EXAMPLE 22 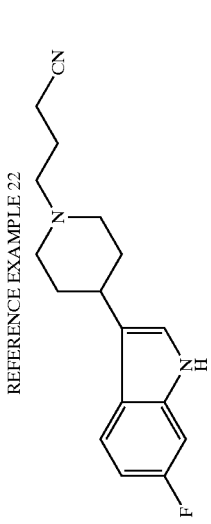 | H NMR(ppm)(300MHz, CDCl3) free form 1.70~1.91(4H, m), 2.00~2.06(2H, brd), 2.15(2H, dt, J=2.2, 12.1Hz), 2.45(2H, t, J=7.1Hz), 2.50(2H, t, J=7.1Hz), 2.79(1H, tt, J=3.8, 12.1Hz), 2.97~3.01(2H, brd), 6.87(1H, ddd, J=0.8, 8.7, 9.6Hz), 6.94(1H, dd, J=0.8, 2.2Hz), 7.04(1H, dd, J=2.2, 2.2Hz) MS(EI) 285M+ | IR(cm−1)(KBr) free form 2952,2914, 2808, 2244, 1856, 1735, 1624, 1551, 1461, 1343, 1315, 1249, 1221, 1143, 1116, 1103, 1024, 990, 976, 950, 842, 795 m.p. ° C. |
| EXAMPLE 1 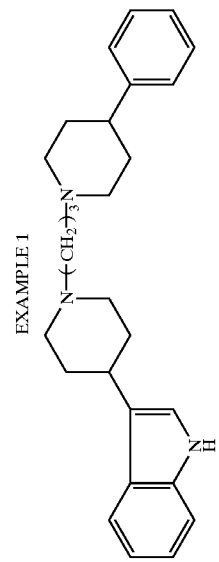 | H NMR(ppm)(300MHz, CDCl3) free form 1.72~1.92(8H, m), 1.96~2.20(6H, m), 2.36~2.56(5H, m), 2.78~2.92(1H, m), 3.08(4H, d, J=11.3Hz), 6.95(1H, d, J=1.6Hz), 7.06~7.37(8H, m), 7.65(1H, d, J=8.0Hz), 8.04~8.26(1H, brd) IR(cm−1)(KBr) HCl salt 3420, 2926, 2637, 1618, 1494, 1458, 1429, 1339, 1231, 1106, 948, 745, 700 | MS(FAB) 402(M+H)+ Elemental Analysis Compositional Formula C27H35N3.2HCl.H2O Calcd C 65.84; H 7.98; N 8.53; Cl 14.40 Found C 65.76; H 7.89; N 8.45; Cl 14.56 m.p. HCl salt 210° C. decomposition |
| EXAMPLE 2 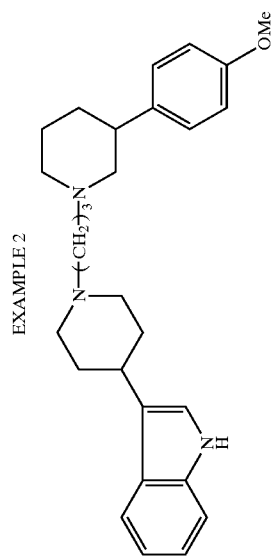 | H NMR(ppm)(300MHz, CDCl3) free form 1.41(1H, dq, J=12.2, 4.5Hz), 1.62~2.20(13H, m), 2.4(4H, dt, J=8.0, 2.7Hz), 2.72~2.89(2H, m), 2.95~3.11(4H, m), 3.78(3H, s), 6.84(2H, dt, J=9.6, 2.7Hz), 6.95(1H, d, J=2.2Hz), 7.09(1H, dt, J=8.0, 1.1Hz), 7.13~7.20(3H, m), 7.34(1H, d, J=8.0Hz), 7.64(1H, d, J=8.0Hz), 8.15~8.25(1H, brs) IR(cm−1)(KBr)HCl salt 3388, 2944, 2640, 1611, 1515, 1458, 1339, 1247, 1182, 1106, 1029, 948, 833, 750, 549 | MS(FAB) 432(M+H)+ Elemental Analysis Compositional Formula C28H37N3O.2HCl.2.8H2O Calcd C 60.60; H 8.10; N 7.57; Cl 12.78 Found C 60.56; H 8.05; N 7.58; Cl 12.92 m.p. ° C. |

-continued

| | | |
|---|---|---|
| EXAMPLE 3 | H NMR(ppm)(300MHz, CDCl3) free form 1.43~1.47(2H, m), 1.56~1.63(4H, m), 1.71~1.89(4H, m), 2.04~2.16(4H, m), 2.31~2.40(8H, m), 2.84(1H, tt, J=3.6, 11.9Hz), 3.04~3.08(2H, brd), 6.97(1H, d, J=1.6Hz), 7.07~7.21(2H, m), 7.35(1H, dd, J=0.8, 7.9Hz), 7.65(1H, dd, J=0.8, 7.9Hz), 7.98-8.12(1H, brs) IR(cm−1)(KBr) HCl salt 3496, 3303, 2934,2688, 2553, 1638, 1459, 1425, 1232, 1015, 945, 741, 546 | MS(FAB) 326(M+H)+ Elemental Analysis Compositional Formula C21H31N3.2HCl.H2O Calcd C 62.60; H 8.38; N 10.43; Cl 17.60 Found C 62.52; H 8.29; N 10.32; Cl 17.37 m.p. HCl salt 227° C. decomposition |
| EXAMPLE 4 | H NMR(ppm)(300MHz, CDCl3) free form 1.69~1.89(4H, m), 2.01~2.08(4H, m), 2.12~2.18(6H, m), 2.32(2H, t, J=7.4Hz), 2.39~2.46(2H, m), 2.84(1H, tt, J=3.6, J=11.8Hz), 3.05~3.09(2H, brd), 6.97(1H, d, J=2.2Hz), 7.09(1H, dt, J=1.1, 7.1Hz), 7.18(1H, dt, J=1.1, 7.1Hz), 7.35(1H, d, J=7.1Hz), 7.65(1H, d, J=7.1Hz), 8.35~8.53(1H, brs) IR(cm−1)(neat)free form 3418, 3146, 3012, 2930, 2778, 1458, 1377, 1342, 1249, 1222, 1116 | MS(EI) 285M+ Elemental Analysis Compositional Formula C18H27N3.2HCl Calcd C 60.33; H 8.16; N 11.73; Cl 19.79 Found C 60.02; H 8.08; N 11.45; Cl 19.76 m.p. HCl salt 240° C. decomposition |
| EXAMPLE 5 | H NMR(ppm)(300MHz, CDCl3) free form 1.77~1.93(4H, m), 2.05~2.19(4H, m), 2.46~2.51(2H, m), 2.57(2H, t, J=7.4Hz), 2.75(2H, t, J=5.8Hz), 2.80~2.93(3H, m), 3.08~3.12(2H, brd), 3.65(2H, s), 6.96(1H, d, J=2.2Hz), 7.01~7.20(6H, m), 7.24(1H, d, J=8.0Hz), 7.65(1H, d, J=8.0Hz), 8.05~8.20(1H, brs) IR(cm−1)(KBr) HCl salt 3050, 2944, 2806,2756, 1618, 1498, 1454, 1374, 1340, 1257, 1223, 1136, 1092, 1075, 1031, 1009, 933, 740 | MS(EI) 373M+ Elemental Analysis Compositional Formula C25H31N3.2HCl.H2O Calcd C 64.45; H 7.59; N 7.38; Cl 8.98 Found C 64.65; H 7.38; N 8.98 m.p. HCl salt 166° C. |
| EXAMPLE 6 | H NMR(ppm)(300MHz, CDCl3) free form 1.77~1.91(4H, m), 2.05~2.19(4H, m), 2.51(2H, t, J=8.0Hz), 2.89(1H, tt, J=3.6, 11.6Hz), 2.95(2H, t, J=8.2Hz), 3.07~3.14(4H, m), 3.34(2H, t, J=8.2Hz), 6.49(1H, t, J=8.0Hz), 6.64(1H, dt, J=0.8, 8.2Hz), 6.93(1H, d, J=1.4Hz), 7.04~7.23(4H, m), 7.32(1H, d, J=8.0Hz), 7.65(1H, d, J=8.0Hz), 8.04~8.18(1H, brs) IR(cm−1)(KBr) HCl salt 3399, 3054, 2921, 2497, 1618, 1489, 1460, 1430, 1340, 1235, 1151, 1097, 1052, 1013, 954 | MS(EI) 359M+ Elemental Analysis Compositional Formula C24H29N3.1.85HCl.0.2H2O Calcd C 66.95; H 7.32; N 9.76; Cl 15.20 Found C 66.90; H 7.22; N 9.67; Cl 15.23 m.p. HCl salt 233° C. |

-continued

| | | |
|---|---|---|
| EXAMPLE 7 | 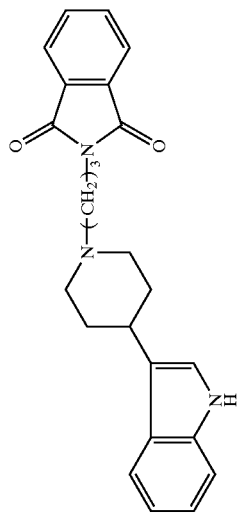 | H NMR(ppm)(300MHz, CDCl3) free form 1.54–1.66(4H, m), 1.88–2.09(6H, m), 2.47(2H, t, J=7.2Hz), 2.71–2.80(1H, m), 2.98–3.02(2H, brd), 3.79(2H, t, J=6.9Hz), 6.86(1H, d, J=2.2Hz), 7.08(1H, dt, J=1.1, 7.9Hz), 7.17(1H, dt, J=1.1, 7.9Hz), 7.35(1H, d, J=7.9Hz), 7.58(1H, d, J=7.9Hz), 7.68–7.74(2H, m), 7.82–7.88(2H, m), 7.88–8.00(1H,brs) IR(cm−1)(KBr) HCl salt 3395, 2953, 2485, 1769, 1706, 1618, 1459, 1396, 1339, 1231, 1103, 1040, 964, 892, 751, 720, 605, 531 | MS(EI) 387M+ Elemental Analysis Compositional Formula C24H25N3O2.HCl Calcd C 68.00; H 6.18; N 9.91; Cl 8.36 Found C 67.62; H 6.21; N 9.96; Cl 8.41 m.p. HCl salt 237° C. decomposition |
| EXAMPLE 8 | 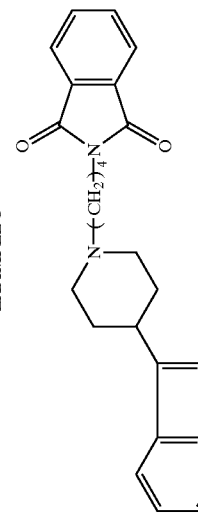 | H NMR(ppm)(300MHz, CDCl3) free form 1.54–1.86(6H, m), 2.02–2.15(4H, m), 2.39–2.44(2H, m), 2.79–2.87(1H, m), 3.02–3.06(2H, brd), 3.71–3.75(2H, m), 6.96(1H, d, J=2.5Hz), 7.07–7.20(2H, m), 7.35(1H, d, J=8.2Hz), 7.64(1H, d, J=7.7Hz), 7.70–7.74(2H, m), 7.81–7.87(2H, m), 7.94–8.06(1H, brs) IR(cm−1)(KBr) HCl salt 3421, 2935, 2365, 1771,1714, 1559, 1457, 1437, 1401, 1062, 749, 722, 617, 530 | MS(EI) 401M+ Elemental Analysis Compositional Formula C25H27N3O2.HCl Calcd C 68.56; H 6.44; N 9.59; Cl 8.10 Found C 68.18; H 6.52; N 9.48; Cl 8.06 m.p. HCl salt 220° C. decomposition |
| EXAMPLE 9 | 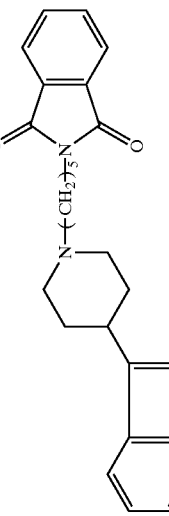 | H NMR(ppm)(300MHz, CDCl3) free form 1.33–1.43(2H, m), 1.57–1.86(6H, m), 2.03–2.14(4H, m), 2.35–2.40(2H, m), 2.83(1H, tt, J=3.6, 11.8Hz), 3.03–3.06(2H, brd), 3.70(2H, t, J=7.4Hz), 6.96(1H, d, J=2.2Hz), 7.09(2H, dt, J=1.1, 7.9Hz), 7.17(1H, dt, J=1.1, 7.9Hz), 7.68–7.74(2H, m), 7.81–7.88(2H, m), 7.98–8.12(1H, brs) IR(cm−1)(neat)free form 3412, 2940, 2864, 2812, 2776, 1773, 1715, 1618, 1468, 1458, 1439, 1400, 1375, 1340 | MS(EI) 415M+ Elemental Analysis Compositional Formula C26H29N3O2.HCl Calcd C 69.09; H 6.69; N 9.30; Cl 7.84 Found C 68.90; H 6.68; N 9.22; Cl 7.84 m.p. HCl salt 217° C. |
| EXAMPLE 10 | 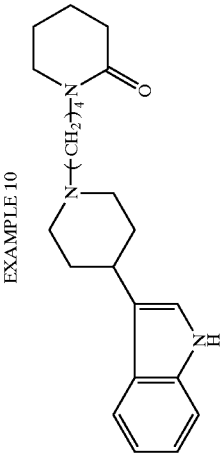 | H NMR(ppm)(300MHz, CDCl3) free form 1.56–1.58(4H, m), 1.71–1.88(6H, m), 2.04–2.14(4H, m), 2.36–2.43(4H, m), 2.84(1H, tt, J=3.8, 12.1Hz), 3.03–3.07(2H, brd), 3.26–3.28(2H, m), 3.37–3.42(2H, m), 6.97(1H, d, J=1.9Hz), 7.07–7.21(2H, m), 7.36(1H, d, J=8.0Hz), 7.65(1H, d, J=7.7Hz), 7.98–8.14(1H, brs) IR(cm−1)(KBr) HCl salt 3197, 2936, 2635, 1635,1496, 1458, 1354, 1289, 1241, 1178, 953, 745 | MS(EI) 353M+ Elemental Analysis Compositional Formula C22H31N3O.HCl.0.1H2O Calcd C 67.45; H 8.28; N 10.73; Cl 9.05 Found C 67.27; H 8.15; N 10.60; Cl 9.26 m.p. HCl salt 201° C. |

-continued

| | | |
|---|---|---|
| EXAMPLE 11 | 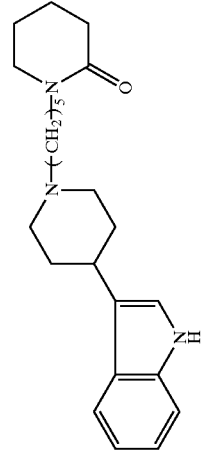 | H NMR(ppm)(300MHz, CDCl3) free form 1.26~1.38(2H, m), 1.53~1.63(4H, m), 1.73~1.89(6H, m), 2.04~2.14(4H, m), 2.35~2.40(4H, m), 2.84(1H, tt, J=3.6, 10.7Hz), 3.25~3.29(2H, m), 3.36(2H, t, J=7.7Hz), 6.98(1H, d, J=1.9Hz), 7.09(1H, dt, J=1.1, 8.0Hz), 7.18(1H, dt, J=1.1, 6.8Hz), 7.35(1H, dd, J=0.8, 8.0Hz), 7.65(1H, d, J=8.0Hz), 7.92~8.06(1H,brs) IR(cm-1)(KBr) free form 3215, 2944, 2815, 2366, 1627, 1496, 1458, 1417, 1345, 1237, 1104, 746 | MS(EI) 367M+ Elemental Analysis Compositional Formula C23H33N3O.H2O Calcd C 71.65; H 9.15; N 10.90 Found C 71.68; H 9.39; N 10.73 m.p. free form 65° C. |
| EXAMPLE 12 | 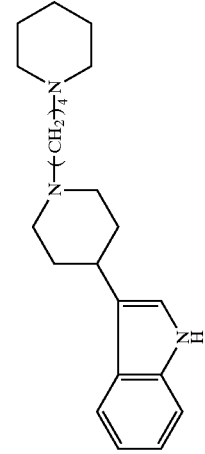 | H NMR(ppm)(300MHz, CDCl3) free form 1.43~1.47(2H, m), 1.52~1.63(8H, m), 1.75~1.89(2H, m), 2.04~2.14(4H, m), 2.29~2.42(8H, m), 2.80~2.88(1H, m), 3.04~3.08(2H, brd), 6.98(1H, d, J=2.2Hz), 7.07~7.21(2H, m), 7.36(1H, d, J=8.0Hz), 7.65(1H, d, J=8.0Hz), 7.94~8.06(1H, brs) IR(cm-1)(KBr) HCl salt 3502, 3279, 2948, 2663, 1618, 1458, 1428, 1338,1231, 1078, 1011, 971, 949, 753 | MS(EI) 339M+ Elemental Analysis Compositional Formula C22H33N3.2HCl.0.5H2O Calcd C 62.70; H 8.61; N 9.97; Cl 16.82 Found C 62.74; H 8.97; N 9.86; Cl 16.65 m.p. HCl salt 233° C. decomposition |
| EXAMPLE 13 | 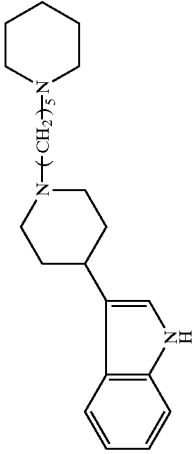 | H NMR(ppm)(300MHz, CDCl3) free form 1.24~1.66(14H, m), 1.75~1.89(2H, m), 2.03~2.13(4H, m), 2.26~2.40(6H, m), 2.83(1H, tt, J=3.6, 12.1Hz), 3.03~3.08(2H, brd), 6.98(1H, d, J=2.5Hz), 7.10(1H, dt, J=1.1, 7.1Hz), 7.18(1H, dt, J=1.1, 7.1Hz), 7.36(1H, dd, J=1.1, 7.1Hz), 7.66(1H, d, J=7.1Hz), 7.92~8.04(1H, brs) IR(cm-1)(KBr) free form 2936, 2811,1443, 1377, 1347, 1276, 1243, 1225, 1145, 1120, 1096, 1016, 975, 809, 783, 739 | MS(EI) 353M+ Elemental Analysis Compositional Formula C23H35N3.H2O Calcd C 74.35; H 10.04; N 11.31 Found C 74.04; H 10.13; N 11.13 m.p. free form 95° C. |
| EXAMPLE 14 | 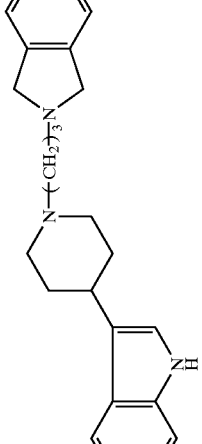 | H NMR(ppm)(300MHz, CDCl3) free form 1.81~1.91(4H, m), 2.06~2.18(4H, m), 2.49~2.54(2H, m), 2.76~2.87(3H, m), 3.09~3.12(2H, brd), 3.95(4H, s), 6.98(1H, d, J=2.2Hz), 7.08~7.20(6H, m), 7.35(1H, d, J=7.9Hz), 7.66(1H, d, J=7.9Hz), 8.00~8.09(1H, brs) IR(cm-1)(KBr) HCl salt 3269, 2936, 2399, 1636, 1458, 1340, 1232, 1100, 971, 744 | MS(EI) 359M+ Elemental Analysis Compositional Formula C24H29N3.2HCl.2H2O Calcd C 61.53; N 7.53; N 8.97 Found C 61.66; H 7.54; N 8.96 m.p. HCl salt 210° C. decomposition |

-continued

| EXAMPLE 15 | 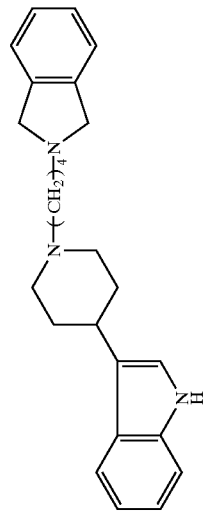 | H NMR(ppm)(300MHz, CDCl3) free form 1.65(4H, t, J=3.6Hz), 1.79~1.89(2H, m), 2.05~2.17(4H, m), 2.43~2.48(2H, m), 2.73~2.89(3H, m), 3.07~3.11(2H, brd), 3.94(4H, s), 6.97(1H, d, J=2.2Hz), 7.07~7.23(6H, m), 7.35(1H, d, J=8.0Hz), 7.65(1H, d, J=8.0Hz), 8.00~8.12(1H, brs) IR(cm−1)(KBr) HCl salt 3421, 2933, 2669, 1653, 1559, 1541, 1508, 1457,1103, 752 | MS(EI) 373M+ Elemental Analysis Compositional Formula C25H31N3.2HCl.0.9H2O Calcd C 64.90; H 7.58; N 9.08; Cl 15.33 Found C 64.93; H 7.49; N 9.03; Cl 15.33 m.p. °C. |
|---|---|---|---|
| EXAMPLE 16 | 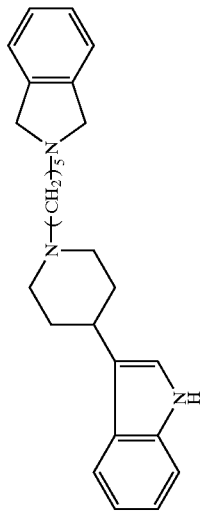 | H NMR(ppm)(300MHz, CDCl3) free form 1.38~1.48(2H, m), 1.56~1.69(4H, m), 1.76~1.90(2H, m), 2.08(4H, t, J=9.6Hz), 2.38~2.43(2H, m), 2.71~2.80(2H, m), 2.85(1H, tt, J=3.6, 11.6Hz), 3.06~3.10(2H, brd), 3.93(4H, s), 6.98(1H, d, J=1.9Hz), 7.08~7.24(6H, m), 7.34(1H, dd, J=0.8, 7.1Hz), 7.66(1H, dd, J=0.5, 8.5Hz), 7.90~8.04(1H, brs) IR(cm−1)(KBr)free form 3049, 2932, 2857, 2810, 1541, 1455, 1375, 1337, 1221, 1142, 1052, 868, 779, 739 | MS(EI) 387M+ Elemental Analysis Compositional Formula C26H33N3 Calcd C 80.58; H 8.58; N 10.84 Found C 80.36; H 8.49; N 10.71 m.p. free form 173° C. |
| EXAMPLE 17 | 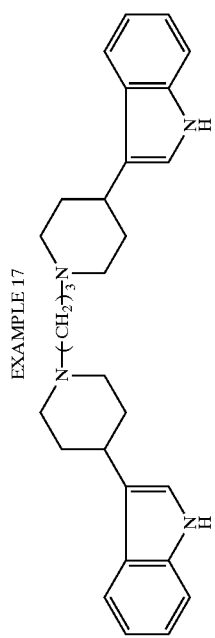 | H NMR(ppm)(300MHz, CDCl3) free form 1.81~1.90(6H, m), 2.06~2.18(8H, m), 2.42~2.47(4H, m), 2.85(2H, tt, J=3.6, 11.9Hz), 3.07~3.11(2H, brd), 6.98(2H, d, J=1.9Hz), 7.10(2H, dt, J=1.1, 8.0Hz), 7.18(2H, dt, J=1.1, 8.0Hz), 7.36(2H, dd, J=1.1, 8.0Hz), 7.66(2H, d, J=8.0Hz), 7.90~8.08(2H, brs) IR(cm−1)(KBr) HCl salt 3396, 2937, 2650, 1617, 1541,1457, 1425, 1339, 1246, 1102, 1010, 945, 808, 749 | MS(FAB) 441(M+H)+ Elemental Analysis Compositional Formula C29H36N4.2HCl.0.8H2O Calcd C 65.97; H 7.56; N 10.61; Cl 13.43 Found C 65.79; H 7.65; N 10.71; Cl 13.53 m.p. HCl salt 260° C. decomposition |
| EXAMPLE 18 | 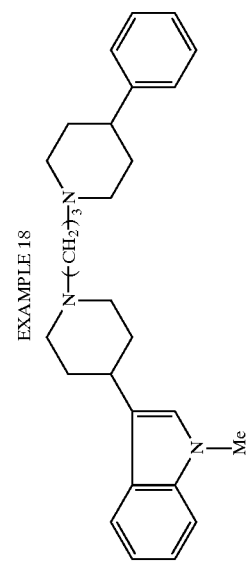 | H NMR(ppm)(300MHz, CDCl3) free form 1.75~1.88(8H, m), 2.01~2.16(6H, m), 2.40~2.53(5H, m), 2.83(1H, tt, J=3.6, 11.9Hz), 3.06~3.10(4H, brd), 3.73(3H, s), 7.08(1H, dt, J=1.1, 7.7Hz), 7.16~7.33(7H, m), 7.64(1H, d, J=7.7Hz) IR(cm−1)(KBr) HCl salt 3433, 2932, 2643, 1636, 1541, 1474, 1326, 1239, 1051, 946, 743, 701 | MS(FAB) 416(M+H)+ Elemental Analysis Compositional Formula C28H37N3.2HCl.H2O Calcd C 66.39; H 8.16; N 8.30; Cl 14.00 Found C 66.56; H 8.33; N 8.30; Cl 14.21 m.p. °C. |

-continued

| | | |
|---|---|---|
| EXAMPLE 19 | 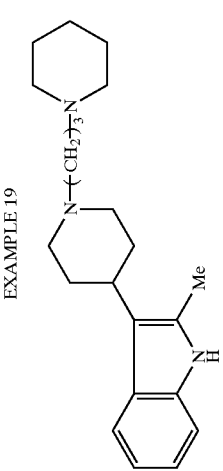 | H NMR(ppm)(300MHz, CDCl3) free form 1.44~1.48(2H, m), 1.56~1.64(4H, m), 1.74~1.83(4H, m), 2.01~2.09(2H, m), 2.17~2.43(11H, m), 2.74(1H, tt, J=3.8, 12.0Hz), 3.07~3.11(2H, brd), 7.00~7.11(2H, m), 7.24~7.27(2H, m), 7.71(1H, d, J=7.9Hz), 7.70~7.80(1H, brs)<br>IR(cm−1)(KBr) HCl salt<br>3421, 2946, 2668, 1653, 1559, 1541, 1508, 1458, 947, 753 | MS(EI) 339M+<br>Elemental Analysis<br>Compositional Formula<br>C22H33N3.2HCl.1.9H2O<br>Calcd C 59.16; H 8.76; N 9.41; Cl 15.87<br>Found C 59.24; H 8.65; N 9.36; Cl 15.91<br>m.p. °C. |
| EXAMPLE 20 | 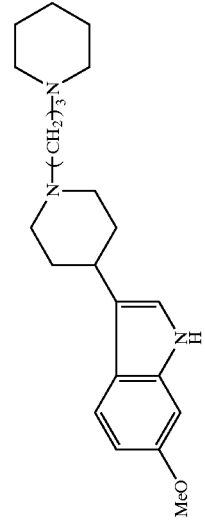 | H NMR(ppm)(300MHz, CDCl3) free form 1.43~1.47(2H, m), 1.55~1.63(4H, m), 1.70~1.86(4H, m), 2.02~2.18(4H, m), 2.31~2.42(8H, m), 2.78(1H, tt, J=3.8, 12.0Hz), 3.03~3.07(2H, brd), 3.84(3H, s), 6.77(1H, dd, J=2.2, 8.5Hz), 6.85~6.86(2H, m), 7.51(1H, d, J=8.5Hz), 7.82~7.94(1H, brs)<br>IR(cm−1)(KBr) HCl salt<br>3491, 3436, 3265, 2032, 2689, 2557, 1734, 1630, 1577, 1542, 1508, 1455, 1306, 1257, 1204, 1170, 1034 | MS(EI) 355M+<br>Elemental Analysis<br>Compositional Formula<br>C22H33N3O.2HCl.H2O<br>Calcd C 59.19; H 8.35; N 9.41; Cl 15.88<br>Found C 58.98; H 8.32; N 9.31; Cl 15.85<br>m.p. HCl salt 220° C. decomposition |
| EXAMPLE 21 | 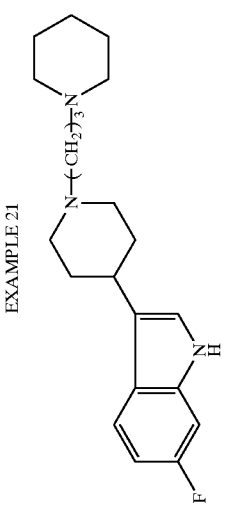 | H NMR(ppm)(300MHz, CDCl3) free form 1.44~1.45(2H, m), 1.56~1.63(4H, m), 1.74~1.86(4H, m), 2.02~2.14(4H, m), 2.31~2.42(6H, m), 2.76~2.83(1H, m), 3.04~3.08(2H, brd), 6.87(1H, ddd, J=2.2, 8.7, 9.6Hz), 6.95(1H, d, J=1.6Hz), 7.03(1H, dd, J=2.2, 9.9Hz), 7.54(1H, dd, J=5.5, 8.7Hz), 7.91~8.01(1H, brs)<br>IR(cm−1)(KBr) HCl salt<br>3493, 3279, 2942, 2640, 1625, 1457, 1348, 1228, 1135, 947, 846, 787 | MS(EI) 343M+<br>Elemental Analysis<br>Compositional Formula<br>C21H30FN3.2HCl.H2O<br>Calcd C 58.06; H 7.89; N 9.67<br>Found C 57.74; H 7.90; N 9.51<br>m.p. HCl salt 253° C. |
| EXAMPLE 22 | 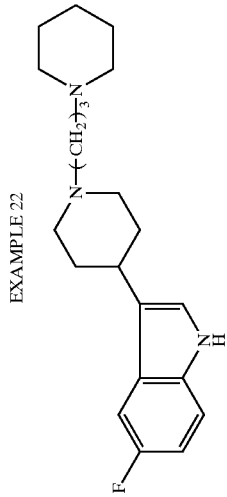 | H NMR(ppm)(300MHz, CDCl3) free form 1.44~1.45(2H, m), 1.56~1.63(4H, m), 1.71~1.85(4H, m), 2.01~2.18(4H, m), 2.31~2.42(8H, m), 2.70~2.80(1H, m), 3.04~3.08(2H, brd), 6.92(1H, dt, J=2.5, 9.0Hz), 7.01(1H, d, J=2.5Hz), 7.24~7.29(2H, m), 8.00~8.20(1H, brs)<br>IR(cm−1)(KBr) HCl salt<br>3489, 3217, 2939, 2639, 2551, 1637, 1485, 1457, 1228, 1168, 937, 795, 629 | MS(EI) 343M+<br>Elemental Analysis<br>Compositional Formula<br>C21H30FN3.2HCl.0.5H2O<br>Calcd C 59.29; H 7.82; N 9.88; Cl 16.67; F 4.47<br>Found C 59.25; H 7.77; N 9.80; Cl 16.67; F 4.16<br>m.p. HCl salt 240° C. decomposition |

-continued

| EXAMPLE 23 | 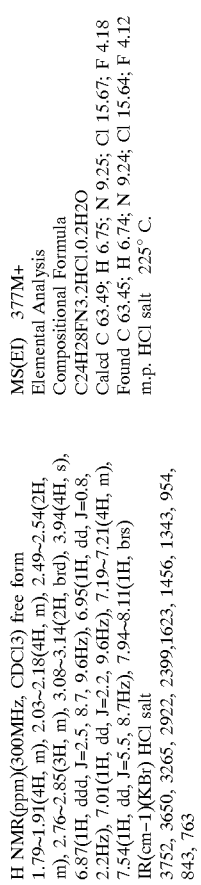 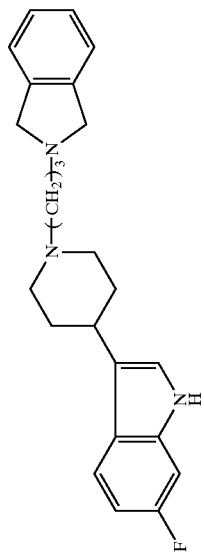 | H NMR(ppm)(300MHz, CDCl3) free form 1.79~1.91(4H, m), 2.03~2.18(4H, m), 2.49~2.54(2H, m), 2.76~2.85(3H, m), 3.08~3.14(2H, brd), 3.94(4H, s), 6.87(1H, ddd, J=2.5, 8.7, 9.6Hz), 6.95(1H, dd, J=0.8, 2.2Hz), 7.01(1H, dd, J=2.2, 9.6Hz), 7.19~7.21(4H, m), 7.54(1H, dd, J=5.5, 8.7Hz), 7.94~8.11(1H, brs) IR(cm−1)(KBr) HCl salt 3752, 3650, 3265, 2922, 2399,1623, 1456, 1343, 954, 843, 763 | MS(EI) 377M+ Elemental Analysis Compositional Formula C24H28FN3.2HCl.0.2H2O Calcd C 63.49; H 6.75; N 9.25; Cl 15.67; F 4.18 Found C 63.45; H 6.74; N 9.24; Cl 15.64; F 4.12 m.p. HCl salt 225° C. |
| EXAMPLE 24 | 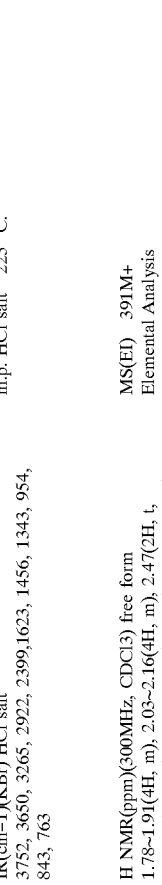 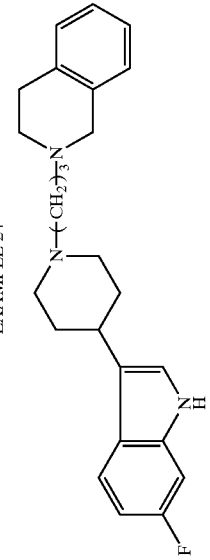 | H NMR(ppm)(300MHz, CDCl3) free form 1.78~1.91(4H, m), 2.03~2.16(4H, m), 2.47(2H, t, J=7.7Hz), 2.57(2H, t, J=7.7Hz), 2.75(2H, t, J=5.8Hz), 2.78~2.86(1H, m), 2.91(2H, t, J=5.2Hz), 3.06~3.10(2H, brd), 3.65(2H, s), 6.83~7.14(7H, m), 7.52~7.57(1H, m), 7.85~8.07(1H, brs) IR(cm−1)(KBr) HCl salt 3407, 2936, 2585, 1625, 1551, 1499, 1456, 1345,1225, 1139, 953, 809, 755 | MS(EI) 391M+ Elemental Analysis Compositional Formula C25H30FN3.2HCl.0.2H2O Calcd C 64.15; H 6.98; N 8.98; Cl 15.15; F 4.06 Found C 64.04; H 7.18; N 8.96; Cl 15.18; F 3.83 m.p. HCl salt 176° C. |
| EXAMPLE 25 | 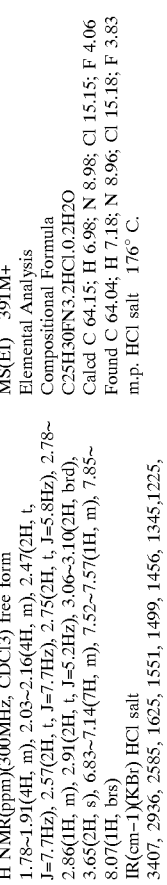 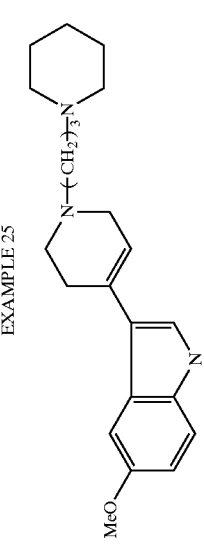 | H NMR(ppm)(300MHz, CDCl3) free form 1.44~1.46(2H, m), 1.56~1.64(4H, m), 1.76~1.86(2H, m), 2.35~2.40(6H, m), 2.50(12H, t, J=7.7Hz), 2.60~2.75(4H, m), 3.22(2H, dd, J=3.5, 5.7Hz), 3.86(3H, s), 6.12(1H, t, J=3.5Hz), 6.85~6.89(1H, m), 7.14(1H, d, J=2.6Hz), 7.24~7.27(1H, m), 7.33(1H, d, J=2.5Hz), 8.05~8.15(1H, brs) IR(cm−1)(KBr) HClsalt 3421, 3250, 2939, 2688, 1653, 1577, 1559, 1508, 1475, 1433, 1272, 1213, 1035, 939, 793, 641 | MS(EI) 353M+ Elemental Analysis Compositional Formula C22H31N3O.2HCl.1.2H2O Calcd C 58.98; H 7.96; N 9.38; Cl 15.83 Found C 59.11; H 7.82; N 9.29; Cl 15.81 m.p. HCl salt 158° C. |
| EXAMPLE 26 | 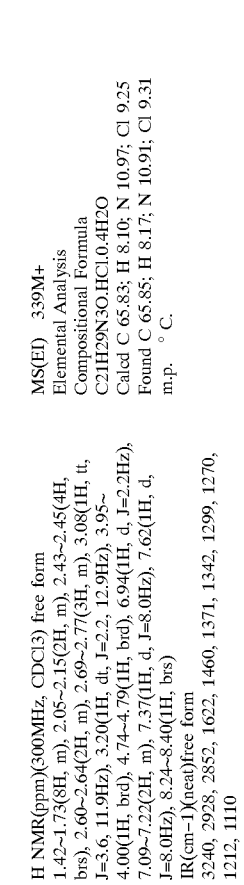 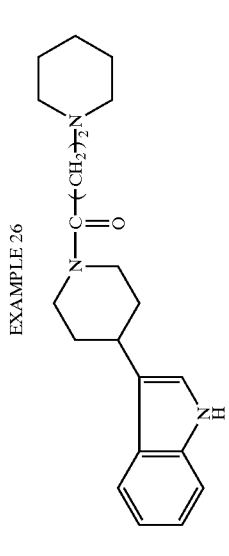 | H NMR(ppm)(300MHz, CDCl3) free form 1.42~1.73(8H, m), 2.05~2.15(2H, m), 2.43~2.45(4H, brs), 2.60~2.64(2H, m), 2.69~2.77(3H, m), 3.08(1H, tt, J=3,6, 11.9Hz), 3.20(1H, dt, J=2.2, 12.9Hz), 3.95~4.00(1H, brd), 4.74~4.79(1H, brd), 6.94(1H, d, J=2.2Hz), 7.09~7.22(2H, m), 7.37(1H, d, J=8.0Hz), 7.62(1H, d, J=8.0Hz), 8.24~8.40(1H, brs) IR(cm−1)(neat)free form 3240, 2928, 2852, 1622, 1460, 1371, 1342, 1299, 1270, 1212, 1110 | MS(EI) 339M+ Elemental Analysis Compositional Formula C21H29N3O.HCl.0.4H2O Calcd C 65.83; H 8.10; N 10.97; Cl 9.25 Found C 65.85; H 8.17; N 10.91; Cl 9.31 m.p. ° C. |

-continued

| | | |
|---|---|---|
| EXAMPLE 27 | 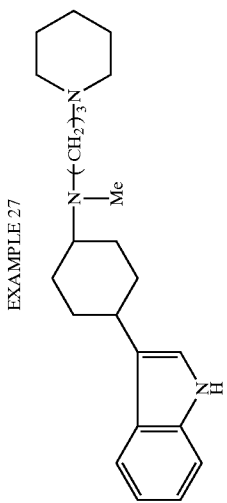 | H NMR(ppm)(300MHz, CDCl3) free form 1.43~1.83(12H, m), 1.93~2.54(16H, m), 2.73~2.79(0.5H, m), 3.16~3.27(0.5H, m), 6.91(0.5H, d, J=1.9Hz), 7.01(0.5H, d, J=1.6Hz), 7.05~7.19(2H, m), 7.33(1H, d, J=8.0Hz), 7.64(1H, d, J=7.7Hz), 8.35~8.50(1H, brs) IR(cm-1)(neat) free form 2934, 2860, 2804, 1456, 1377, 1352, 1218, 1154, 1112, 1040 | MS(EI) 353M+ Elemental Analysis Compositional Formula C23H35N3.2HCl.0.5H2O Calcd C 63.44; H 8.79; N 9.65; Cl 16.28 Found C 63.56; H 8.87; N 9.68; Cl 16.13 m.p. HCl salt 223° C. |
| EXAMPLE 28 | 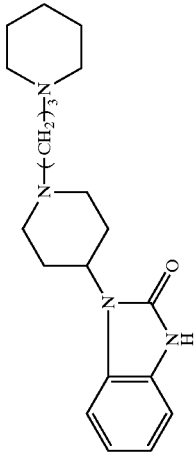 | H NMR(ppm)(300MHz, CDCl3) free form 1.44~1.46(2H, m), 1.57~1.64(4H, m), 1.70~1.84(4H, m), 2.10~2.17(2H, m), 2.34~2.54(10H, m), 3.08~3.12(2H, brd), 4.39(1H, tt, J=4.1, 12.6Hz), 6.99~7.14(3H, m), 7.25~7.31(1H, m), 10.70~10.83(1H, brs) IR(cm-1)(neat) free form 3148, 2938, 2812, 2774, 1694, 1487, 1377, 1274, 1259, 1216, 1156, 1094 | MS(EI) 342M+ Elemental Analysis Compositional Formula C20H30N4O.2HCl.0.4H2O Calcd C 56.84; H 7.82; N 13.26; Cl 16.78 Found C 56.79; H 7.79; N 13.02; Cl 16.73 m.p. HCl salt 224° C. decomposition |
| EXAMPLE 29 | 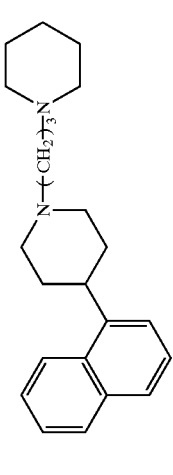 | H NMR(ppm)(300MHz, CDCl3) free form 1.44~1.46(2H, m), 1.57~1.64(4H, m), 1.75~1.83(2H, m), 1.94~1.99(4H, m), 2.20(2H, dt, J=3.0, 11.5Hz), 2.33~2.47(8H, m), 3.12~3.16(2H, brd), 3.28~3.38(1H, m), 7.41~7.54(4H, m), 7.71(1H, dd, J=6.8, 9.3Hz), 7.85~7.88(1H, m), 8.10(1H, d, J=8.2Hz) IR(cm-1)(KBr) HCl salt 3458, 2941, 2546, 1597, 1510, 1434, 1197, 1157,1091, 987, 964, 796, 776 | MS(EI) 366M+ Elemental Analysis Compositional Formula C23H32N2.2HCl Calcd C 67.47; H 8.37; N 6.84; Cl 17.32 Found C 67.24; H 8.27; N 6.86; Cl 17.32 m.p. HCl salt 279° C. |
| EXAMPLE 30 | 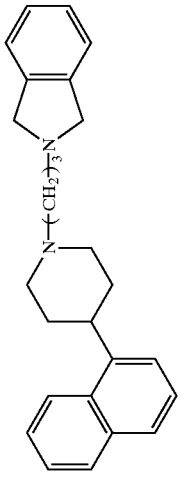 | H NMR(ppm)(300MHz, CDCl3) free form 1.78~2.02(6H, m), 2.24(2H, dt, J=3.3, 11.3Hz), 2.53~2.59(2H, m), 2.78~2.83(2H, m), 3.17~3.21(2H, brd), 3.30~3.40(1H, m), 3.95(4H, brs), 7.42~7.55(4H, m), 7.69~7.75(1H, m), 7.85~7.88(1H, m), 8.11(1H, d, J=8.2Hz) IR(cm-1)(KBr) HCl salt 3449, 3044, 2928, 2510, 1596, 1509, 1438, 953, 798, 775, 747 | MS(EI) 370M+ Elemental Analysis Compositional Formula C26H30N2.2HCl.0.5H2O Calcd C 69.02; H 7.35; N 6.19; Cl 15.67 Found C 69.12; H 7.39; N 6.24; Cl 15.61 m.p. HCl salt 240° C. |

-continued

| EXAMPLE | | H NMR(ppm)(300MHz, CDCl3) free form | |
|---|---|---|---|
| EXAMPLE 31 | 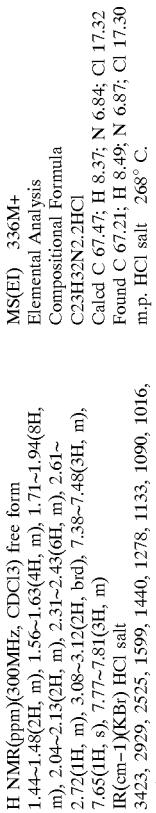 | 1.44~1.48(2H, m), 1.56~1.63(4H, m), 1.71~1.94(8H, m), 2.04~2.13(2H, m), 2.31~2.43(6H, m), 2.61~2.72(1H, m), 3.08~3.12(2H, brd), 7.38~7.48(3H, m), 7.65(1H, s), 7.77~7.81(3H, m)<br>IR(cm-1)(KBr) HCl salt<br>3423, 2929, 2525, 1599, 1440, 1278, 1133, 1090, 1016, 945, 912, 861, 823, 760 | MS(EI) 336M+<br>Elemental Analysis<br>Compositional Formula<br>C23H32N2.2HCl<br>Calcd C 67.47; H 8.37; N 6.84; Cl 17.32<br>Found C 67.21; H 8.49; N 6.87; Cl 17.30<br>m.p. HCl salt 268° C. |
| EXAMPLE 32 | 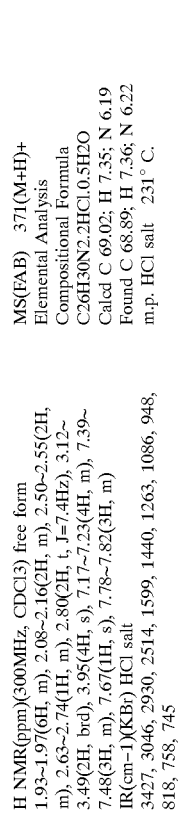 | 1.93~1.97(6H, m), 2.08~2.16(2H, m), 2.50~2.55(2H, m), 2.63~2.74(1H, m), 2.80(2H, t, J=7.4Hz), 3.12~3.49(2H, brd), 3.95(4H, s), 7.17~7.23(4H, m), 7.39~7.48(3H, m), 7.67(1H, s), 7.78~7.82(3H, m)<br>IR(cm-1)(KBr) HCl salt<br>3427, 3046, 2930, 2770, 2514, 1599, 1440, 1263, 1086, 948, 818, 758, 745 | MS(FAB) 371(M+H)+<br>Elemental Analysis<br>Compositional Formula<br>C26H30N2.2HCl.0.5H2O<br>Calcd C 69.02; H 7.35; N 6.19<br>Found C 68.89; H 7.36; N 6.22<br>m.p. HCl salt 231° C. |
| EXAMPLE 33 | 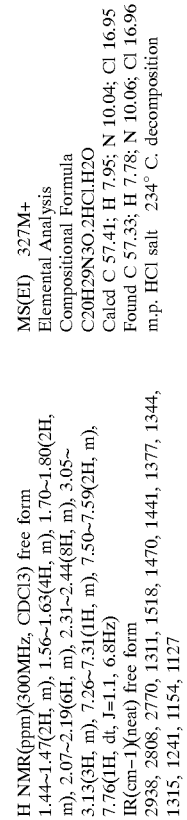 | 1.44~1.47(2H, m), 1.56~1.63(4H, m), 1.70~1.80(2H, m), 2.07~2.19(6H, m), 2.31~2.44(8H, m), 3.05~3.13(3H, m), 7.26~7.31(1H, m), 7.50~7.59(2H, m), 7.76(1H, dt, J=1.1, 6.8Hz)<br>IR(cm-1)(neat) free form<br>2938, 2808, 2770, 1311, 1518, 1470, 1441, 1377, 1344, 1315, 1241, 1154, 1127 | MS(EI) 327M+<br>Elemental Analysis<br>Compositional Formula<br>C20H29N3O.2HCl.H2O<br>Calcd C 57.41; H 7.95; N 10.04; Cl 16.95<br>Found C 57.33; H 7.78; N 10.06; Cl 16.96<br>m.p. HCl salt 234° C. decomposition |
| EXAMPLE 34 | 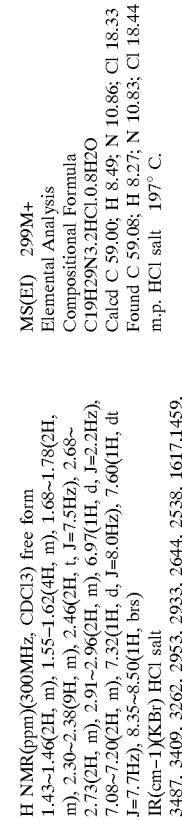 | 1.43~1.46(2H, m), 1.55~1.62(4H, m), 1.68~1.78(2H, m), 2.30~2.38(9H, m), 2.46(2H, t, J=7.5Hz), 2.68~2.73(2H, m), 2.91~2.96(2H, m), 6.97(1H, d, J=2.2Hz), 7.08~7.20(2H, m), 7.32(1H, d, J=8.0Hz), 7.60(1H, d, J=7.7Hz), 8.35~8.50(1H, brs)<br>IR(cm-1)(KBr) HCl salt<br>3487, 3409, 3262, 2953, 2933, 2644, 2538, 1617, 1459, 1427, 1338, 1231, 1096, 1009, 946, 854, 750 | MS(EI) 299M+<br>Elemental Analysis<br>Compositional Formula<br>C19H29N3.2HCl.0.8H2O<br>Calcd C 59.00; H 8.49; N 10.86; Cl 18.33<br>Found C 59.08; H 8.27; N 10.83; Cl 18.44<br>m.p. HCl salt 197° C. |
| EXAMPLE 35 | 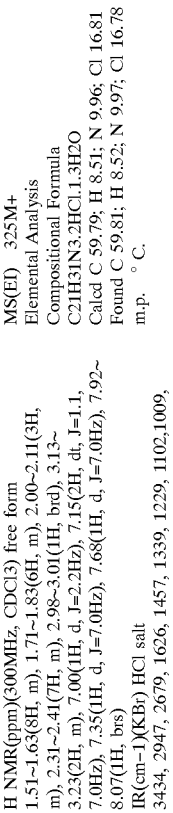 | 1.51~1.63(8H, m), 1.71~1.83(6H, m), 2.00~2.11(3H, m), 2.31~2.41(7H, m), 2.98~3.01(1H, brd), 3.13~3.23(2H, m), 7.00(1H, d, J=2.2Hz), 7.15(2H, dt, J=1.1, 7.0Hz), 7.35(1H, d, J=7.0Hz), 7.68(1H, d, J=7.0Hz), 7.92~8.07(1H, brs)<br>IR(cm-1)(KBr) HCl salt<br>3434, 2947, 2679, 1626, 1457, 1339, 1229, 1102, 1009, 945, 752 | MS(EI) 325M+<br>Elemental Analysis<br>Compositional Formula<br>C21H31N3.2HCl.1.3H2O<br>Calcd C 59.79; H 8.51; N 9.96; Cl 16.81<br>Found C 59.81; H 8.52; N 9.97; Cl 16.78<br>m.p. ° C. |

-continued

| | | |
|---|---|---|
| EXAMPLE 36 | 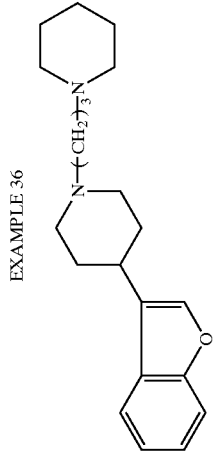 | H NMR(ppm)(300MHz, CDCl3) free form 1.44~1.47(2H, m), 1.60~1.63(4H, m), 1.70~1.88(4H, m), 2.03~2.14(4H, m), 2.31~2.42(8H, m), 2.73(1H, tt, J=3.6, 11.9Hz), 3.04~3.08(2H, brd), 7.20(3H, dt, J=1.1, 7.3Hz), 7.38(1H, s), 7.46(1H, d, J=7.3Hz), 7.61(1H, d, J=7.3Hz) IR(cm-1)(KBr) HCl salt 3463, 2951, 2543, 1455, 1251, 1185, 1102, 1016,987, 956, 857, 741 | MS(EI) 326M+ Elemental Analysis Compositional Formula C21H30N2O.2HCl.0.2H2O Calcd C 62.59; H 8.10; N 6.95; Cl 17.59 Found C 62.61; H 7.94; N 7.01; Cl 17.65 m.p. HCl salt 267° C. |
| EXAMPLE 37 | 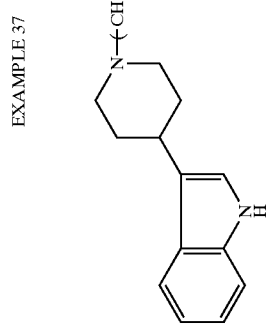 | H NMR(ppm)(300MHz, CDCl3) free form 1.36~1.88(10H, m), 2.03~2.13(4H, m), 2.34~2.39(2H, m), 2.83(1H, tt, J=3.3, 11.2Hz), 3.03~3.07(2H, brd), 3.69(2H, t, J=7.3Hz), 6.98(1H, d, J=2.5Hz), 7.07~7.21(2H, m), 7.35(2H, dd, J=0.8, 8.0Hz), 7.64~7.74(3H, m), 7.82~7.83(2H, m), 7.91~8.03(1H, brs) IR(cm-1)(KBr) HCl salt 3238, 2938, 2474, 1770, 1713, 1437,1397, 1368, 1064, 745, 718 | MS(EI) 429M+ Elemental Analysis Compositional Formula C27H31N3O2.HCl Calcd C 69.59; H 6.92; N 9.02; Cl 7.61 Found C 69.45; H 6.97; N 8.95; Cl 7.50 m.p. HCl salt 203° C. |
| EXAMPLE 38 | 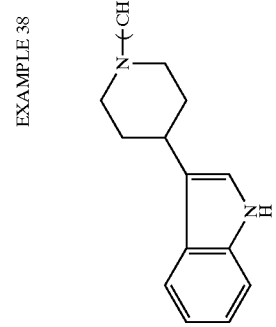 | H NMR(ppm)(300MHz, CDCl3) free form 1.74(2H, dq, J=3.6, 11.8Hz), 2.01~2.06(2H, brd), 2.24(2H, dt, J=2.2, 11.8Hz), 2.70(2H, t, J=6.9Hz), 2.82(1H, tt, J=3.6, 11.8Hz), 3.11~3.15(2H, brd), 3.89(2H, t, J=6.9Hz), 6.94(1H, d, J=2.5Hz), 7.06~7.20(2H, m), 7.35(1H, dd, J=0.5, 8.0Hz), 7.62(1H, dd, J=0.5, 8.0Hz), 7.68~7.74(2H, m), 7.82~7.88(2H, m), 7.91~8.06(1H,brs) IR(cm-1)(KBr) HCl salt 3216, 2950, 2451, 1773, 1719, 1459, 1395, 1053, 749, 708 | MS(EI) 373M+ Elemental Analysis Compositional Formula C23H23N3O2.HCl Calcd C 67.39; H 5.90; N 10.25; Cl 8.65 Found C 67.13; H 5.89; N 10.16; Cl 8.46 m.p. HCl salt 195° C. |
| EXAMPLE 39 | 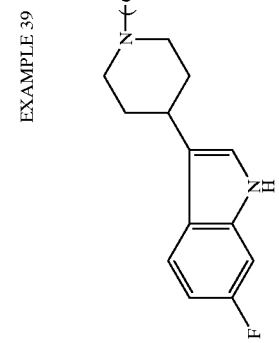 | H NMR(ppm)(300MHz, CDCl3) free form 1.59~1.84(6H, m), 2.00~2.13(4H, m), 2.42(2H, t, J=7.5Hz), 2.74~2.82(1H, m), 3.01~3.05(2H, brd), 3.73(2H, t, J=7.1Hz), 6.83~7.05(3H, m), 7.51~7.56(1H, m), 7.69~7.74(2H, m), 7.82~7.86(2H, m), 7.94~8.02(1H, brs) IR(cm-1)(KBr) HCl salt 3253, 2938, 2637, 1770, 1709, 1457, 1400, 1099, 1061, 949, 798, 721 | MS(EI) 419M+ Elemental Analysis Compositional Formula C25H26FN3O2.HCl.0.1H2O Calcd C 65.60; H 5.99; N 9.18; Cl 7.74; F 4.15 Found C 65.51; H 5.89; N 9.18; Cl 7.83; F 3.97 m.p. HCl salt 255° C. |

-continued

| EXAMPLE | | |
|---|---|---|
| EXAMPLE 40 | 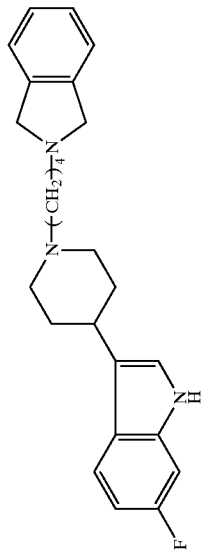 | H NMR(ppm)(300MHz, CDCl3) free form 1.64(2H, t, J=3.6Hz), 1.73~1.87(4H, m), 2.06~2.16(4H, m), 2.45(2H, t, J=7.1Hz), 2.73~2.84(3H, m), 3.06~3.10(2H, brd), 3.94(4H, s), 6.82~6.89(1H, m), 6.92(1H, d, J=2.2Hz), 6.99(1H, dd, J=2.2, 9.6Hz), 7.20(4H, brs), 7.54(1H, dd, J=5.5, 8.7Hz), 8.09~8.24(1H, brs) IR(cm-1)(KBr) HCl salt 3388, 2938, 2542, 1624, 1550, 1457,1343, 1223, 1140, 1098, 952, 805, 754, 611 | MS(EI) 391M+ Elemental Analysis Compositional Formula C25H30FN3.HCl.1.6H2O Calcd C 60.87; H 7.19; N 8.52 Found C 60.88; H 7.34; N 8.71 m.p. °C. |
| EXAMPLE 41 | 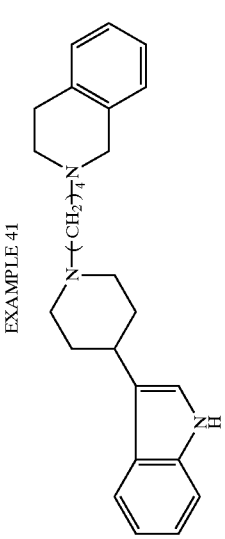 | H NMR(ppm)(300MHz, CDCl3) free form 1.63~2.16(10H, m), 2.54(2H, t, J=7.7Hz), 2.43(2H, t, J=7.7Hz), 2.74(2H, t, J=5.9Hz), 2.84(1H, tt, J=3.6, 11.9Hz), 2.91(2H, t, J=5.9Hz), 3.05~3.00(2H, brd), 3.64(2H, s), 6.94~7.20(7H, m), 7.34(1H, d, J=7.9Hz), 7.65(1H, d, J=7.9Hz), 7.98~8.19(1H, brs) IR(cm-1)(KBr) HCl salt 3397, 2938, 2702, 1618, 1457, 1340, 1228, 1057,968, 914, 752 | MS(EI) 401M+ Elemental Analysis Compositional Formula C26H33N3.2HCl.1.2H2O Calcd C 64.78; H 7.82; N 8.72; Cl 14.71 Found C 64.70; H 7.74; N 8.72; Cl 14.55 m.p. °C. |
| EXAMPLE 42 | 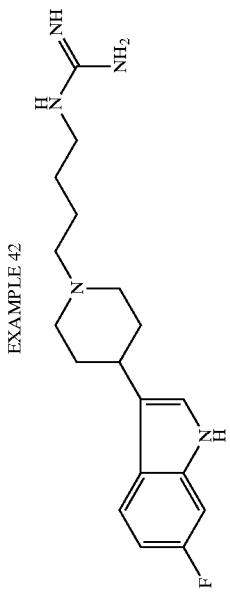 | N NMR(ppm)(300MHz, CD3OD) free form 1.48~1.49(4H, m), 1.61~1.75(2H, m), 1.88~1.92(2H, brd), 2.01~2.09(2H, m), 2.29~2.33(2H, m), 2.65~2.73(1H, m), 2.90~2.96(2H, brd), 3.01~3.10(2H, m), 6.63(1H, ddd, J=2.2, 8.5, 9.6Hz), 6.86~6.90(2H, m), 7.39(1H, dd, J=5.5, 8.5Hz) IR(cm-1)(neat) free form 3330, 2935, 2855, 2822, 2460, 2239, 2068, 1628, 1458, 1378,1344, 1222, 1118, 977, 801 | MS(EI) 331M+ Elemental Analysis Compositional Formula Calcd Found m.p. °C. |
| EXAMPLE 43 | 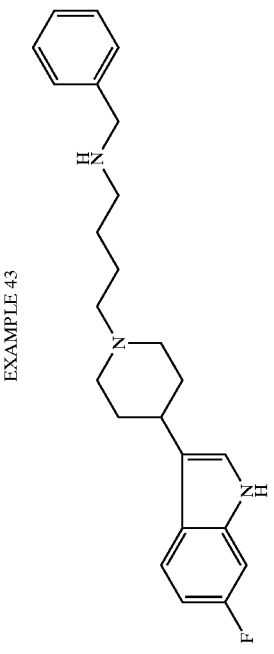 | H NMR(ppm)(300MHz, CDCl3) free form 1.54~2.13(10H, m), 2.39(2H, t, J=6.9Hz), 2.67(2H, t, J=6.9Hz), 2.78(1H, tt, J=3.6, 11.8Hz), 3.02~3.06(2H, brd), 3.80(2H, s), 6.82~6.89(1H, d, J=1.6Hz), 7.01(1H, dd, J=1.9, 9.6Hz), 7.23~7.34(5H, m), 7.52(1H, dd, J=5.2, 8.8Hz), 8.23~8.38(1H, brs) IR(cm-1)(neat) free form 2932, 2813, 1627, 1496, 1458, 1343, 1217,1143, 1100, 800, 752 | MS(EI) 379M+ Elemental Analysis Compositional Formula Calcd Found m.p. °C. |

Example 44

Experiment on Binding to α1A and α1B Adrenoceptors (1) Preparation of Receptor Preparation All experiments were performed at temperatures between 0° C. and 4° C. As an α1A adrenoceptor preparation, a 43,000×g precipitation fraction was prepared from a rat submaxillary gland, and this was used as a crude membrane preparation in the experiment.

A Sprague-Dawley male rat was exsanguinated under ether anesthesia, and the submaxillary gland was isolated, was weighed and was cut to pieces with scissors. The cut gland was put into a Potter-Elvehjem type Teflon homogenizer, and was homogenized with 5 times by volume (5 mL per 1 g of the wet weight of the submaxillary gland) of a 50 mM Tris-HCl buffer (pH=7.4) containing 5 mM EDTA, 0.2 mM DTT, and 0.1 mM PMSF. The resulting homogenate was allowed to pass through a nylon mesh and was centrifuged at 800×g for 10 minutes, and the resulting supernatant was centrifuged at 43,000×g for 15 minutes. The precipitate was suspended in a 50 mM Tris-HCl buffer (pH=7.4) (Buffer A) containing 10 mM MgCl2, 0.2 mM DTT, and 0.1 mM PMSF and was then centrifuged at 43,000×g for 15 minutes. The resulting precipitate was suspended in Buffer A to a protein concentration of about 10 mg/mL, and the suspension was used as the crude membrane preparation.

As an α1B adrenoceptor preparation, a 100,000×g precipitation fraction was prepared from a rat liver and this was used as a crude membrane preparation in the experiment.

A Sprague-Dawley male rat was exsanguinated under ether anesthesia, and the liver was isolated, was weighed and was cut into pieces with scissors. The cut liver was put into a Potter-Elvehjem type Teflon homogenizer, and was homogenized with 9 times by volume (9 mL per 1 g of the wet weight of the liver) of a 50 mM Tris-HCl buffer (pH 7.4) containing 0.25 M sucrose, 10 mM MgCl2, 1 mM EDTA, 0.2 mM DTT, and 0.1 mM PMSF. The homogenate was centrifuged at 800×g for 10 minutes, and the resulting supernatant was centrifuged at 100,000×g for 10 minutes, and the supernatant was then further centrifuged at 100,000×g for 60 minutes. The precipitate obtained by centrifugation was suspended in a 50 mM Tris-HCl buffer (pH=7.4) (Buffer A) containing 10 mM MgCl2, 0.2 mM DTT, and 0.1 mM PMSF to a protein concentration of about 10 mg/mL, and the suspension was used as the crude membrane preparation.

Each of the crude membrane preparations was dispensed and was stored at −80° C. and was subjected to the experiment on use. The protein concentration was determined by Lowry method using bovine serum albumin as a standard.

(2) Receptor Binding Experiment

Buffer A (400 μL) containing 0.5 nM [3H] prazosin and 200 μg crude membrane preparation was used as a standard reaction solution. The receptor preparation and [3H] prazosin were incubated at 25° C. for 30 minutes, and 2 mL of cold Buffer A was added to terminate the reaction. The cell membrane was separated by suction filtration under rapidly reduced pressure with a Whatman GF/C glass filter, and a binding activity (total binding activity, total avidity) was determined from the radioactivity bound to the cell membrane. The same experimental procedure was performed in the presence of 10 μM phentolamine to thereby determine a nonspecific binding activity. A specific binding activity was calculated by subtracting the nonspecific binding activity from the total binding activity.

A solution of a test drug was prepared by dissolving the test drug to 10 mM in distilled water, ethanol, or DMSO, and serially diluting the solution with distilled water.

Kd values and Bmax values were determined using Scatchard plots. Dissociation constant Ki (riM) of each compound was determined according to the following equation.

$$Ki = IC50/[1 + (\text{radioactive ligand concentration}/Kd)]$$

The results are shown in the following tables.

| Compound Example No. | α1B Ki (nM) |
| --- | --- |
| 1 | 7.1 |
| 2 | 6.7 |
| 3 | 3.0 |
| 4 | 4.8 |
| 5 | 2.1 |
| 6 | 7.5 |
| 7 | 7.2 |
| 12 | 1.1 |
| 13 | 1.5 |
| 14 | 3.6 |
| 15 | 1.4 |
| 16 | 1.6 |
| 18 | 60 |
| 19 | 71 |
| 21 | 0.63 |
| 22 | 16 |
| 23 | 0.79 |
| 24 | 0.61 |
| 25 | 61 |
| 26 | 200 |
| 27 | 89 |
| 29 | 69 |
| 31 | 92 |
| 34 | 91 |
| 35 | 110 |
| 36 | 7.7 |
| Reference Example 21 | 860 |

| Compound Example No. | α1A Ki (nM) |
| --- | --- |
| 1 | 230 |
| 2 | 100 |
| 3 | 120 |
| 4 | 240 |
| 5 | 130 |
| 6 | 51 |
| 7 | 53 |
| 12 | 56 |
| 13 | 57 |
| 14 | 50 |
| 15 | 30 |
| 16 | 82 |
| 18 | 480 |
| 19 | 1900 |
| 21 | 21 |
| 22 | 690 |
| 23 | 18 |
| 24 | 24 |
| 25 | 3200 |
| 26 | 4100 |
| 27 | 2000 |
| 29 | 890 |
| 31 | 2200 |
| 34 | 2200 |
| 35 | 1500 |
| 36 | 60 |
| ReferenceExample21 | 870 |

The results show that the invented compounds have high affinity for α1B adrenoceptor. Additionally, these compounds are found to be α1B adrenoceptor antagonists as they have no constriction activity on various blood vessels. The invented compounds are useful in elucidation of physiological activities mediated by the α1B adrenoceptor and in prophylaxis/therapy of diseases in which the α1B adrenoceptor is involved.

Example 45

Inhibitory activity against vasopressor response induced by α1 adrenoceptor agonist:

The inhibitory activity of the α1B adrenoceptor antagonist according to Example 23 against vasopressor response induced by phenylephrine (an α1 adrenoceptor agonist) in rats under anesthesia was studied. Specifically, the compound was intravenously continuously administered to Sprague-Dawley male rats (weight: 320 to 440 g) under pentobarbital (75 mg/kg, i.p.) anesthesia, and vasopressor responses of phenylephrine were determined and the inhibition rate was determined before administration and 15 minutes after administration. The compound was dissolved in physiological saline, and was infused into the femoral vein at a rate of 20 μl/kg/min. Phenylephrine was dissolved in physiological saline and was bolus injected at a dose of 0.2 ml/kg (3 μg/kg). The inhibition rate was calculated according to the following equation.

Inhibition rate (7)=[1—(pressure increase induced by phenylephrine 15 minutes after administration of the example compound)/(pressure increase induced by phenylephrine before administration of the example compound)]×100

The results are shown in the following table.

Inhibitory activity of the compound against vasopressor response due to phenylephrine

| Dose of compound (mg/kg/min) | 0.1 | 0.3 | 1 | 3 |
| --- | --- | --- | --- | --- |
| Number of rats used | 4 | 3 | 3 | 3 |
| Inhibition rate (%) | 24 ± 5 | 47 ± 5 | 72 ± 5 | 86 ± 2 |

The numerical values show mean±standard error.

The results show that the invented compounds inhibit pressure increase induced by ccl adrenoceptor agonists.

Accordingly, the invented compounds are useful in elucidation of physiological activities mediated by the α1B adrenoceptor and in prophylaxis/therapy of diseases in which the α1B adrenoceptor is involved, and are useful, for example, as therapeutic agents for hypertension.

Industrial Applicability

The invented compounds are antagonists having high affinity for α1B adrenoceptor and are useful as pharmacological tools for elucidation of physiological activities mediated by the α1B adrenoceptor, or, as pharmaceutical agents for use in prophylaxis/therapy of diseases (e.g., hypertension) in which the α1B adrenoceptor is involved.

What is claimed is:

1. A method of treating diseases selected from the group consisting of ocular tension, carcinoma, sarcoma and tumentia comprising administering to a patient a therapeutically effective amount of an α1B adrenoceptor antagonist compound represented by the formula (I) or a pharmacologically acceptable acid addition salt thereof:

(I)

(wherein Ar is indolyl, naphthalenyl, quinolinyl, benzimidazolyl, benzofuranyl, benzothiophenyl, benzisoxazolyl, or 2-ketobenzimidazolinyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 1 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$R^1$ is hydrogen, alkyl having 1 to 6 carbon atoms, aryl having 6 to 12 carbon atoms, alkenyl having 2 to 9 carbon atoms, or cycloalkyl having 3 to 8 carbon atoms;

B—N—$R^1$ forms a ring structure and is piperidine or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

n denotes an integer of 0 or 1;

A is alkylene having 2 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:

2) —$NR^2R^3$, wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbons atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR$^2$R$^3$ together forms piperidine, pyrrolidine, 1,3,4-trihydroisoquinoline, isoindoline, piperazine, morpholine, 2-piperidone, 2-pyrrolidone, indoline, 2,3,4-trihydroquionoline, 2,3,4-trihydroquinoxaline, dihydrobenzoxazine, benzothiane, phthalamide, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

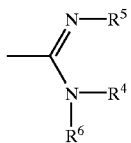

(II)

(wherein each of R$^4$, R$^5$, R$^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or R$^4$ and R$^5$ together form an imidazoline ring)).

2. A method for treating circulatory disease comprising administering to a patient a therapeutically effective amount of an aiB adrenoceptor compound represented by the formula (I) or a pharmacologically acceptable acid addition salt thereof:

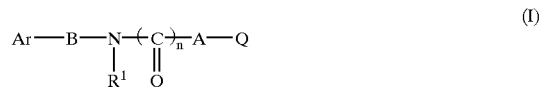

(I)

(wherein Ar is idolyl, naphthalenyl, quinolinyl, benzimidazolyl, benzofuranyl, benzothiophenyl, benzisoxazolyl, or 2-ketobenzimidazolinyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 1 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

R$^1$ is hydrogen, alkyl having 1 to 6 carbon atoms, aryl having 6 to 12 carbon atoms, alkenyl having 2 to 9 carbon atoms, or cycloalkyl having 3 to 8 carbon atoms;

B—N—R$^1$ forms a ring structure and is piperidine or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

n denotes an integer of 0 or 1;

A is alkylene having 2 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —NR$^2$R$^3$,
  wherein each of R$^2$ and R$^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbons atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR$^2$R$^3$ together forms piperidine, pyrrolidine, 1,3,4-trihydroisoquinoline, isoindoline, piperazine, morpholine, 2-piperidone, 2-pyrrolidone, indoline, 2,3,4-trihydroquionoline, 2,3,4-trihydroquinoxaline, dihydrobenzoxazine, benzothiane, phthalamide, or guanidine, each of which is unsubstituted or substituted with the groups selected from the group consisting of halogen, nitro group, acylamino group having 1 to 9 carbon atoms, amino group, alkylamino group having, 1 to 8 carbon atoms, arylamino group having 6 to 15 carbon atoms, dialkylamino group having 2 to 16 carbon atoms, diatylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

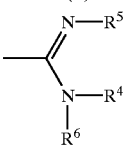

(II)

(wherein each of R$^4$, R$^5$, R$^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or R$^4$ and R$^5$ together form an imidazoline ring)).

3. A method for treating hypertension comprising administering to a patient a therapeutically effective amount of an α1 B adrenoceptor compound represented by the formula (I) or a pharmacologically acceptable acid addition salt thereof:

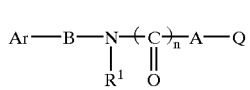

(I)

(wherein Ar is indolyl, naphthalenyl, quinolinyl, benzimidazolyl, benzofuranyl, benzothiophenyl, benzisoxazolyl, or 2-ketobenzimidazolinyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 1 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;
  R$^1$ is hydrogen, alkyl having 1 to 6 carbon atoms, aryl having 6 to 12 carbon atoms, alkenyl having 2 to 9 carbon atoms, or cycloalkyl having 3 to 8 carbon atoms;

B—N—R¹ forms a ring structure and is piperidine or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

n denotes an integer of 0 or 1;

A is alkylene having 2 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —NR²R³,
wherein each of R² and R³ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylarnino group having 12 to 20 carbons atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR²R³ together forms piperidine, pyrrolidine, 1,3,4-trihydroisoquinoline, isoindoline, piperazine, morpholine, 2-piperidone, 2-pyrrolidone, indoline, 2,3,4-trihydroquionoline, 2,3,4-trihydroquinoxaline, dihydrobenzoxazine, benzothiane, phthalamide, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

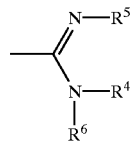

(II)

(wherein each of $R^4$, $R^5$, $R^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or $R^4$ and $R^5$ together form an imidazoline ring)).

4. The method according to claim 1, 2 or 3, wherein in the formula (I), n is 0;

Ar is indolyl, naphthalenyl, quinolinyl, benzimidazolyl, benzofuranyl, or benzothiophenyl, each of which is unsubstituted or substituted with the groups selected from the group consisting of halogen, nitro group, acylamino group having 1 to 9 carbon atoms, anino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B—N—R$^1$ forms a ring structure and is piperidine or 2,3,6-trihydropyridine, each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

A has the same meaning as defined in claim 1;

Q is:
1) —NR$^2$R$^3$,
wherein each of R$^2$ and R$^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR$^2$R$^3$ together forms piperidine, pyrrolidine, 1,3,4-trihydroisoquinoline, isoindoline, piperazine, morpholine, indoline, 2,3,4-trihydroquinotine, 2,3,4-trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylarnino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

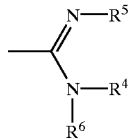

(II)

(wherein R$^4$, R$^5$, and R$^6$ have the same meanings as defined in claim 1).

5. The method according to claims 1, 2 or 3, wherein, in the formula (I), n is 0;

Ar is indolyl, naphthalenyl, quinolinyl, or benzimidazolyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylanrino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B—N—R$^1$ forms a ring structure and is piperidine which is unsubstituted or substituted with the groups selected from the group consisting of halogen, hydroxyl, alkyl group having 1 to 8 carbon atoms, aryl group having 6 to 15 carbon atoms, haloalkyl group having 1 to 8 carbon atoms, amninosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

A is alkylene having 2 to 8 carbon atoms or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cuano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —NR²R³ (wherein each of R² and R³ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR²R³ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, arytoxy group having 6 to 15 carbon atoms, haloalkyl group having 1 to 8 carbon atoms, haloalkoxy group having Ito 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

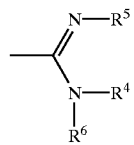

(II)

(wherein R⁴, R⁵, and R⁶ have the same meanings as defined in claim 1).

6. The method according to any one of claims 1, 2 or 3, wherein, in the formula (I), n is 0;

Ar is indolyl or naphthalenyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

B—N—R¹ forms a ring structure and is represented by formula 1) which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

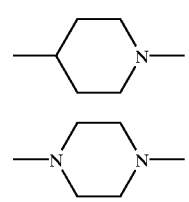

1)

2)

A is alkylene having 3 to 8 carbons atoms, which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

Q is:
1) —NR²R³ (wherein each of R² and R³ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or —NR²R³ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

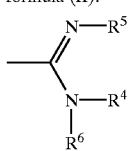
(II)

(wherein $R^4$, $R^5$, and $R^6$ have the same meanings as defined in claim 1).

7. A compound represented by the formula (III), or a pharmacologically accetable acid addition salt thereof:

Ar²—A—A—Q² (III)

(wherein D represents one of the following formulae 1) to 5), each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

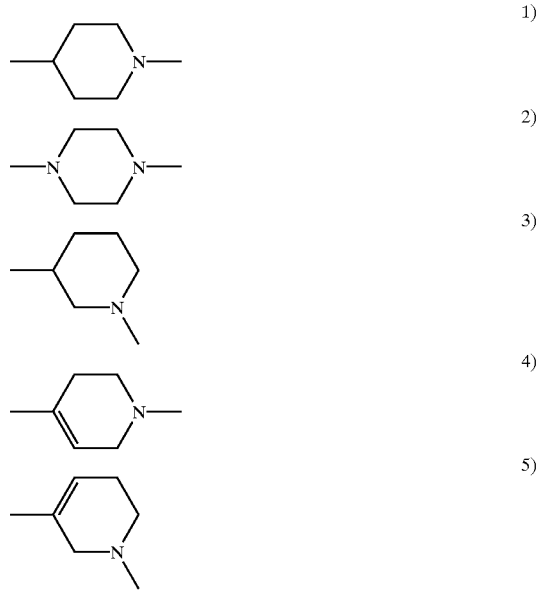

Ar² is indolyl, quinolinyl, benzimidazolyl, benzofuiranyl, or benzothiophenyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is alkylene having 3 to 8 carbon atoms, phenylene, or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:
1) —NR²R³,
wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylmino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms, where $R^2=R^3=H$ and $R^2=R^3=$ethyl are excluded), or —$NR^2R^3$ together forms piperidine, pyrrolidine, 1,3,4-trihydroisoquinoline, isoindoline, piperazine, morpholine, 2-piperidone, 2-pyrrolidone, indoline, 2,3,4-trihydroquinoline, 2,3,4trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

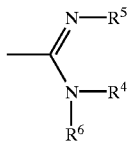

(II)

(wherein each of $R^4$, $R^5$, $R^6$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms), or $R^4$ and $R^5$ together form an imidazoline ring)).

8. A compound or a pharmacologically acceptable acid addition salt thereof according to claim 7, wherein, in the formula (II), D represents one of the following formulae 1) or 3), each of which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

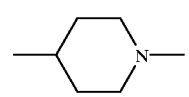

1)

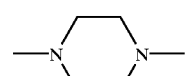

2)

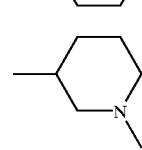

3)

$Ar^2$ is indolyl, quinolinyl, or benzimidazolyl, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is alkylene having 3 to 8 carbon atoms or cycloalkylene having 3 to 8 carbon atoms, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:
1) —$NR^2R^3$,
  wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having I to 15 carbon atoms, alkylthio group having 1 to 8 carbon atoms, and arylthio group having 6 to 15 carbon atoms, where $R^2$=$R^3$=H and $R^2$=$R^3$=ethyl are excluded), or —$NR^2R^3$ together forms piperidine, pyrrolidine, 1,3,4-trihydroisoquinoline, isoindoline, piperazine, morpholine, indoline, 2,3,4trihydroquinoline, 2,3,4-trihydroquinoxaline, dihydrobenzoxazine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxyl group, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, eyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

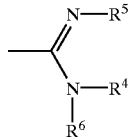

(II)

(wherein $R^4$, $R^5$, and $R^6$ have the same meanings as defined in claim 7).

9. A compound or a pharmacologically acceptable acid addition salt thereof according to one of claims 7 and 8, wherein, in the formula (III), D represents the following formula 1), which is unsubstituted or substituted with the groups selected from the group consisting of halogen, hydroxy, alkyl group having 1 to 8 carbon atoms, aryl group having 6 to 15 carbon atoms, haloalkyl group having 1 to 8 carbon atoms, aminosulfonyl group having 0 to 15 carbon atoms, carboxyl group, alkoxycarbonyl group having 2 to 9 carbon atoms, aminocarbonyl group having 1 to 15 carbon atoms, hydroxyalkyl group having 1 to 8 carbon atoms, alkylcarbonyl group having 2 to 9 carbon atoms, arylcarbonyl group having 7 to 16 carbon atoms, and aralkyl group having 7 to 15 carbon atoms;

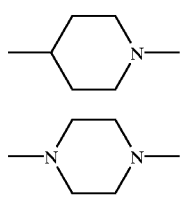

1)

2)

$Ar^2$ is indolyl, each of which is unsubstituted or substituted with the groups selected from the group consisting of halogen, nitro group, acylamino group having 1 to 9 carbon atoms, amino group, alkylamino group having 1 to 8 carbon atoms, arylaamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

A is alkylene having 3 to 8 carbon atoms, which is unsubstituted or substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms;

$Q^2$ is:

1) $-NR^2R^3$, wherein each of $R^2$ and $R^3$ is independently hydrogen, alkyl having 1 to 6 carbon atoms, cycloalkyl having 3 to 8 carbon atoms, alkenyl having 2 to 9 carbon atoms, aryl having 6 to 15 carbon atoms, or aralkyl having 7 to 15 carbon atoms (wherein the aryl moiety of the aryl and aralkyl may be substituted with the groups selected from the group consisting of halogen, nitro group, acylamino group having 1 to 9 carbon atoms, amino group, alkylamino group having 1 to 8 carbon atoms, arylamino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms, where $R^2=R^3=H$ and $R^2=R^3=$ethyl are excluded), or $-NR^2R^3$ together forms piperidine, pyrrolidine, 1,3,4-trihydroisoquinoline, isoindoline, piperazine, morpholine, or guanidine, each of which is unsubstituted or substituted with the groups selected from the group consisting of halogen, nitro group, acylamino group having 1 to 9 carbon atoms, amino group, alkylamino group having 1 to 8 carbon atoms, arylarnino group having 6 to 15 carbon atoms, dialkylamino group having 2 to 16 carbon atoms, diarylamino group having 12 to 20 carbon atoms, hydroxy, alkyl group having 1 to 8 carbon atoms, aryl group having 6 to 15 carbon atoms, alkoxy group having 1 to 8 carbon atoms, aryloxy group having 6 to 15 carbon atoms, haloalkyl group having 1 to 8 carbon atoms, haloalkoxy group having 1 to 8 carbon atoms, cyano group, aminosulfonyl group having 0 to 15 carbon atoms, carboxyl group, alkoxycarbonyl group having 2 to 9 carbon atoms, aminocarbonyl group having 1 to 15 carbon atoms, alkylthio group having 1 to 8 carbon atoms, and arylthio group having 6 to 15 carbon atoms; or 2) the formula (II):

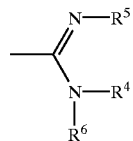

(II)

(wherein $R^4$, $R^5$, and $R^6$ have the same meanings as defined in claim 7).

10. A pharmaceutical composition comprising a compound represented by the formula (III) or a pharmacologically acceptable acid addition salt thereof according to claim 7 and a carrier.

11. A method of treating diseases associated with the α1B adrenoceptor comprising administering to a patient a therapeutically effective amount of an α1B adrenoceptor antagonist compound represented by the formula (III) or a pharmacologically acceptable acid addition salt thereof according to claim 7.

12. A method for treating circulatory disease comprising administering to a patient a therapeutically effective amount of a compound represented by the formula (III) or a pharmacologically acceptable acid addition salt thereof according to claim 7 as an active ingredient.

13. A method for treating hypertension comprising administering to a patient a therapeutically effective amount of a compound represented by the formula (III) or a phaarmacologically acceptable acid addition salt thereof according to claim 7 as an active ingredient.

* * * * *

UNITED STATES PATENT AND TRADEMARK OFFICE
CERTIFICATE OF CORRECTION

PATENT NO.    : 6,642,228 B1
DATED         : November 4, 2003
INVENTOR(S)   : Hayashi et al.

It is certified that error appears in the above-identified patent and that said Letters Patent is hereby corrected as shown below:

Title page,
Item [30], Foreign Application Priority Data, please change "11/178170" to -- 178170/99 --.

Column 1,
Line 17, please change "a receptors" to -- α receptors --; and
Line 60, please delete "e -".

Column 128,
Line 13, please change "aiB:" to -- α1B --.

Column 136
Line 35, please delete formula 2.

Column 137,
Line 53, please change "$Ar_2$-A-A-$Q^2$" to -- $Ar^2$-D-A-$Q^2$ --.

Column 138,
Line 10, please delete formula 2.

Column 140,
Line 40, please delete formula 2.

Column 142,
Line 35, please delete formula 2.

Signed and Sealed this

Third Day of August, 2004

JON W. DUDAS
*Acting Director of the United States Patent and Trademark Office*